US007736328B2

(12) United States Patent
Childers et al.

(10) Patent No.: US 7,736,328 B2
(45) Date of Patent: Jun. 15, 2010

(54) DIALYSIS SYSTEM HAVING SUPPLY CONTAINER AUTOCONNECTION

(75) Inventors: Robert W. Childers, Trinity, FL (US); Kurt Holmquist, Lutz, FL (US); Peter A. Hopping, Lutz, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 120 days.

(21) Appl. No.: 11/773,750

(22) Filed: Jul. 5, 2007

(65) Prior Publication Data
US 2009/0012455 A1     Jan. 8, 2009

(51) Int. Cl.
*A61M 1/00* (2006.01)
(52) U.S. Cl. .................. 604/29; 604/905; 604/533; 604/534; 604/535; 604/536
(58) Field of Classification Search .......... 604/29, 604/533–536, 538, 905; 138/89, 96 R
See application file for complete search history.

(56) References Cited

U.S. PATENT DOCUMENTS

| | | | |
|---|---|---|---|
| 1,896,379 A | 2/1933 | Ross | |
| 2,145,196 A | 1/1939 | Biggs | |
| 2,249,473 A | 7/1941 | Jackson | |
| 3,227,877 A | 1/1966 | Dreyfus | |
| 3,391,951 A | 7/1968 | Miller | |
| 3,413,097 A | 11/1968 | Jungner | |
| 3,626,938 A | 12/1971 | Versaci | |
| 3,709,222 A | 1/1973 | Devries | |
| 3,780,736 A | 12/1973 | Chen | |
| 3,814,680 A | 6/1974 | Wood | |
| 3,840,011 A | 10/1974 | Wright | |
| 3,916,950 A | 11/1975 | Mongerson et al. | |
| 3,926,556 A | 12/1975 | Boucher | |
| 3,955,922 A | 5/1976 | Moulthrop | |
| 3,957,082 A | 5/1976 | Fuson et al. | |
| 3,986,508 A | 10/1976 | Barrington | |
| 3,994,686 A | 11/1976 | Rauser et al. | |

(Continued)

FOREIGN PATENT DOCUMENTS

EP     0482858     4/1989

(Continued)

OTHER PUBLICATIONS

International Search Report and the Written Opinion for International Application No. PCT/US2008/068908 mailed on Mar. 19, 2009.

*Primary Examiner*—Kevin C Sirmons
*Assistant Examiner*—Larry R Wilson
(74) *Attorney, Agent, or Firm*—K&L Gates LLP

(57) ABSTRACT

A dialysis system includes a dialysis instrument including at least one pump actuator; a disposable cassette operable with the at least one pump actuator, a plurality of supply lines connected to the disposable cassette, each supply line including a supply line connector and a supply line tip protector; a plurality of dialysis fluid containers, the dialysis fluid containers each including a solution line having a solution line connector and a solution line tip protector; and an auto-connection mechanism including a solution line connector holder, a supply line connector holder, one of the holders fixed, the other of the holders moveable, and a moveable tip protector remover.

18 Claims, 40 Drawing Sheets

U.S. PATENT DOCUMENTS

| | | | |
|---|---|---|---|
| 4,056,116 A | 11/1977 | Carter et al. | |
| 4,063,890 A | 12/1977 | Baron | |
| 4,069,153 A | 1/1978 | Gunther | |
| 4,080,965 A | 3/1978 | Phillips | |
| 4,096,859 A | 6/1978 | Agarwal et al. | |
| 4,121,107 A | 10/1978 | Bachmann | |
| 4,141,686 A | 2/1979 | Lewis | |
| 4,169,474 A | 10/1979 | Wagner | |
| 4,173,234 A | 11/1979 | Thomas et al. | |
| 4,196,730 A | 4/1980 | Wilson | |
| 4,201,917 A | 5/1980 | Graentzel | |
| 4,219,055 A | 8/1980 | Wright | |
| 4,219,221 A | 8/1980 | Webb | |
| 4,239,041 A | 12/1980 | Popovich et al. | |
| 4,242,310 A | 12/1980 | Greff et al. | |
| 4,291,701 A | 9/1981 | Bowman | |
| 4,306,976 A | 12/1981 | Bazzato | |
| 4,338,933 A | 7/1982 | Bayard et al. | |
| 4,346,703 A | 8/1982 | Dennehey et al. | |
| 4,387,879 A | 6/1983 | Tauschinski | |
| 4,405,315 A | 9/1983 | Handt | |
| 4,412,834 A | 11/1983 | Kulin et al. | |
| 4,433,244 A | 2/1984 | Hogan | |
| 4,439,193 A | 3/1984 | Larkin | |
| 4,475,900 A | 10/1984 | Popovich et al. | |
| 4,500,788 A | 2/1985 | Kulin et al. | |
| 4,503,333 A | 3/1985 | Kulin et al. | |
| 4,541,829 A | 9/1985 | Munsch et al. | |
| 4,557,727 A | 12/1985 | Handt | |
| 4,596,551 A | 6/1986 | Golinski et al. | |
| 4,617,012 A | 10/1986 | Vaillcourt | |
| 4,626,245 A | 12/1986 | Weinstein | |
| 4,626,845 A | 12/1986 | Ley | |
| 4,655,753 A | 4/1987 | Bellotti et al. | |
| 4,655,762 A | 4/1987 | Rogers | |
| 4,675,007 A | 6/1987 | Terry | |
| 4,695,276 A | 9/1987 | Shinno et al. | |
| 4,738,668 A | 4/1988 | Bellotti et al. | |
| 4,755,292 A | 7/1988 | Merriam | |
| 4,769,017 A | 9/1988 | Fath et al. | |
| 4,774,415 A | 9/1988 | Biegel et al. | |
| 4,840,621 A | 6/1989 | Larkin et al. | |
| 4,869,286 A | 9/1989 | Williams et al. | |
| 4,873,446 A | 10/1989 | Kreitmair et al. | |
| 4,878,516 A | 11/1989 | Mathieu | |
| 4,882,496 A | 11/1989 | Bellotti et al. | |
| 4,952,812 A | 8/1990 | Miripol et al. | |
| D310,881 S | 9/1990 | Larkin et al. | |
| 5,014,494 A | 5/1991 | George | |
| 5,047,011 A | 9/1991 | Caron et al. | |
| 5,057,074 A | 10/1991 | Suzuki et al. | |
| 5,125,911 A | 6/1992 | Grabenkort et al. | |
| 5,184,020 A | 2/1993 | Hearst et al. | |
| 5,250,041 A | 10/1993 | Folden et al. | |
| 5,279,605 A | 1/1994 | Karrasch et al. | |
| 5,311,899 A | 5/1994 | Isayama et al. | |
| 5,334,139 A | 8/1994 | Jeppsson et al. | |
| 5,350,357 A * | 9/1994 | Kamen et al. | 604/29 |
| 5,399,156 A | 3/1995 | Lindsay | |
| 5,472,720 A | 12/1995 | Rakhimov et al. | |
| 5,540,265 A | 7/1996 | Polaschegg et al. | |
| 5,542,913 A | 8/1996 | Lindsay | |
| 5,572,992 A | 11/1996 | Kankkunen et al. | |
| 5,583,948 A | 12/1996 | Shibayama | |
| 5,611,506 A | 3/1997 | Berger et al. | |
| 5,612,001 A | 3/1997 | Matschke | |
| 5,647,984 A | 7/1997 | Hovland et al. | |
| 5,707,911 A | 1/1998 | Rakhimov et al. | |
| 5,714,119 A | 2/1998 | Kawagoe et al. | |
| 5,733,457 A | 3/1998 | Hovland et al. | |
| 5,792,419 A | 8/1998 | Williamson et al. | |
| 5,843,379 A | 12/1998 | Kristensen | |
| 5,900,211 A | 5/1999 | Dunn et al. | |
| 5,925,014 A | 7/1999 | Teeple, Jr. | |
| 5,948,247 A | 9/1999 | Gillerfalk et al. | |
| 6,013,918 A | 1/2000 | Bushnell et al. | |
| 6,146,600 A | 11/2000 | Williamson | |
| 6,171,561 B1 | 1/2001 | Williamson et al. | |
| 6,228,332 B1 | 5/2001 | Dunn et al. | |
| 6,234,538 B1 | 5/2001 | Lauer | |
| 6,245,570 B1 | 6/2001 | Grimm et al. | |
| 6,293,921 B1 * | 9/2001 | Shinmoto et al. | 604/29 |
| 6,440,095 B1 | 8/2002 | Utterberg | |
| 6,443,147 B1 | 9/2002 | Matter | |
| 6,461,568 B1 | 10/2002 | Eckhardt | |
| 6,468,424 B1 * | 10/2002 | Donig et al. | 210/232 |
| 6,565,525 B1 | 5/2003 | Burbank et al. | |
| 6,565,803 B1 | 5/2003 | Bolton et al. | |
| 6,696,023 B2 | 2/2004 | Grimm et al. | |
| 6,730,113 B2 | 5/2004 | Eckhardt et al. | |
| 6,736,797 B1 | 5/2004 | Larsen et al. | |
| 6,814,726 B1 | 11/2004 | Lauer | |
| 6,911,025 B2 | 6/2005 | Miyahara | |
| 7,083,605 B2 | 8/2006 | Miyahara | |
| 7,195,615 B2 | 3/2007 | Tan | |
| 7,232,429 B2 | 6/2007 | Moreci | |
| 7,306,197 B2 | 12/2007 | Parrino et al. | |

FOREIGN PATENT DOCUMENTS

| | | |
|---|---|---|
| EP | 0575970 | 12/1993 |
| WO | 86/04674 | 8/1986 |
| WO | 92/11046 | 7/1992 |
| WO | 96/25214 | 8/1996 |
| WO | 03/099355 | 12/2003 |

* cited by examiner

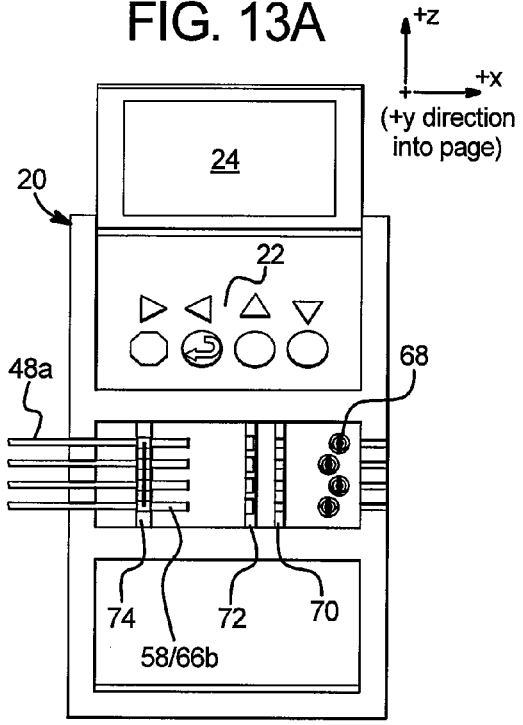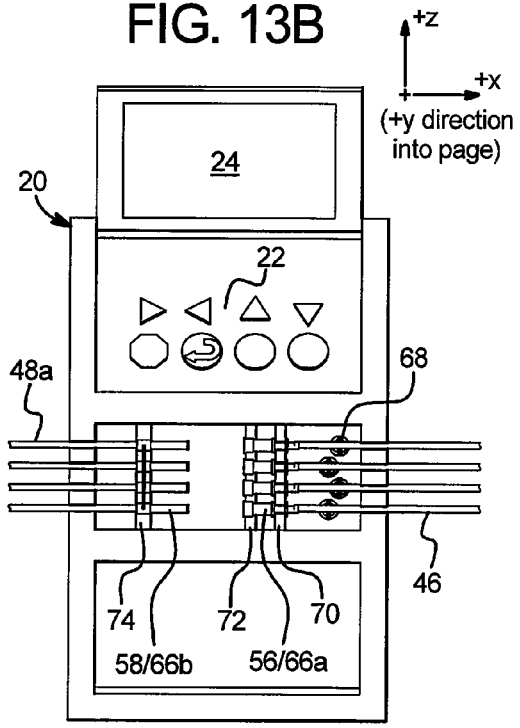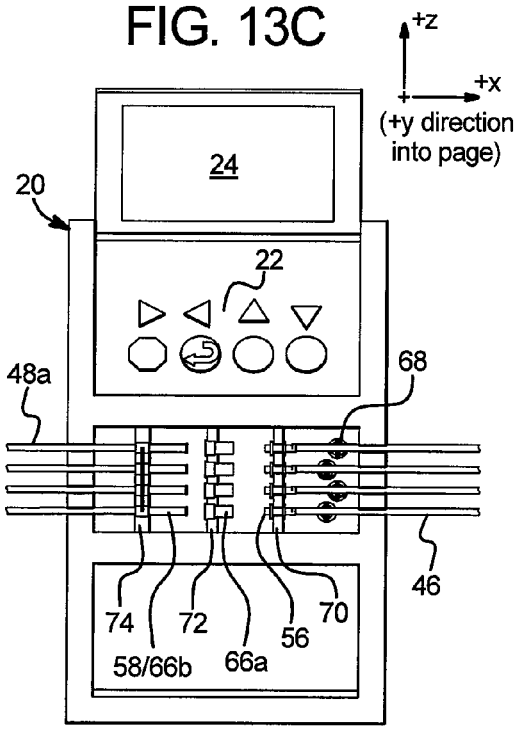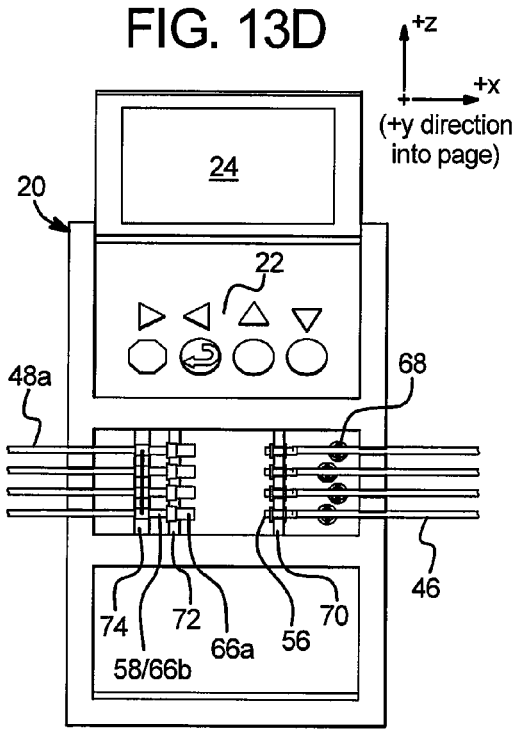

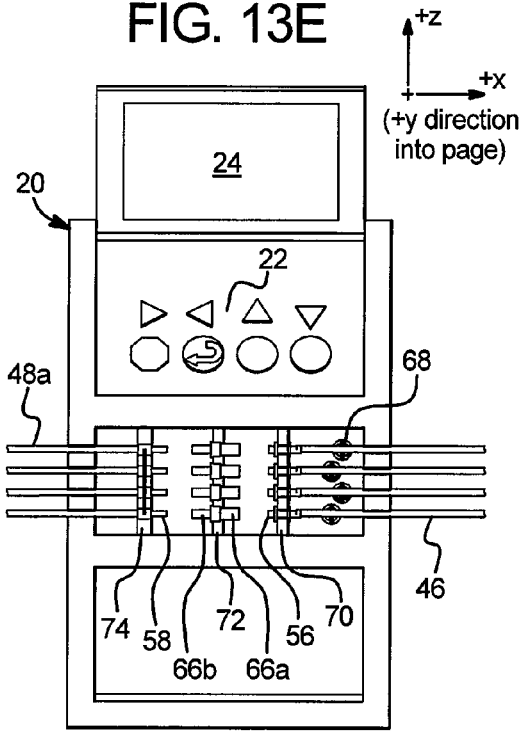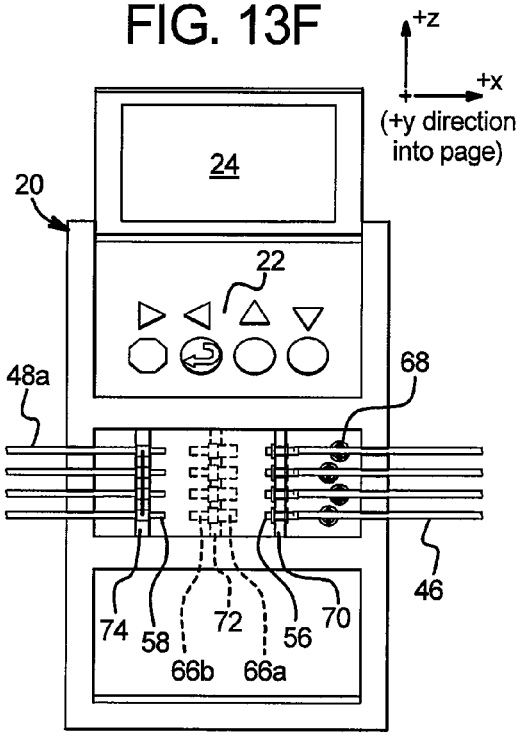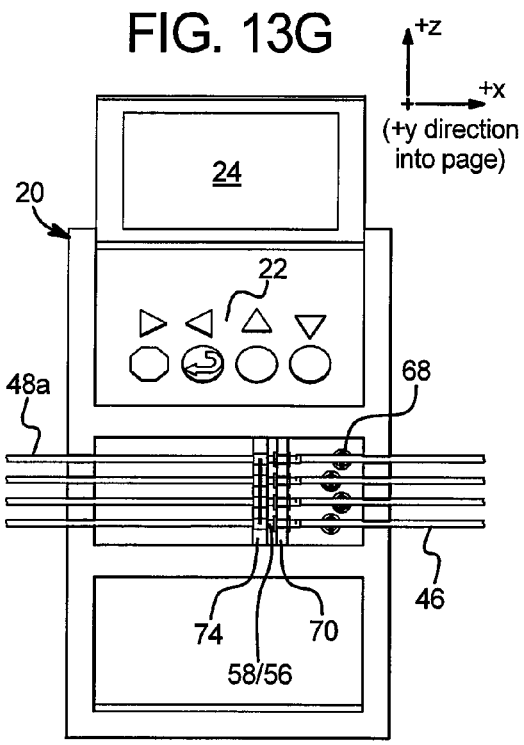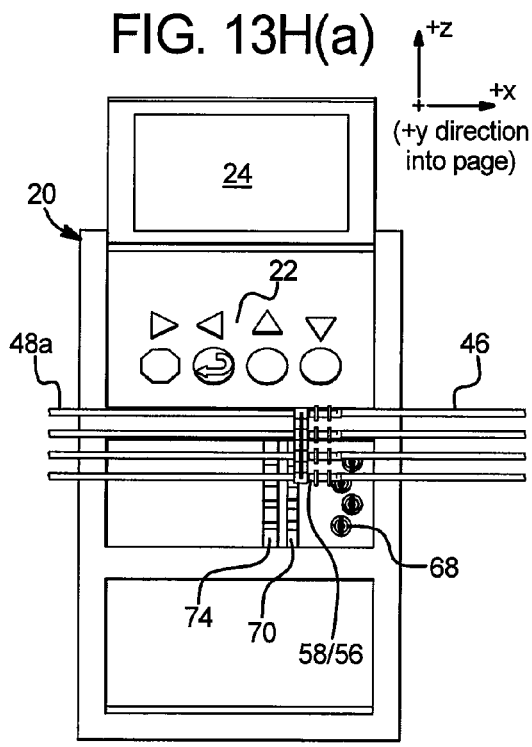

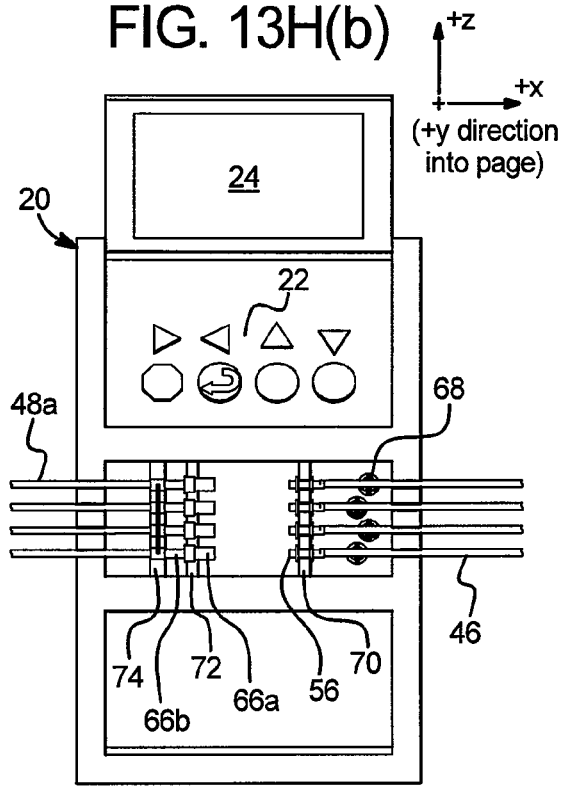
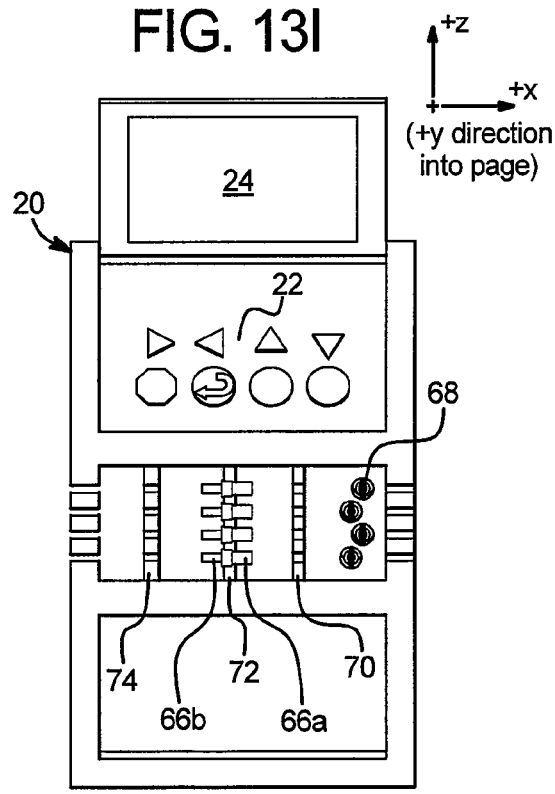

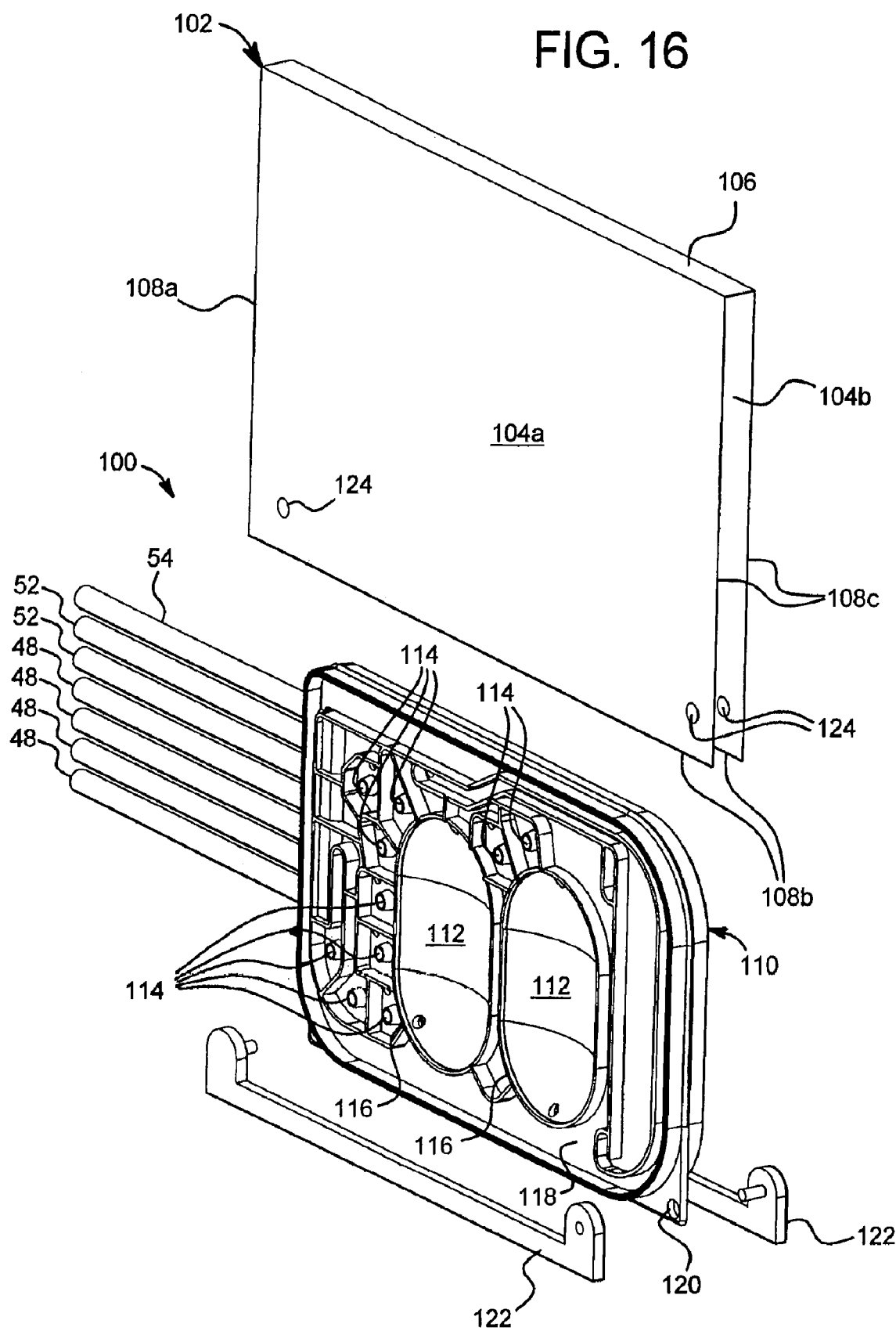

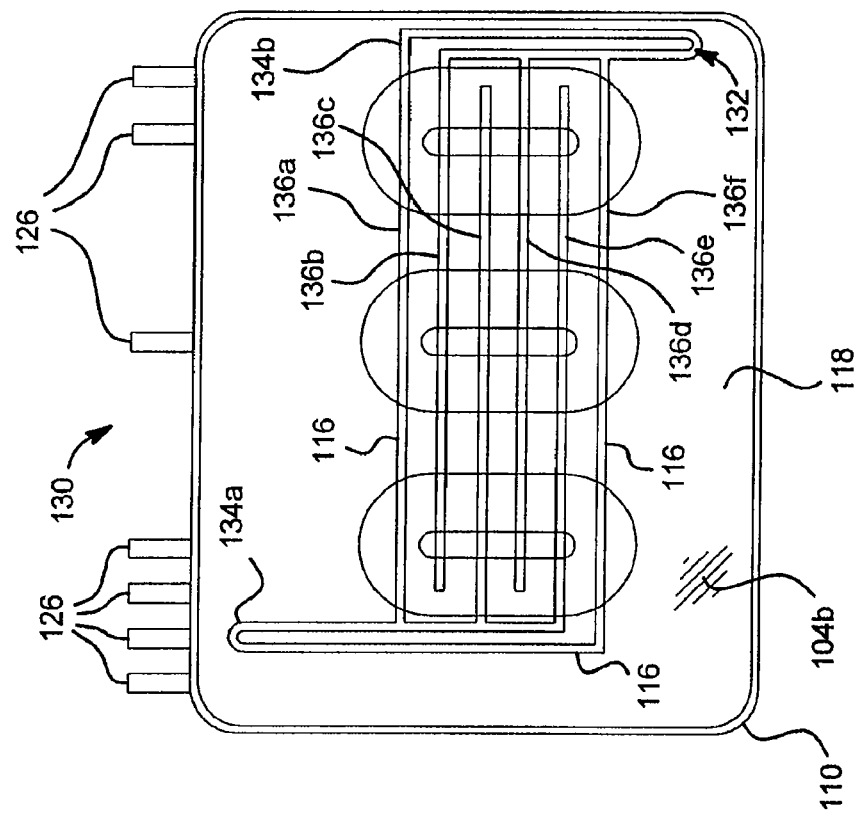
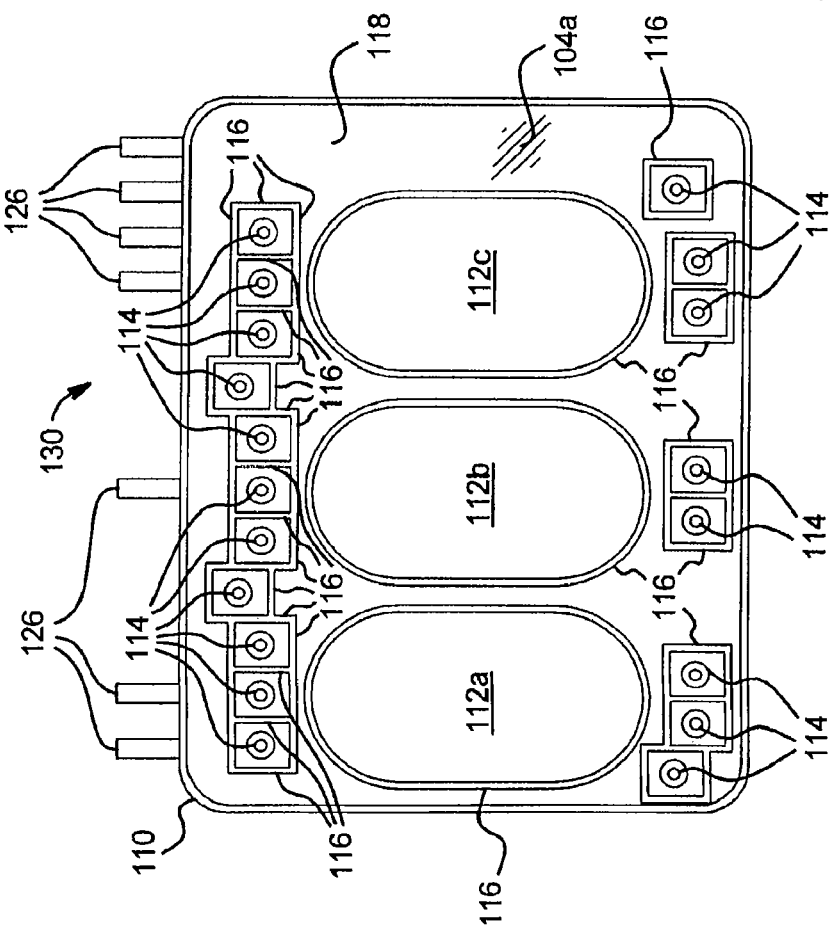

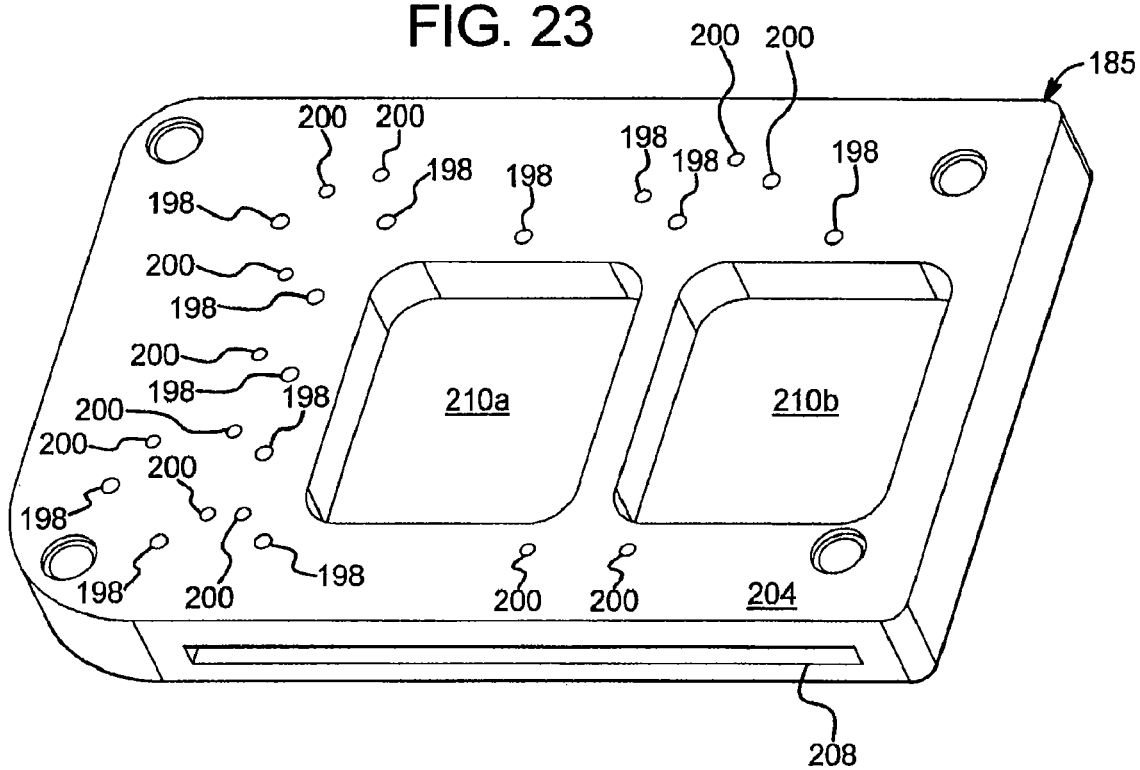
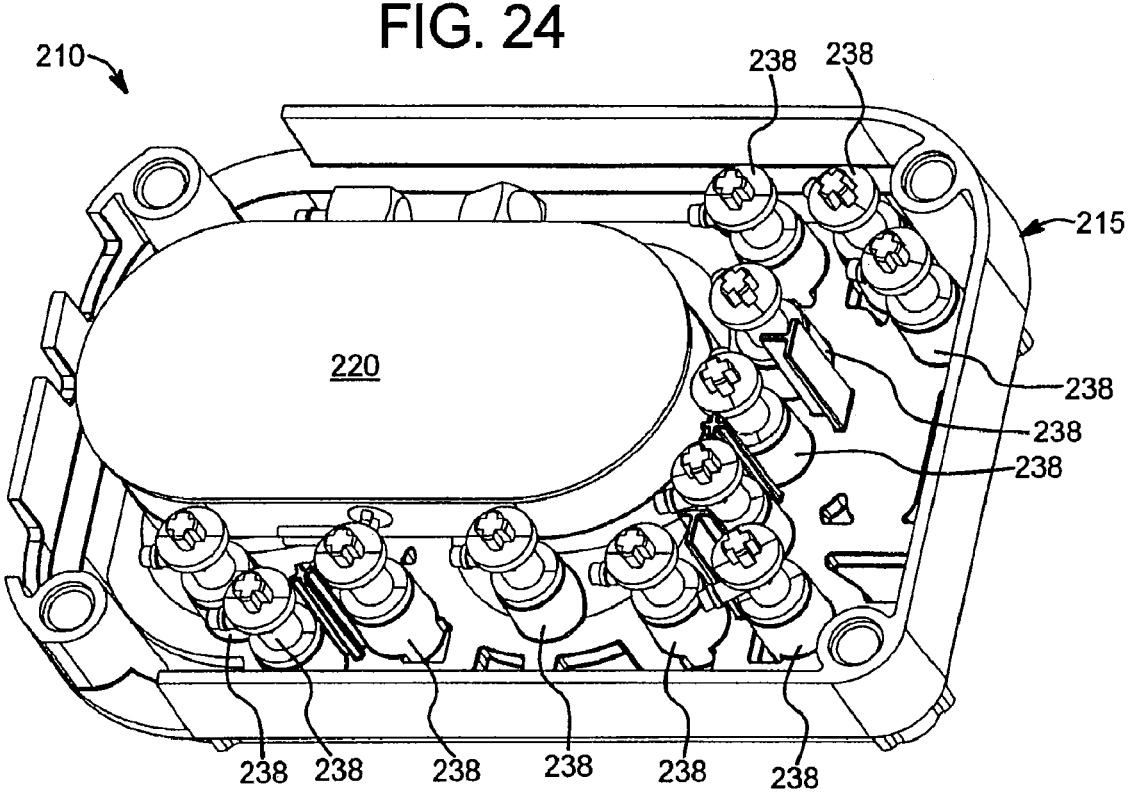

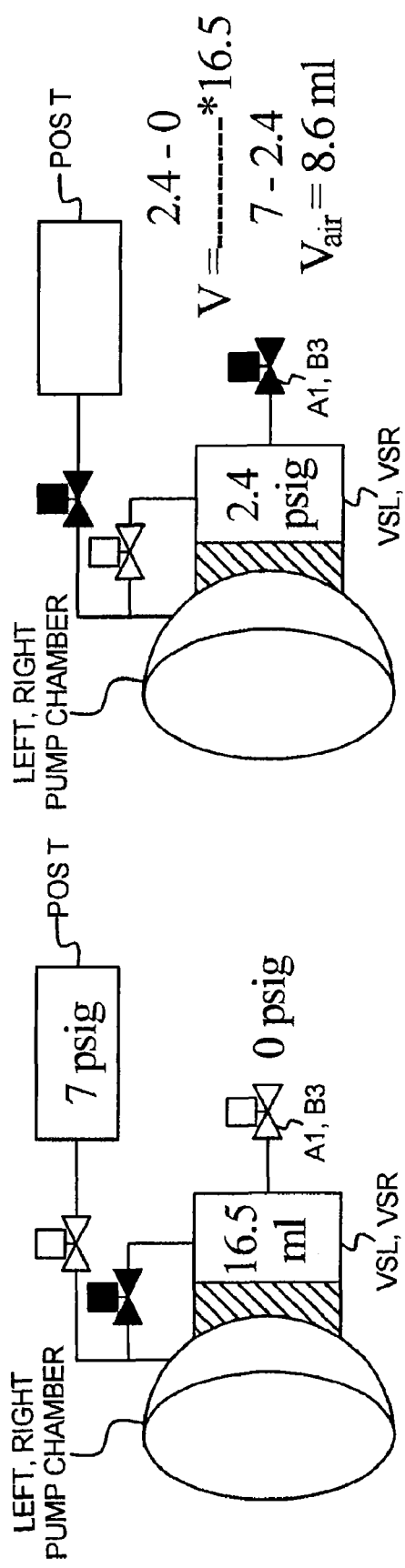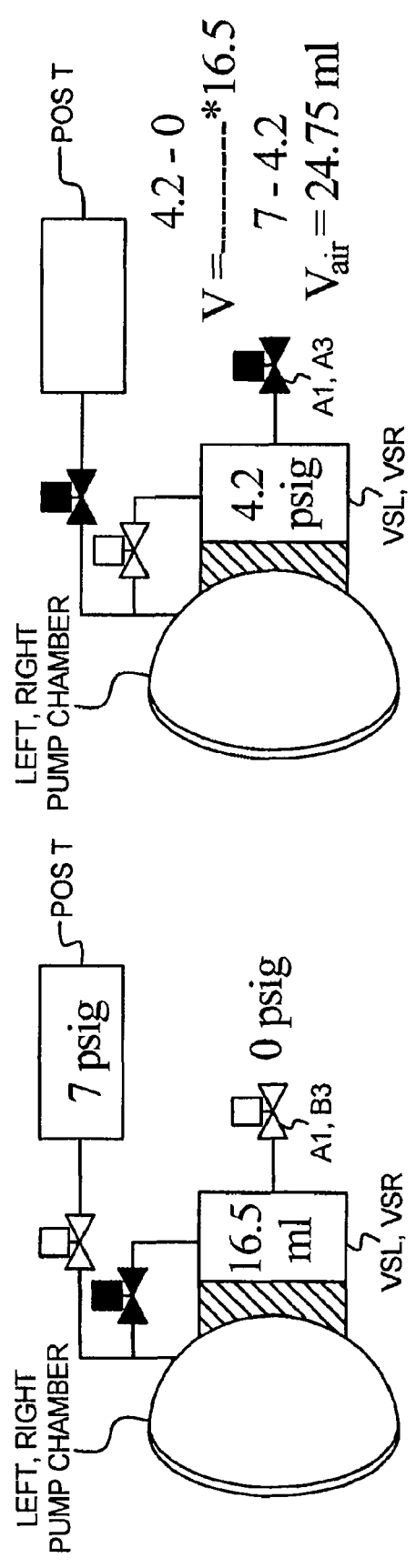
FIG. 28A  FIG. 28B  FIG. 28C  FIG. 28D

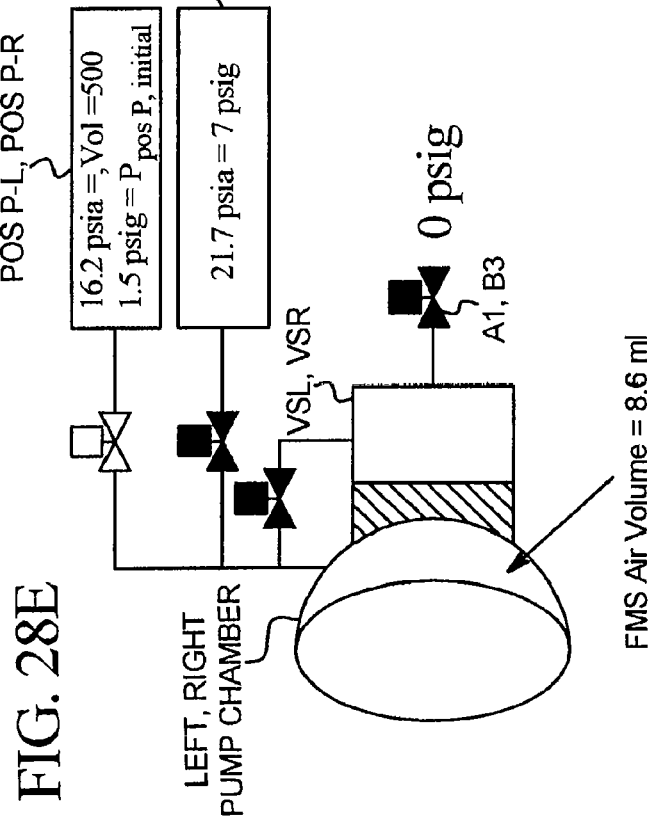
FIG. 28F
FIG. 28E
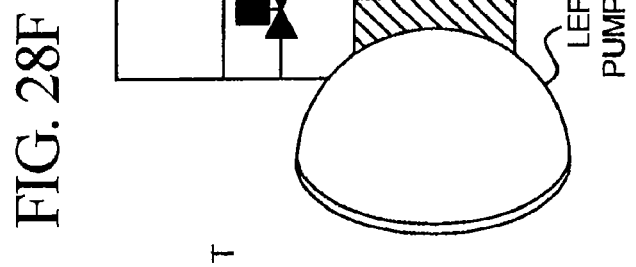
$$\text{Volume Pumped} = \left(\frac{P_{POS\,P,\,initial}}{P_{POS\,P,\,t}} - 1\right)(500 + 8.6)$$
| P1 (psia) | Vol Pumped (ml) |
|---|---|
| 16.20 | 0.00 |
| 16.10 | 3.16 |
| 16.00 | 6.35 |
| 15.90 | 9.59 |
| 15.80 | 12.87 |
| 15.70 | 16.19 |
FIG. 29

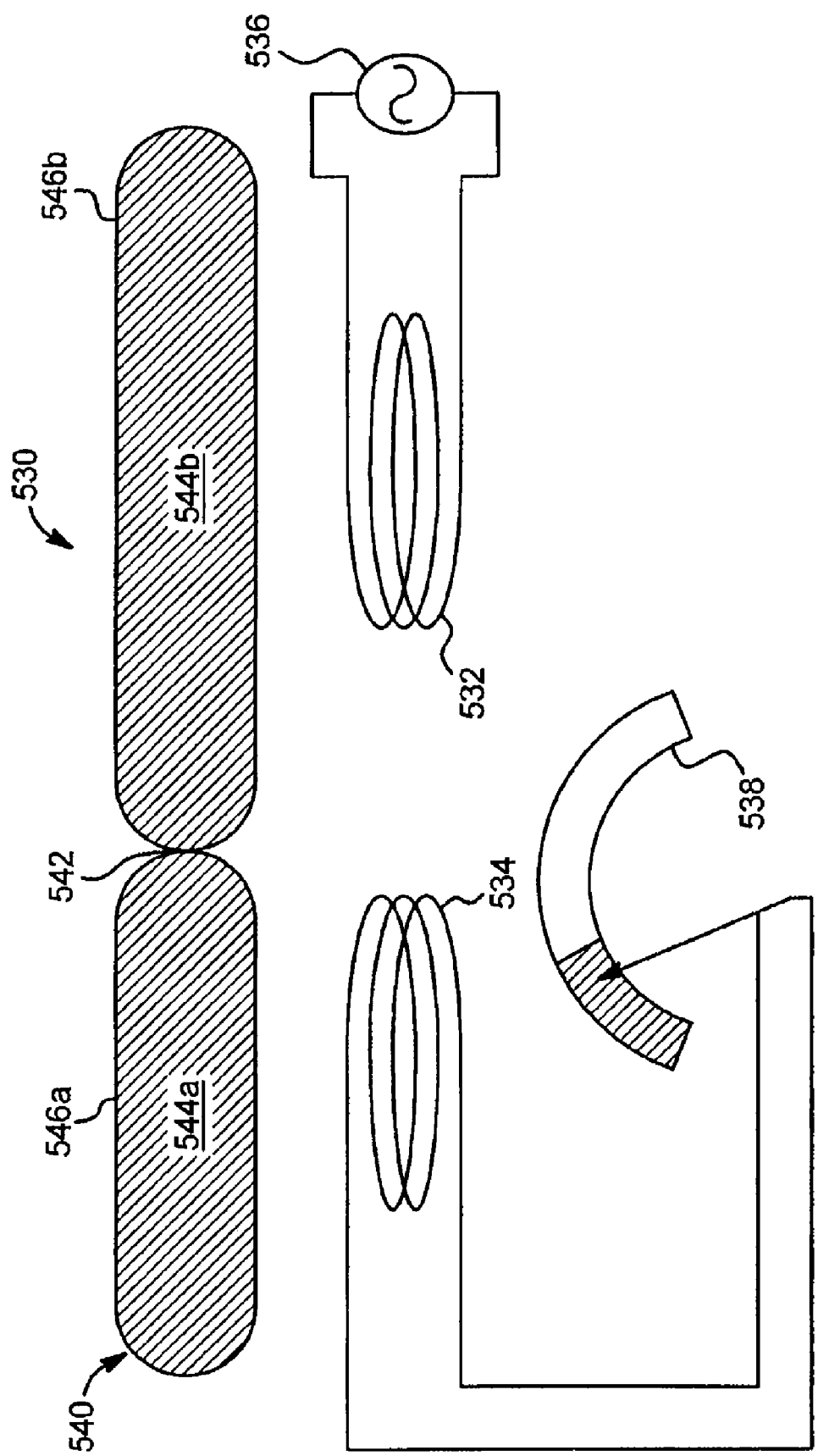

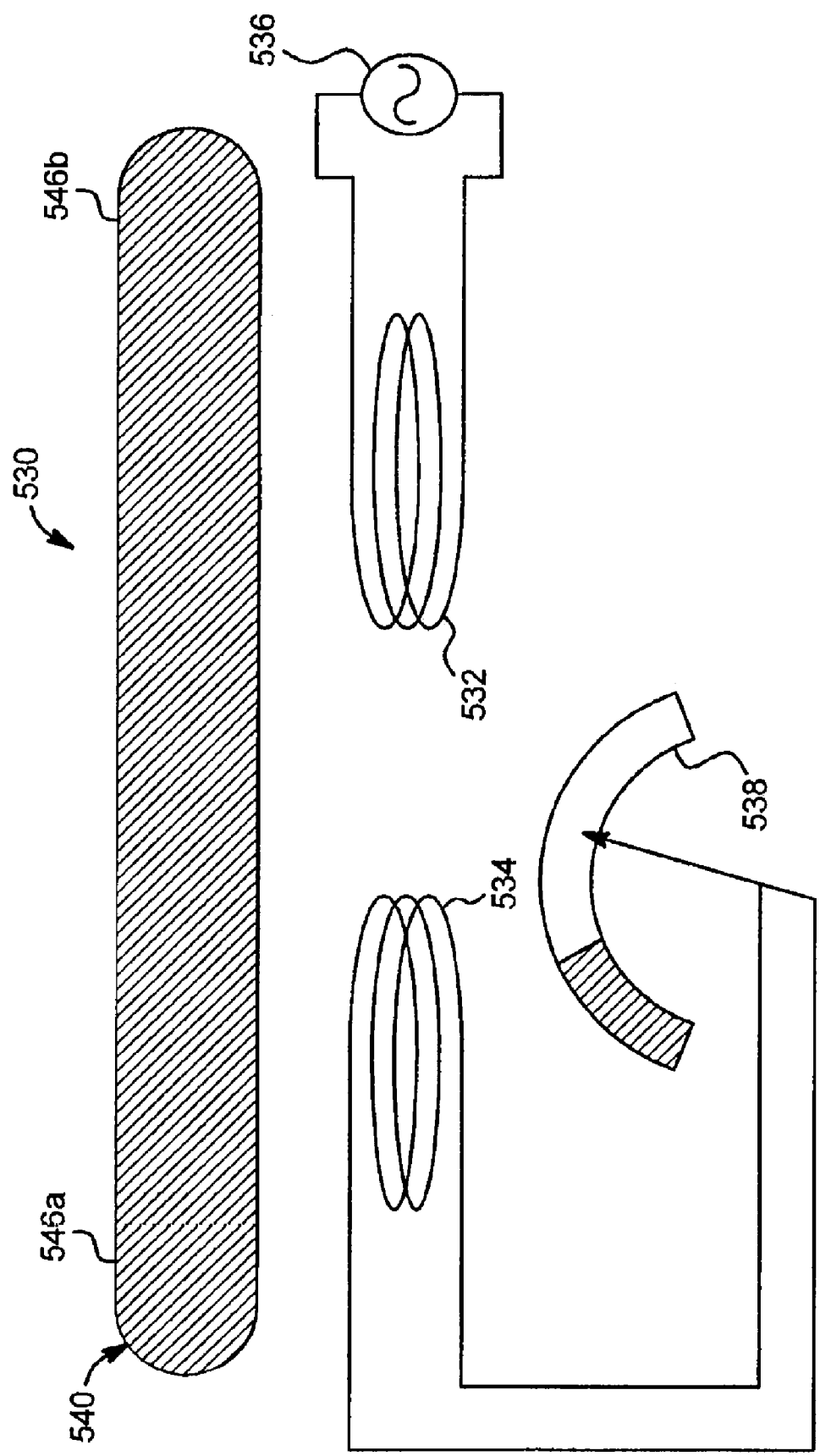

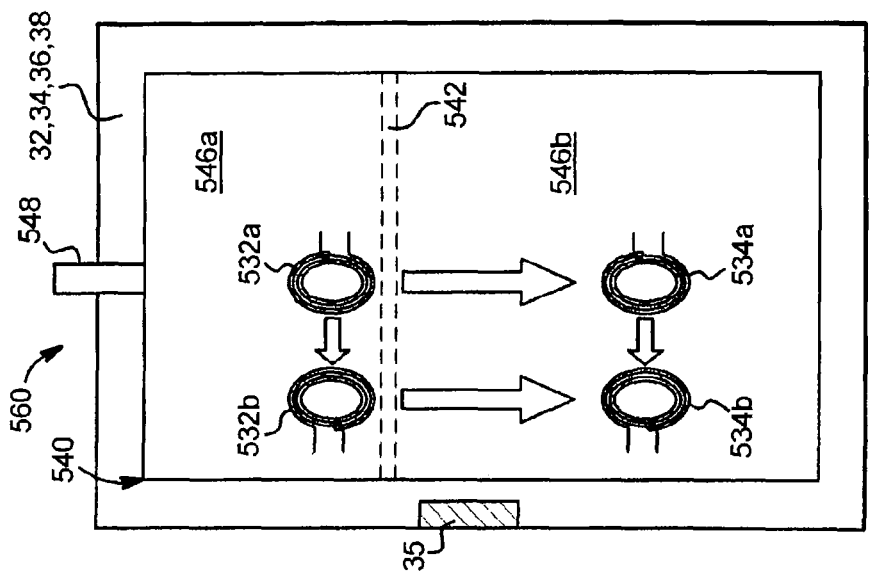
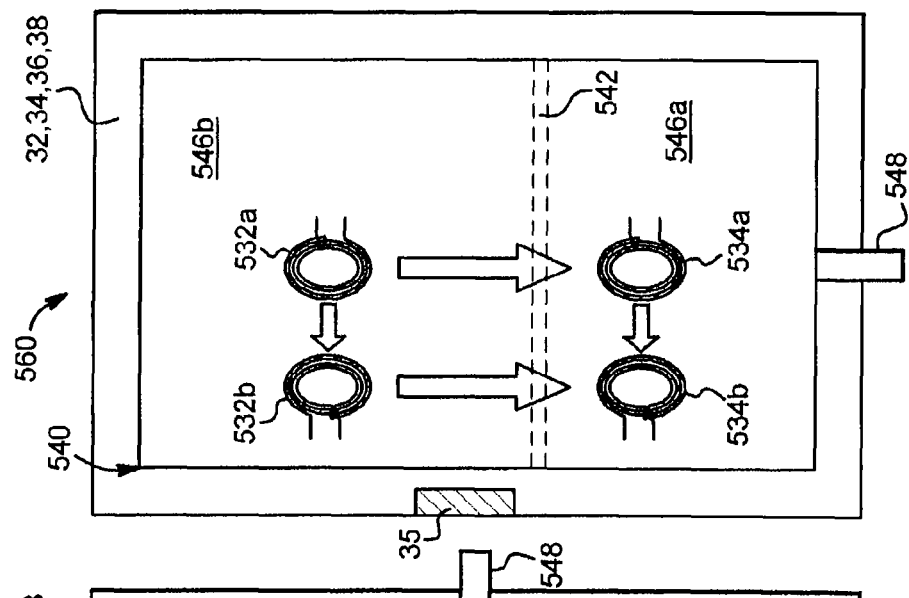
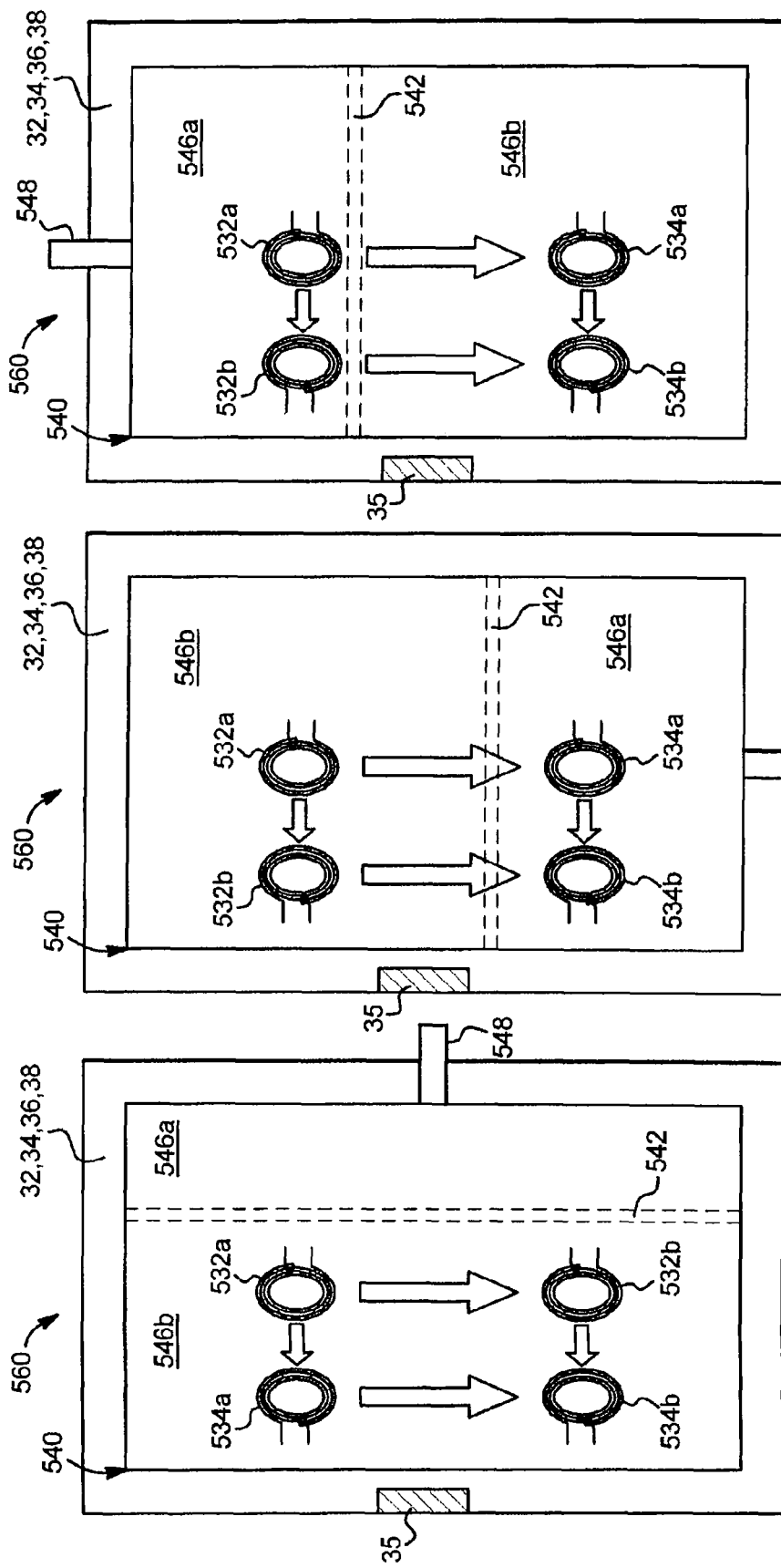
FIG. 37D
FIG. 37C
FIG. 37B

DIALYSIS SYSTEM HAVING SUPPLY CONTAINER AUTOCONNECTION

BACKGROUND

The examples discussed below relate generally to medical fluid delivery. More particularly, the examples disclose systems, methods and apparatuses for automated peritoneal dialysis ("APD").

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow for the dialysate to dwell within the cavity and for the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysis. A "last fill" occurs at the end of APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Some continuous flow, or CFPD, systems clean or regenerate spent dialysate instead of discarding it. Others use a large volume of fresh dialysate. The systems pump fluid into and out of the patient, through a loop. In a regenerating system, dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroducing the dialysate into the peritoneal cavity. Additional sensors are employed to monitor the removal of ammonia. Regenerating CFPD systems are typically more complicated than batch systems.

Peritoneal dialysis (PD) systems, home hemodialysis/hemofiltration, and intensive care unit procedures that use bagged peritoneal dialysate, hemodialysis dialysate, or hemofiltration substitution solution can use a dual chamber bag. For example, bicarbonate based solutions have been developed for certain ones of the above applications. Bicarbonate is unstable in the presence of magnesium and calcium and forms a precipitate after a period of time. The bicarbonate based solutions are accordingly provided in a dual chamber bag. Prior to use, a seal between the two chambers is broken and the two concentrate solutions are mixed and used before calcium or magnesium precipitate can form. Unfortunately, a single concentrate solution delivered to a patient due to the two concentrate solutions not mixing can create a physiologically unsafe condition for the patient.

The system below addresses various drawbacks with the above-mentioned medical fluid treatments.

SUMMARY

The present disclosure describes an improved automated peritoneal dialysis ("APD") system, however, many of the teachings herein are applicable to other medical fluid treatments, especially other renal failure therapy treatments, such as hemodialysis ("HD"), hemofiltration ("HF"), hemodiafiltration ("HDF") and continuous renal replacement therapy ("CRRT").

The system offers improved treatment and ease of use features. The system is mobile in one embodiment so that the patient can, for example, start a therapy in the family room and move the system to a bedroom on the same floor. The system manages supply bags, which are carried with the device or instrument when the patient moves the instrument. The system also employs a bag management system, which tilts the supply bags so that gravity will cause fluid to flow from them, leaving air behind during the priming sequence and normal operation. The gravity induced air separation at the supply bags allows the system to pump at high flowrates because there is little concern that the air has not been removed properly while pumping the fluid.

The system provides a cart having a rotating bearing plate or "lazy Susan" that supports the instrument and allows it to be rotated for convenient operation, making at least the vast majority of system features readily accessible. This may allow the patient to correct most alarms without getting out of bed. The "lazy Susan" plate can optionally have detent positions every ninety degrees or so.

The system includes an improved priming procedure using a patient line having dual lumens. During the patient line prime, fluid flows down one lumen away from a disposable cassette and back up the other lumen towards the cassette forming a closed loop feedback that indicates when priming is complete. This feedback is operable even with patient line extensions. U.S. Patent Application No. 2004/0019312 A1, FIG. 2, owned by the eventual assignee of the present disclosure, shows a tip protector for a dual lumen patient line that is compatible with this priming technique. The dual lumen line also eliminates the volume of spent effluent fluid that is pushed back (recirculated) when the instrument cycles from drain to fill. Additionally, the dual lumen line accommodates the sensing of intraperitoneal pressure ("IPP") to optimize patient fill and drain volumes as described in U.S. Pat. No. 6,497,676, owned by the eventual assignee of the present disclosure, the entire contents of which are incorporated expressly herein by reference. Further still, the dual lumen patient line allows the same disposable set to be used for large and small patients because the recirculation volume is near zero.

The system also provides an auto-connection mechanism that connects connectors from the supply bags to connectors of the cassette supply lines. In one embodiment, the system provides for up to four supply bags, which can be connected to a manifold of the auto-connection mechanism. Each solution bag can be the same or different. The auto-connection mechanism is advantageously able to use the same solution bag (e.g., made having existing spikes and spike septums with existing equipment and processes). Tip protectors which protect the supply and bag pigtail connectors are modified to be compatible with the auto-connection mechanism.

As discussed in detail below, the system of the present disclosure is readily adapted for a high-volume therapy. In one implementation, the system uses four-to-one manifolds, which allow any one or more of four supply bag inlets to the disposable cassette to be increased to up to four bags for treatment. The four-to-one manifolds work in conjunction with the auto-connection and auto-identification systems described herein. Up to four, four-to-one manifolds each manifold being able to connect to up to four (e.g., same-solution) supply bags can accommodate a therapy volume of, for example, up to ninety-six liters.

Each of the manifold lines in the four-to-one manifold is placed in the auto-connection mechanism for connection to the supply lines connected to the disposable cassette. The single supply line of the disposable cassette can now connect to up to four solution bags. An imaging system recognizes the four to one connector and the type of attachment made to the manifold (the one line) end of the four to one manifold.

The auto-connection system also includes an automatic clamping system, which allows the user to not have to clamp and unclamp solution lines during the connection process or when an alarm condition occurs.

An imaging system or solution identification system which verifies the volume, expiration date, composition, and configuration (e.g., single bag solution, multiple chamber bag solution, or multiple bag solution that requires mixing) before the bags are connected. The solution identification system verifies that the composition and volume of the solutions are consistent with the therapy prescription before connection. The solution identification system also: (i) automatically draws solution in the correct sequence when the correct solution bags are loaded; (ii) informs the user if the incorrect solution bags are loaded; and (iii) alerts the user if a solution bag connector is deformed, potentially causing an improper connection.

The disposable set (cassette, bags and lines) of the system is relatively simple and easy to use and requires fewer product codes because all geographic regions can use the same disposable set for both pediatric patients and adult patients, and with therapy volumes up to ninety-six liters. The lines of the disposable set are connected to organizers (e.g., cassette supply lines connected to a first organizer and patient and drain lines connected to a second organizer), which prevent the lines from becoming tangled and facilitate loading the lines into the auto-connection system.

The disposable set allows for admixing as described in U.S. Pat. No. 5,925,011, owned by the eventual assignee of the present disclosure, the entire contents of which are incorporated expressly herein by reference, or for the delivery of single part solutions, or double part solutions contained in a single bag. If a peel seal or frangible seal needs to be broken before use, the system can verify that it has been broken before the solution is delivered to the patient. Capacitive sensors located on the bag management shelves are used to verify that the seal has been broken and that the same solution is present in both chambers (ends) of the solution bag.

In an alternative embodiment, the sensor is an inductive sensor, which can (i) detect whether a emitter chamber bag has been loaded properly onto one of the bag management shelves and (ii) detect whether a frangible seal between two chambers bags has been broken such that the concentrate solutions can mixed properly for delivery to the patient. The inductive sensing apparatus and method are not limited to renal applications and can be used to confirm placement, mixing, etc., for any medical fluid system using dual or multi-chamber bagged solutions.

The system further provides a non-invasive temperature measuring feature or technique. The heat sensing technique uses a non-invasive infrared temperature sensor and electromagnet. The electromagnet controls the orientation of the temperature sensor. The disposable cassette has sheeting with a black or opaque area. A first orientation of the infrared sensor is trained on the black or opaque area and consequently measures the temperature of the sheeting. The second orientation of the infrared sensor is trained on an area of the sheeting which is not black or opaque and can thus see through the sheeting into the fluid behind the sheeting. This second infrared sensor reading measures a combination of the temperature of the film and the fluid. Discussed herein are algorithms for calculating the temperature of the fluid from the two infrared temperature readings.

The HomeChoice® APD System marketed by the eventual assignee of the present disclosure, uses a method described in U.S. Pat. No. 4,826,482 ("The '482 patent"), to determine the volume of fluid pumped to the patient or to the drain. That method in essence looks backwards after a pump stroke to see how much fluid has been pumped to the patient. While this system has been highly successful, there are various reasons to know the volume of fluid pumped during the pump stroke or in real time. The reasons are discussed in detail below but in general include: (i) being able to fill/drain a patient to a volume that is not equal to a whole number of pump strokes; (ii) being able to immediately know when a patient is drained to empty or virtually empty to reduce pain at the end of drain; (iv) providing accuracy needed for mixing solutions; and (v) helping to eliminate the need to have to provide an alternate source of fluid, so that a partially full pump chamber can be differentiated from a pump chamber containing air and fluid.

The real time system and method in one embodiment monitors the pressure decay in a pressurized tank in fluid communication with the pump chamber of the disposable cassette. The system knows the volume of air or gas ($V_{gas}$) in the pump chamber prior to opening the valve to the tank. Then, after the valve to the tank is opened the system takes pressure readings at desired intervals and performs a calculation after each reading. The initial pressure (P1) in the tank is known. If the pressure at any given point in time is taken as P1' then a ratio can be expressed in an equation form as follows:

$$((P1/P1')-1),$$

this ratio is multiplied by an addition of the gas volume $V_{gas}$ to a known volume of the tank $V_{tank}$ to form a real time volume of fluid pumped $V_{fluid} = ((P1/P1')-1)(V_{tank}+V_{gas})$. P1 is initially equal to P1', thus making the initial real time volume of fluid pumped equal to zero. As P1' becomes increasingly less than P1 over time, $((P1/P1')-1)$ becomes increasingly larger over time as does $V_{fluid}$.

The real time volumes are useful for many purposes as described above. Described below is an algorithm for using the real time volumes to determine features such as: (i) if a full pump stroke has occurred; (ii) if a line occlusion has occurred; (iii) if a leak has occurred; and (iv) if multiple concentrates have been mixed properly, for example.

The cassette in one embodiment has sheeting welded to the molded plastic piece as described in U.S. Pat. Nos. 5,401,342, 5,540,808, 5,782,575 and 6,001,201. In an alternative embodiment, the molded plastic piece is enclosed within welded sheeting but not welded to the sheeting. The sheeting in one embodiment is welded to itself and to the tubing attached to the cassette, allowing the inside of the sheeting, including the molded plastic piece to be isolated from the environment. This cassette assembly provides flexibility in material selection for the molded plastic, sheeting and tubing because the sheeting to molded plastic seal has been eliminated. The sheeting material therefore does not need to be compatible with the rigid cassette material from a welding or bonding standpoint.

A disposable cassette having three pumping chambers is also shown and described below. The three chamber cassette provides a number of advantages, such as allowing for continuous flow at both the inlet and outlet of the pump even when running a standard, e.g., batch, therapy. With two pump chambers, fluid measurement is performed in an attempt to make patient flow essentially continuous. For example, the fluid measurements can be made in one pump chamber, while the other pump chamber is halfway through its pump stroke and vice versa. Nevertheless, the fresh supply and drain flowrates are pulsatile because more fluid will be flowing at certain times than at others. The three pump cassette therefore allows for continuous flow to a patient even when two solutions are being mixed online.

The system also includes an improved cassette/manifold membrane assembly or system. The assembly or system includes an interface plate having pump actuation areas with actuation ports for allowing a positive or negative pressure to be applied within the pump actuation areas to the membrane gasket to correspondingly place a positive or negative pressure on a juxtaposed flexible sheeting of the disposable cassette. Likewise, the interface plate includes valve actuation areas with actuation ports for allowing a positive or negative pressure to be applied within the valve actuation areas to the membrane gasket to correspondingly place a positive or negative pressure on the juxtaposed flexible sheeting of the disposable cassette. In addition to the actuation ports, the cassette interface includes an evacuation port to evacuate air between the membrane gasket and cassette sheeting adjacent to each pump and each valve.

The gasket includes blind holes that seal around the sidewalls of the actuation ports of the valves or pump chambers. The blind holes include a sheath or thin portion that extends over the valve or pump actuation ports. Positive or negative pressure applied through actuation ports is therefore likewise applied to the sheath portion of the blind hole of the members. Positive or negative pressure applied to the sheath portion accordingly causes a flexing of the sheath portion and corresponding flexing of the cassette sheeting.

The membrane also provides a through-hole for each evacuation port of the interface plate. The through-holes seal around the sidewalls of the protruding evacuation ports and allow a negative pressure applied through the evacuation ports to suck the cassette sheeting against the sheath portions of the membrane gasket forming pump or valve areas. In this manner, for a given pump or valve area, the membrane gasket and cassette sheeting flex back and forth together.

If a hole develops in either the membrane gasket or the cassette sheeting, the vacuum level through the evacuation port at the leak decreases, indicating the leak. Thus the evacuation ports also serve as leak detectors that are placed in multiple places over the cassette, providing superior leak detection with the capability of indicating where on the cassette sheeting or membrane gasket the leak has occurred. This leak detection capability is present prior to the beginning of therapy as well as during therapy.

The system can also tell which of the membrane gasket and the cassette sheeting has incurred a leak. If fluid is not drawn between the membrane gasket and the sheeting, the leak is in the membrane gasket. If fluid is drawn in between the membrane gasket and the sheeting, the leak is in the cassette sheeting. This can be a valuable tool, for example, in diagnosing a machine that appears to be malfunctioning.

The cassette interface, in an embodiment, also integrates the pneumatic manifold with the cassette interface so that air that travels from the back side of the pumping chambers of the disposable cassette to the volumetric reference chambers (one for each pump chamber, used for volumetric accuracy calculation and air) of the pneumatic manifold does not have to travel far. The close spacing also tends to make the temperature of air in the passageways, the reference chambers and the pump chambers equal. This is useful for a pneumatic pumping technique that assumes a constant temperature between air in the volumetric reference chambers and the medical fluid or dialysate pumped though the disposable cassette. The dialysate is located on the other side of the cassette sheeting from air in communication with the pneumatic source and the volumetric reference chamber. The fluid temperature needs to be about that of the human body, e.g., about 37° C. The air in the reference chamber therefore should be about 37° C.

The system in one embodiment provides a heater at the cassette interface, which heats the interface plate, the volumetric reference chambers and the pneumatic passageways to a single temperature to stabilize the entire pneumatic circuit at a desired temperature. The heated interface plate also enables the reference chambers to be brought to temperature more quickly, especially on cold days. A quick warm-up also saves a substantial amount of time during the calibration of the system. The interface plate in one embodiment is made entirely of metal, which can be heated. Alternatively, a cassette interface portion of the manifold, to which pneumatic control valves controlling pressure to the fluid valves are attached, is plastic. The reference chambers are metal and are provided in a module with a heating element, such as a resistive heating element. The module is affixed to the plastic interface. The interface includes pump chamber walls having a metal or thermally conductive section. Heat is thereby transferred to the pump chamber interface wall, which heats air therein.

It is therefore an advantage of the present disclosure to provide an improved medical fluid system, such as for APD, HD, HF, HDF and CRRT.

It is another advantage of the present disclosure to provide a medical fluid system having a rotatable base, making device features readily accessible.

Moreover, it is an advantage of the present disclosure to provide a medical fluid system that is relatively mobile and that carries the supply bags as the system is moved.

It is a further advantage of the present disclosure to provide a medical fluid system that positions fluid supply bags so as to tend to trap air in the bags.

Another advantage of the present disclosure is to provide a non-invasive temperature sensing apparatus and method.

It is yet a further advantage of the present disclosure to provide a disposable cassette wherein at least one of: (i) the cassette includes three pumping chambers; and (ii) the molded plastic part of the cassette is provided inside a pouch made of flexible sheeting sealed together and to tubing attached to the molded plastic part.

It is still another advantage of the present disclosure to provide a method and apparatus for real time measurement of fluid volume pumped.

Further still, it is an advantage of the present disclosure to provide a fluid management system ("FMS"), which has improved temperature control for a fluid volume measuring system using the ideal gas law.

Yet another advantage of the present disclosure is to provide for improved leak detection in a pneumatically actuated pumping system.

Still further, it is an advantage of the present disclosure to provide an improved cassette/manifold membrane gasket.

Yet a further advantage of the present disclosure is to provide an auto-connection mechanism for solution lines and an auto-identification mechanism to ensure that a proper solution at a proper volume for a particular supply bag will be delivered to a patient.

Still a further advantage of the present disclosure is to provide an improved priming technique using a dual lumen patient line and an apparatus and method for automatically connecting the dual lumen patient line to a dual port transfer set.

Further still, an advantage of the present disclosure is to provide an apparatus and method for automatically detecting whether a solution bag has been loaded for therapy.

A related advantage is to use the above bag detection apparatus and method for automatically detecting whether a multichamber solution bag has been opened properly so that the solution inside is mixed properly for delivery to the patient.

A further related advantage is that the above bag detection apparatus and method is non-invasive, maintaining the sterility of the concentrates and preserving the bag and other solution disposables.

Additional features and advantages are described herein, and will be apparent from, the following Detailed Description and the figures.

BRIEF DESCRIPTION OF THE FIGURES

FIGS. 13A to 13I are perspective views illustrating one embodiment of a supply line auto-connection sequence using the auto-connection mechanism of FIG. 12.

FIG. 16 is a perspective view of one embodiment for a disposable pumping cassette having a rigid portion held in a sealed pump sheeting pouch.

FIGS. 17A and 17B are front and rear views, respectively, of one embodiment of a disposable pumping cassette having three pump chambers.

FIG. 23 is a perspective view of the reverse side of the interface plate of FIG. 21, which is metallic and can include a heating strip for heating the reference chambers formed in the interface plate.

FIG. 24 is a perspective view of a reverse side of an alternative manifold, which includes a plastic interface and control valve connection portion and a heated reference chamber module connected to the plastic portion.

FIGS. 28A to 28F illustrate one embodiment of a real time method for determining volume of fluid moved.

FIG. 29 is a chart of real time fluid volumes calculated via the method of FIGS. 28A to 28F.

FIG. 35 is a schematic illustration of one embodiment of an inductive solution container loading system in a "not mixed" sensing state.

FIG. 36 is a schematic illustration of the system embodiment of FIG. 35 in a "mixed" sensing state.

FIGS. 37A to 37D are schematic views of one embodiment of an inductive sensing system employing multiple emitters and receiving the system capable of orientation detector supply container loading.

DETAILED DESCRIPTION

Mobile Cart System

Figure 1:
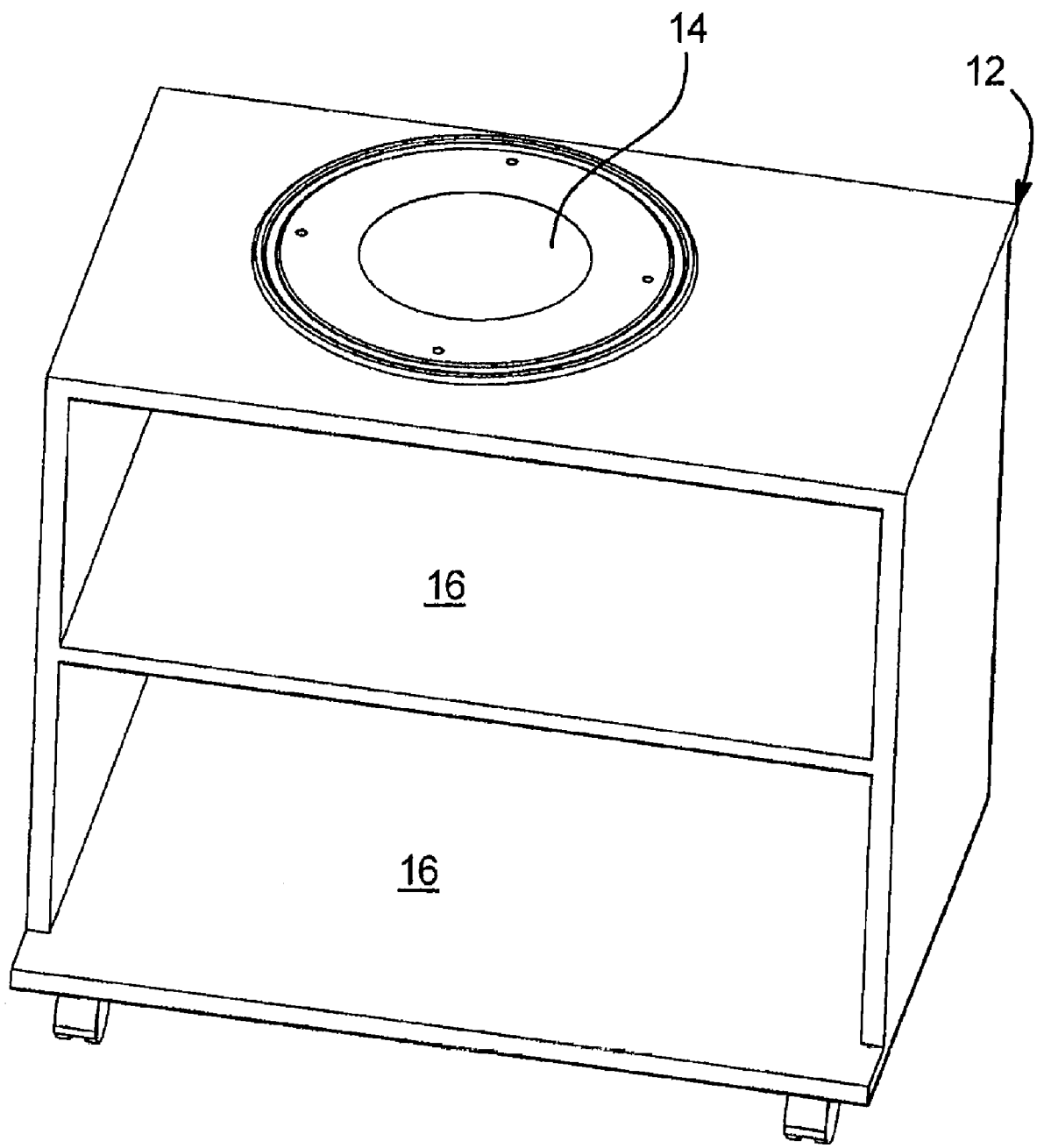
FIG. 1 illustrates one embodiment of a dialysis system cart with a machine holding, rotatable bearing.
Figure 2:
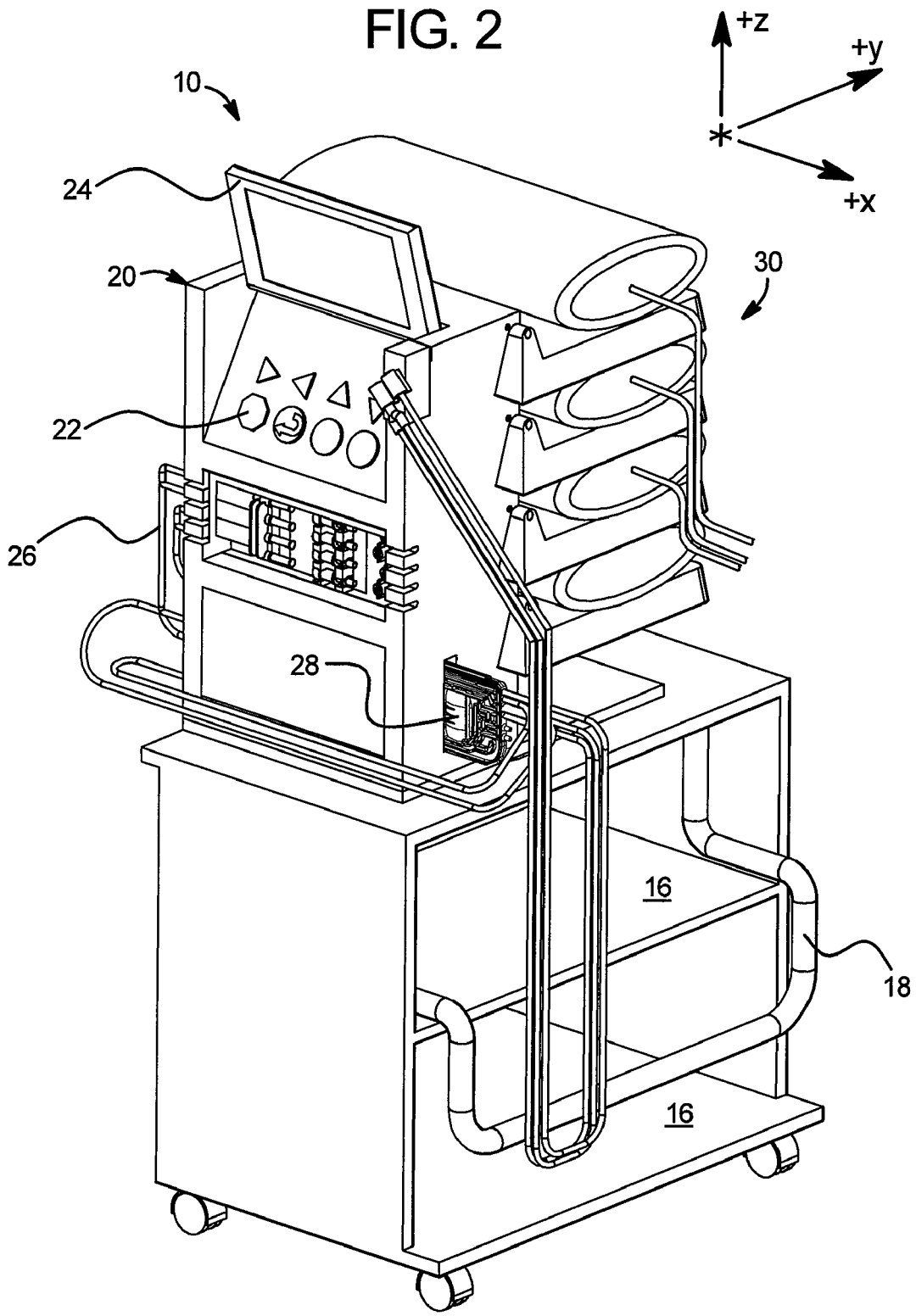
FIG. 2 illustrates the cart of FIG. 1, in which the dialysis machine has been rotated to have the solution bags facing a front of the cart.
Figure 3:
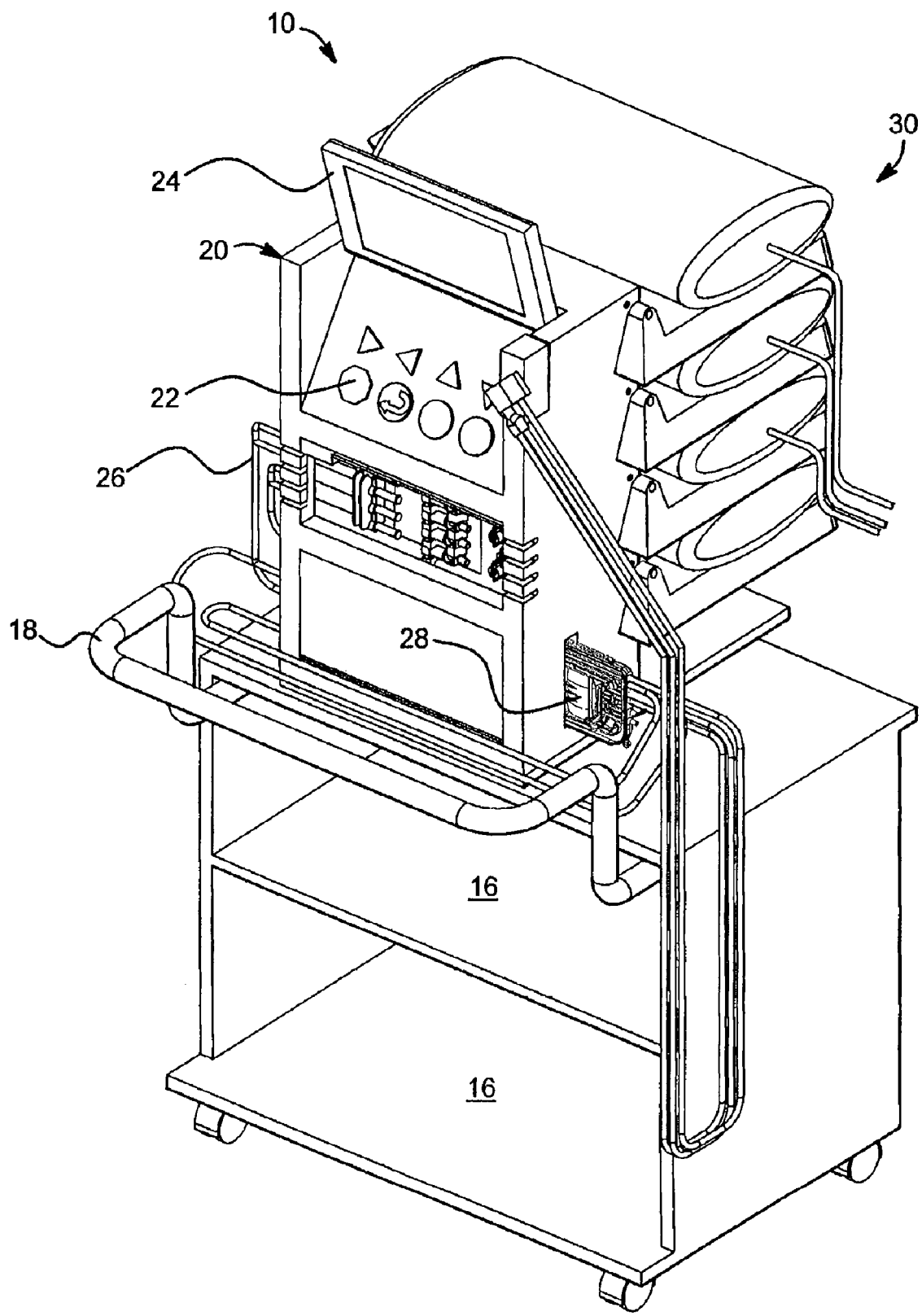
FIG. 3 illustrates a system using the cart of FIG. 1, in which the dialysis machine has been rotated to have machine controls facing a front of the cart.

Referring now to the drawings and in particular to FIGS. 1 to 3, a dialysis system, such as an automated peritoneal dialysis ("APD") system 10 is illustrated. It should be appreciated that system 10 can be used with other types of renal failure therapy systems, such as any of those maintained above.

FIGS. 1-3 illustrate that system 10 includes a mobile cart 12, which allows the system to be moved readily, e.g., from a family room to a bedroom and vice versa. Cart 12 includes a lazy Susan-type bearing 14, which provides ample access to the controls 22 and bag management system 30 of an instrument 20 at all times. Bag management system 30 organizes the loading of supply bags at the beginning of therapy as shown in detail herein. Lazy Susan bearing 14 in one embodiment is equipped with detents that prevent the system from rotating during operation. A cut-out or hole in the center of lazy Susan bearing 14 allows a power cord to pass through to shelves 16 of cart 12. Lazy Susan bearing 14 can also have a total rotation limit, e.g., 360 degrees or so, to prevent damage to the power cord due to over-rotation.

As shown specifically in FIG. 2, instrument 20 can, for example, be rotated to face the patient to provide ready access to the bag management shelves of bag management system 30. As shown specifically in FIG. 3, instrument 20 can then be rotated to provide optimum access to the controls 22, display 24, auto-connection mechanism 26 and cassette loading mechanism 28 during the set-up procedure Also, instrument 20 can be rotated so that the display 24 and controls 22 face the patient's bed when the patient is asleep. Here, if an alarm sounds, the patient can potentially access controls 22, drain line, supply bags lines, etc., without getting out of bed.

Mobile cart 12 includes shelves or drawers 16, which hold the ancillary supplies needed for dialysis therapy. To move system 10, the patient needs to unplug a power cord. Mobile cart 12 accommodates the drain bag, e.g., on lower shelf 16. The self-contained drain cart allows cart 12 to be moved without having to first load the drain bag. If a drain line is run to a house drain instead of a bag, the drain line likely has to be removed from the drain and placed onto cart 12 when system 10 is moved. A handle 18 facilitates moving system 10 and in one embodiment can be rotated upwardly for movement of cart 12 and downwardly and out of the way when not needed.

Bag Management System

Referring now to FIGS. 4 to 9, an embodiment for bag management system 30 of dialysis system 10 is illustrated. As illustrated, bag management system 30 is connected to or made integral with instrument or cycler 20. Bag management system 30 as illustrated is configured for four, e.g., six liter supply bags 40a to 40d (referred to herein collectively as supply bags 40 or generally, individually as supply bag 40). System 30 is configured alternatively to hold more or less six liter bags 40. FIGS. 4 to 9 also show that cycler 20 includes a hinged display 24, which can operate with separate controls 22 and/or a touch screen overlay.

Figure 4:
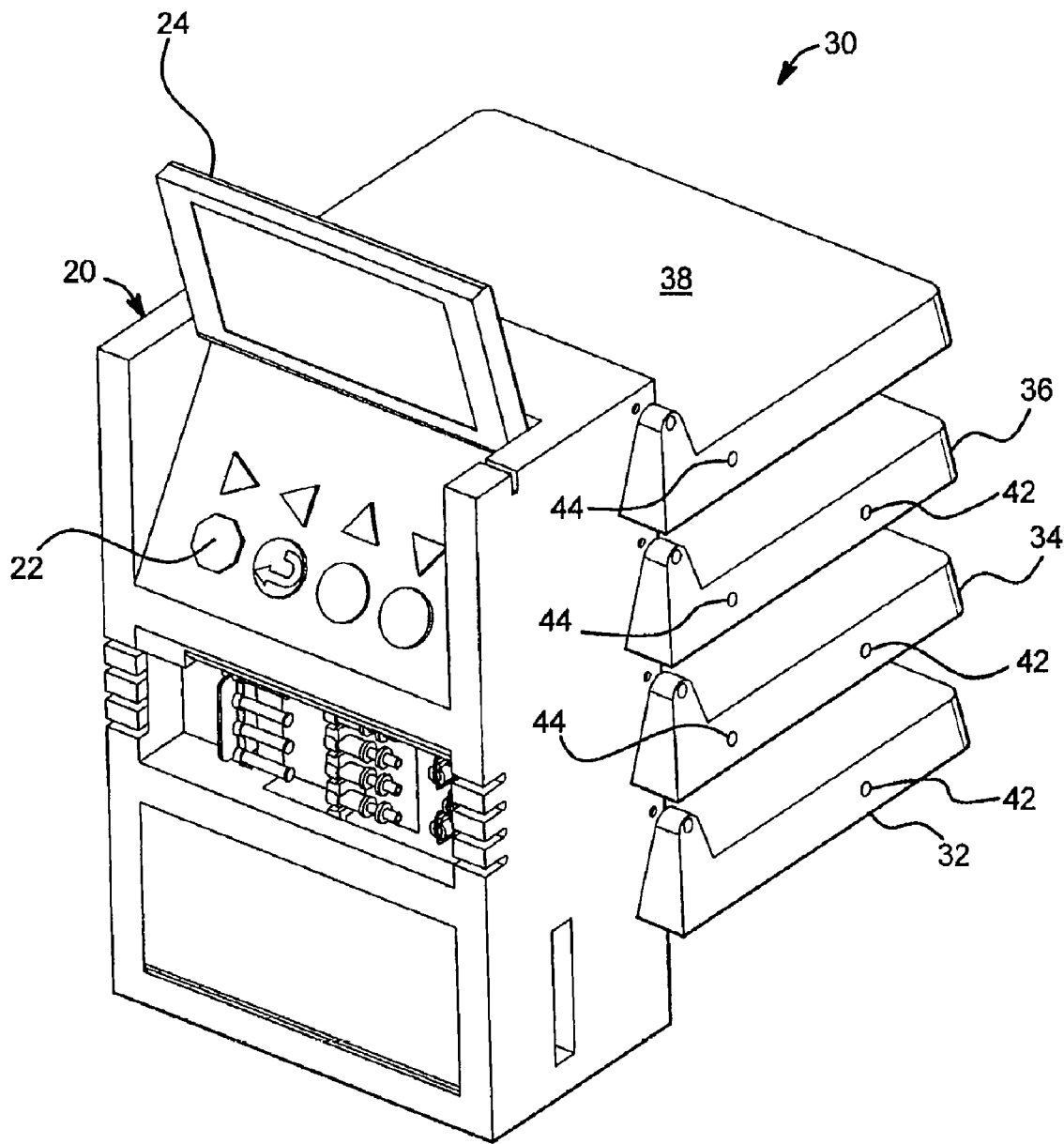
FIGS. 4 to 9 illustrate one embodiment for a supply bag loading procedure for a bag management system of a dialysis system of the present disclosure.
Figure 5:
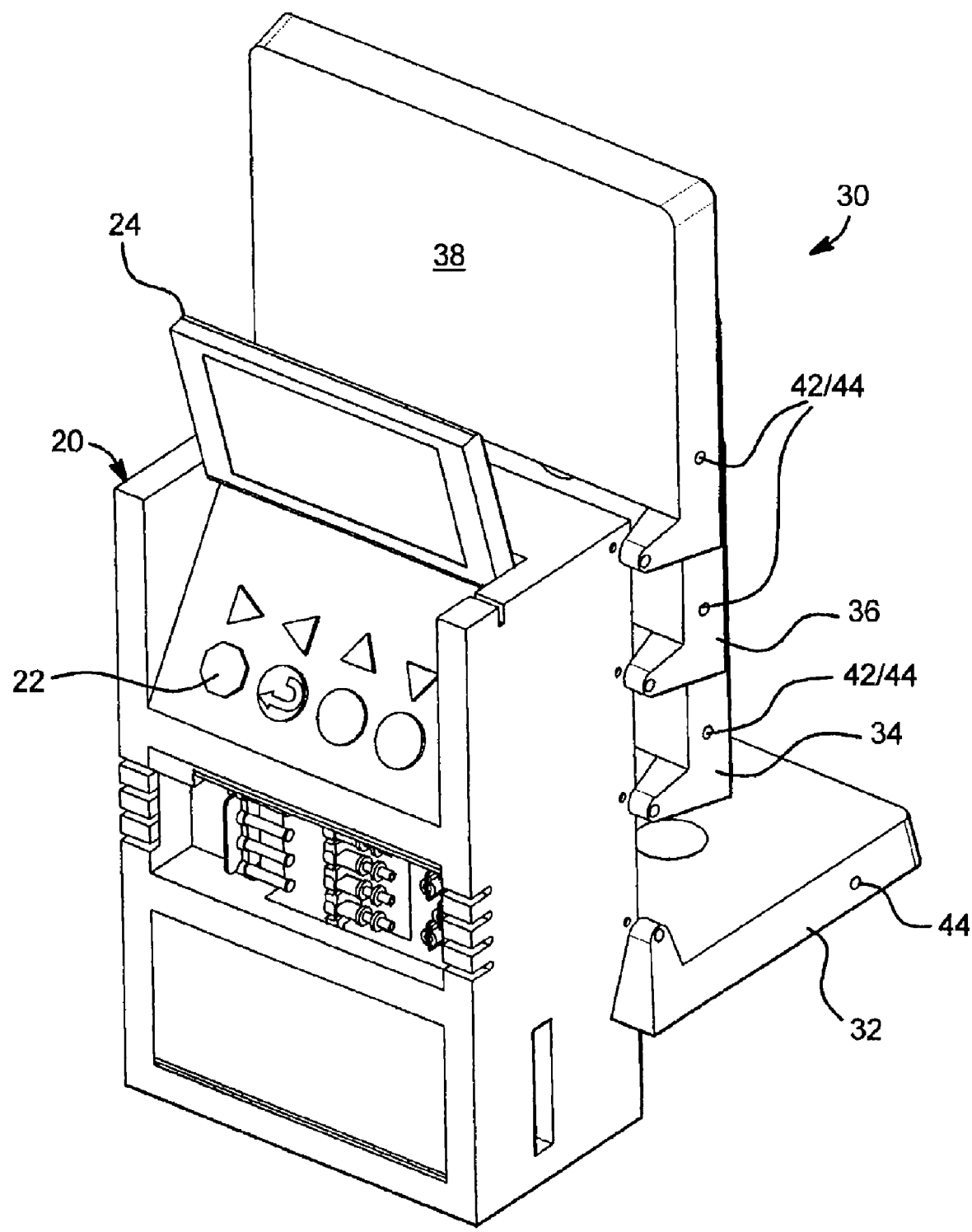

FIG. 4 shows bag management system 30 with each of shelves 32, 34, 36 and 38 rotated down and no supply bags 40 loaded. FIG. 5 shows bag management system 30 with lower shelf 32 folded down and shelves 34, 36 and 38 rotated upwardly and out of the way to provide access to bottom shelf 32. In an embodiment, the shelves are configured in a cascading or telescoping manner such that third shelf 36 can fold or rotate into upper shelf 38, second shelf 34 can fold or rotate into third shelf 36 and lower shelf 32 can fold or rotate into second shelf 34. The hinges of the shelves can have releasably interlocking apparatuses (e.g., mating tabs and detents) that hold the shelves releasably in place when folded or rotated upwardly. Alternatively or additionally, the shelves can releasably lock one to another, e.g., third shelf 36 locking to upper shelf 38, second shelf 34 locking to third shelf 36, and so on. For example, interlocking tabs and detents 42 and 44, respectively, are provided at the sides or gussets of the shelves so that the locking mechanisms 42 and 44 do not interfere with the bags 40 when loaded.

Figure 6:
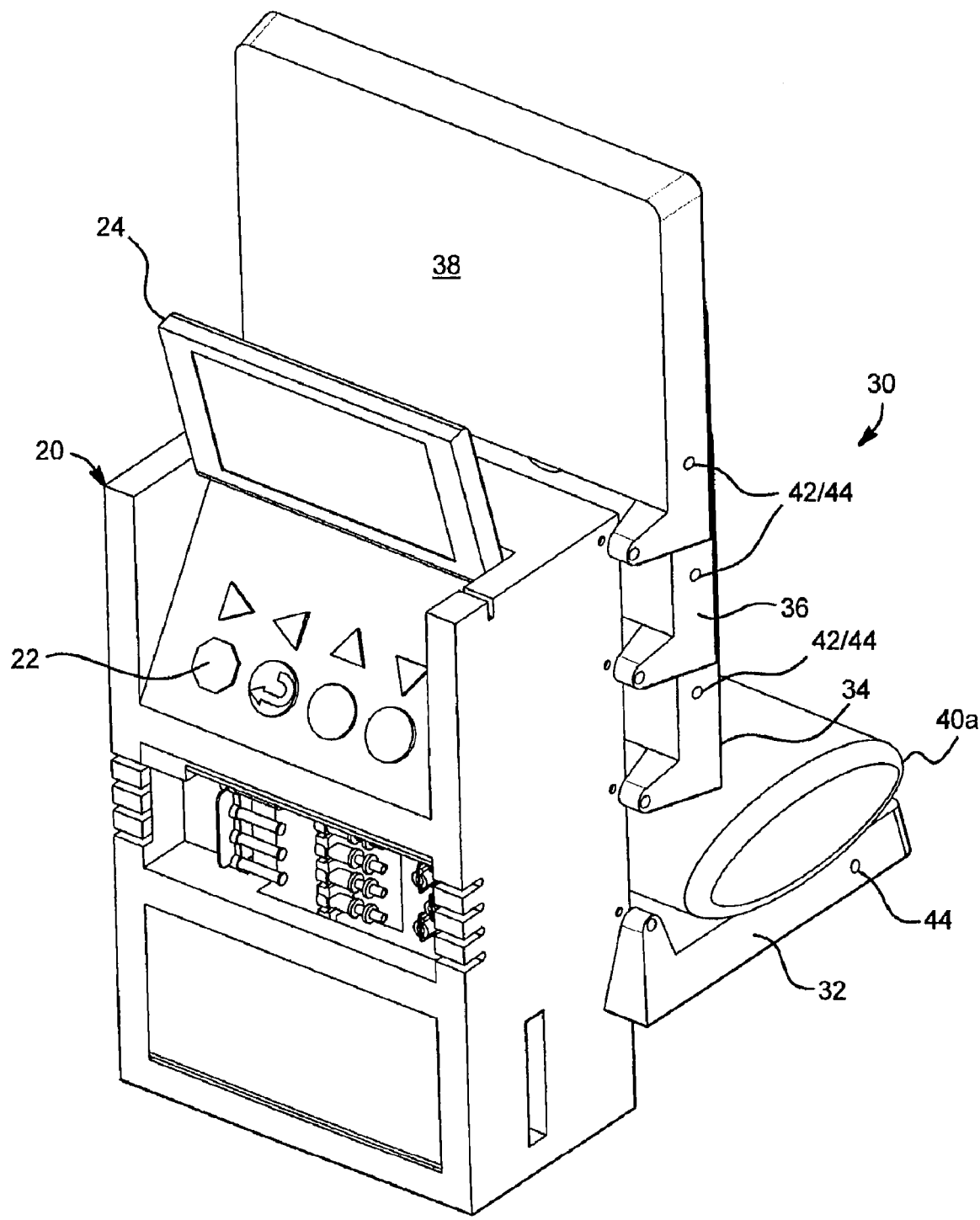
Figure 7:
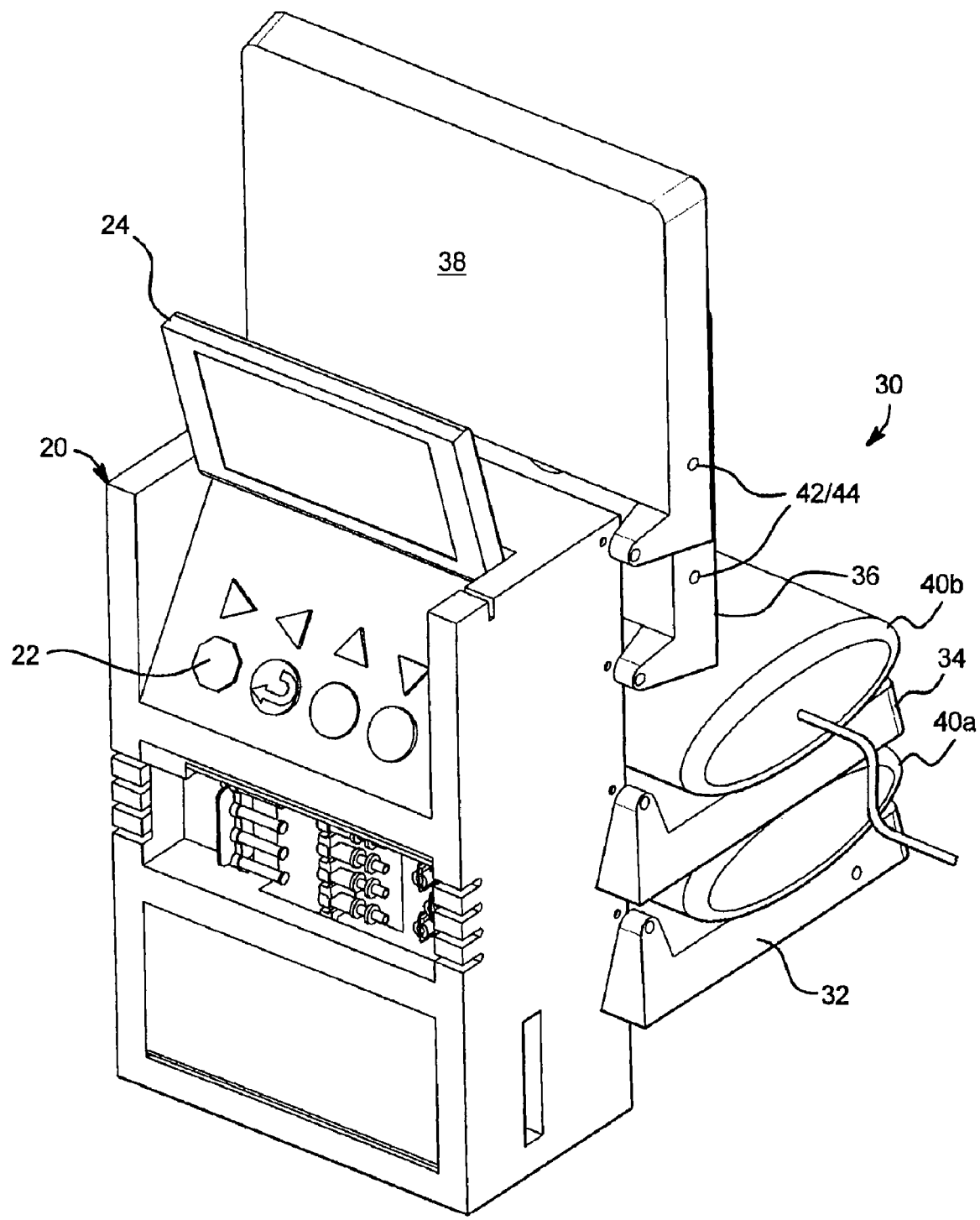

FIG. 6 shows bag management system 30 with lower shelf 32 folded down, a first supply bag 40a loaded onto lower shelf 32, and shelves 34, 36 and 38 hinged upwardly and out of the way. FIG. 7 shows bag management system 30 with lower shelf 32 and second shelf 34 folded down, first supply bag 40a loaded onto lower shelf 32, a second supply bag 40b loaded onto second shelf 34, and shelves 36 and 38 hinged upwardly and out of the way.

Figure 8:
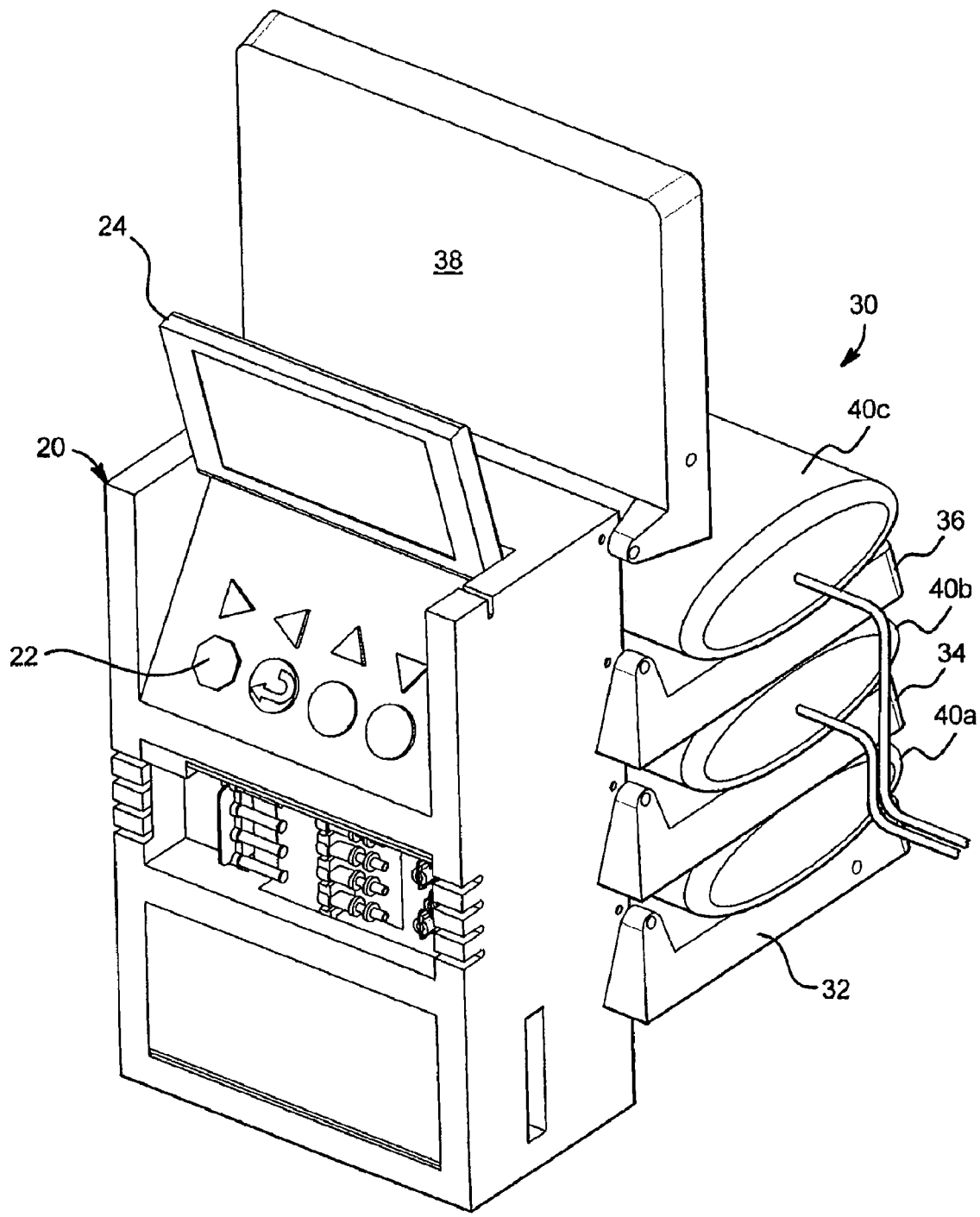
Figure 9:
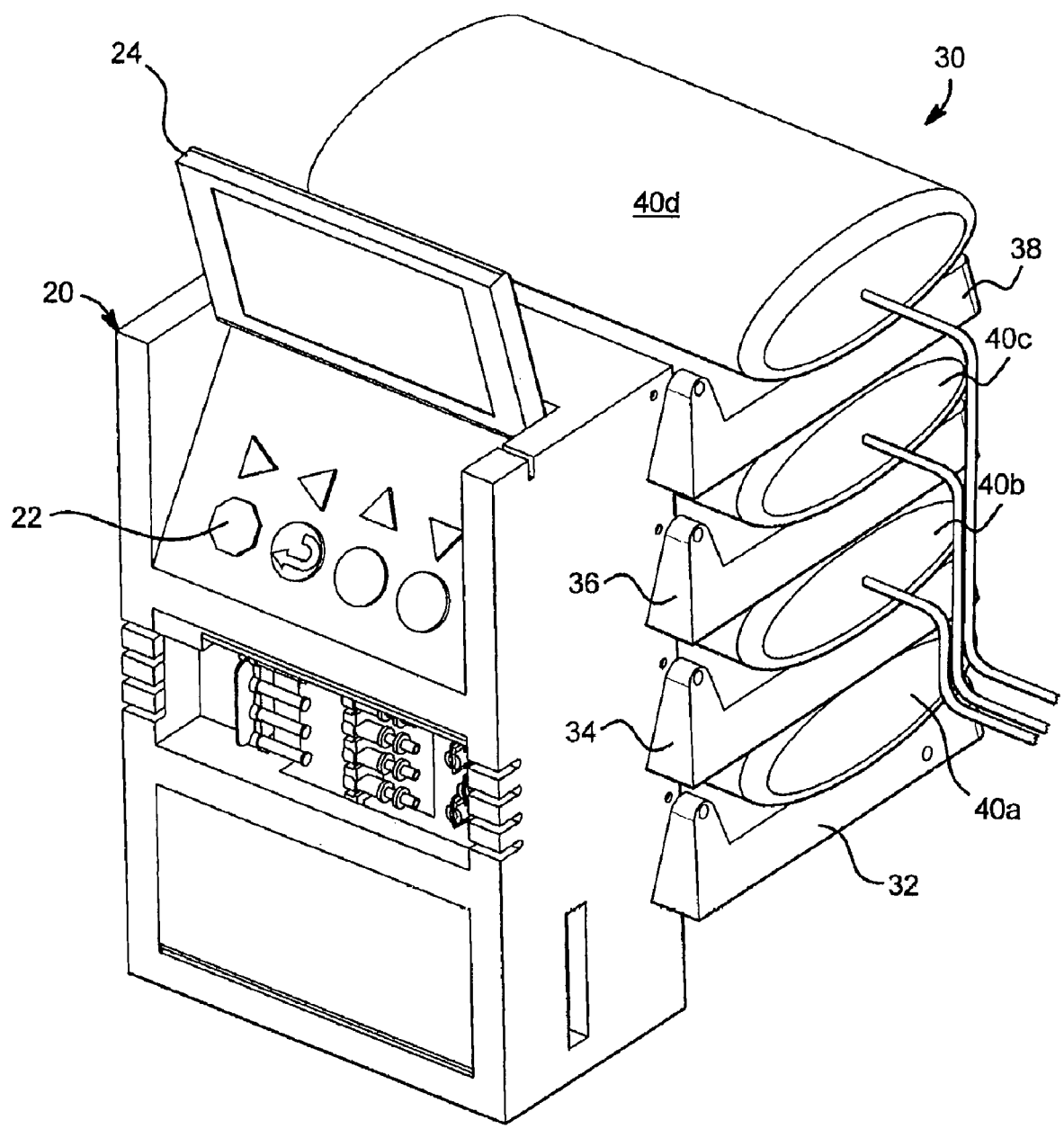

FIG. 8 shows bag management system 30 with lower shelf 32, second shelf 34 and third shelf 36 folded down, first supply bag 40a loaded onto lower shelf 32, second supply bag 40b loaded onto second shelf 34, a third supply bag 40c loaded onto third shelf 36, and shelve 38 hinged upwardly and out of the way. FIG. 9 shows bag management system 30 with lower shelf 32, second shelf 34, third shelf 36 and top shelf 38 all folded down, first supply bag 40a loaded onto lower shelf 32, second supply bag 40b loaded onto second shelf 34, third supply bag 40c loaded onto third shelf 36, and fourth supply bag 40d loaded onto top shelf 38.

Each tray in the bag management system 30 folds up providing easy access to the shelf below. When used with cart 12 above, system 30 minimizes the height to which patients have to lift the solution bags. The shelf holds solution bags 40 elevationally above a heater, which can be located at the bottom of instrument 12 for example, and orients the bag so that the bag outlet port resides below the rest of the bag. The configuration causes dialysis fluid to flow from the bags until empty, leaving any air trapped in the empty bags. This shelf configuration, bag placement and orientation can enhance the volumetric pumping speed and accuracy of the fluid delivery pumps when fluid is pumped directly from the supply bags, e.g., through an inline heater, and into the patient since air does not flow downhill, e.g., from a bag 40 into a pumping chamber of cassette 28.

One or more or all of shelves 32 to 38 can employ a sensor operable with a sensing system stored in memory. The sensor and associated system perform multiple functions. One function is to determine if a dual chamber or multiple chamber bag has been opened to allow two or more concentrates to mix to form a dialysis fluid that can be pumped to the patient. Sensing a properly opened bag can be a prerequisite for the pumps and/or valves or occludes to operate. The sensors can also detect which shelves 32 to 38 have bags and which do not and thus whether enough fluid has or can be connected. One suitable sensor and associated system is found in copending patent application Ser. No. 11/773,501, filed Jul. 5, 2007, entitled, "Apparatus and Method For Verifying A Seal Between Multiple Chambers", assigned for the eventual assignee of the present disclosure, the entire contents of which are hereby incorporated by reference and relied upon. An alternative inductive sensing apparatus and method is discussed below beginning at FIG. 35.

Disposable Set

Figure 10:
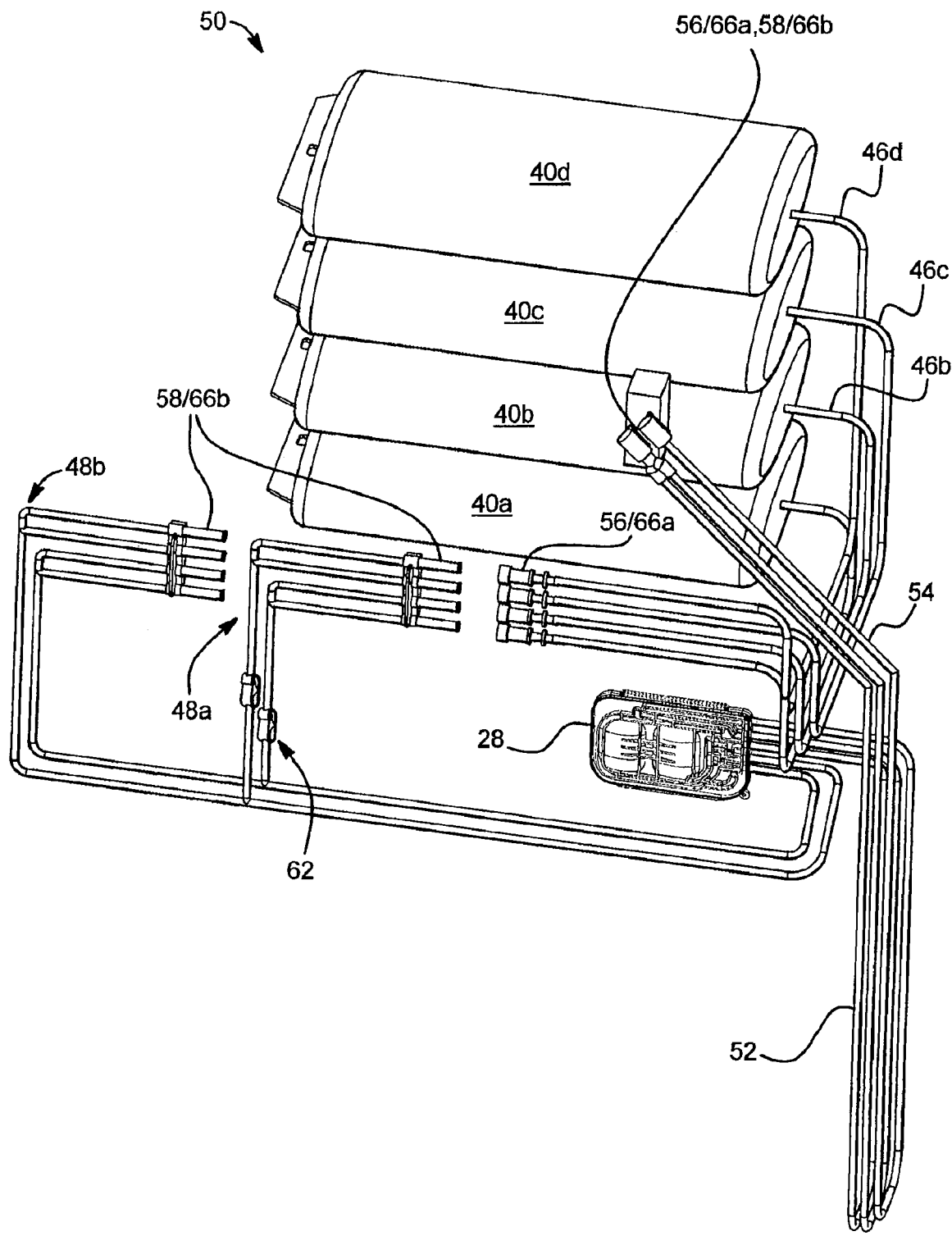
FIG. 10 is a perspective view of one embodiment of a disposable set of the system of the present disclosure.
Figure 11:
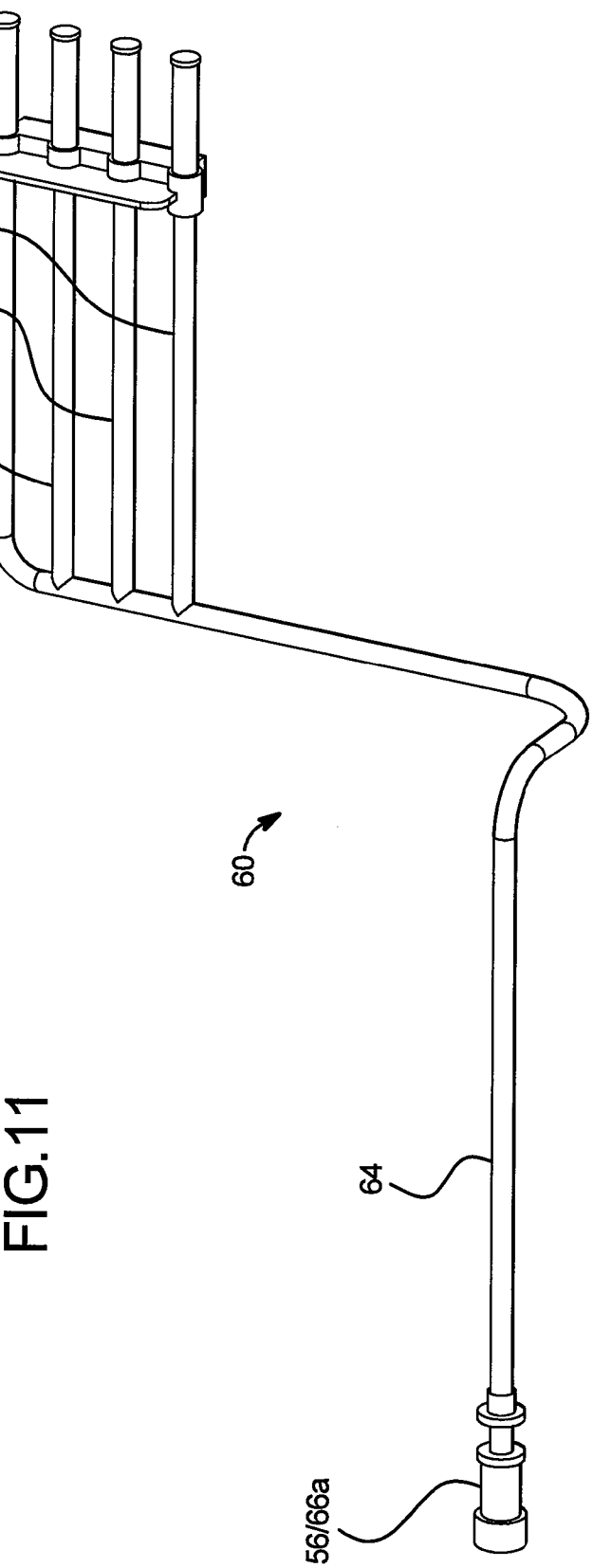
FIG. 11 is a perspective view of one embodiment of a four-to one manifold useable with the disposable set of FIG. 10.

Referring now to FIGS. 10 and 11, an embodiment of a disposable set 50 for system 10 is illustrated. FIG. 10 illustrates that disposable set 50 includes disposable cassette 28 and supply bags 40 as discussed above. Bags 40 in an embodiment each include a solution line or pigtail 46a to 46d (referred to herein collectively as pigtails 46 or generally, individually as pigtail 46), which connect to a first set of supply lines 48a. Solution lines or pigtails 46 in one embodiment terminate in female connectors 56 protected by tip protector 66a. Connectors 56 in one embodiment are female connectors protected by a pierceable cover. Disposable set 50 can include a second set of supply lines 48b for a high-volume therapy as discussed below. First and second supply line sets, 48a and 48b respectively, each include multiple lines ending in a connector 58 protected by a tip protector 66b. Connectors 58 can be male spike connectors that spike through the protective covers of female connectors 56 of bag lines 46.

Disposable set 50 also includes a patient line 52 and drain line 54. Patient line 52 can be a dual lumen line in which one line terminates in a pierceably sealed female connector 56 protected by a tip protector 66a and the other line terminates in a spike connector 58 protected by a tip protector 66b (see FIGS. 15A to 15D). Drain line terminates in one embodiment with a spike receptacle less a septum, so that a supply bag cannot be connected to the drain line.

Pigtails 46 in one embodiment terminate in female connectors 56 protected by tip protector 66a. Connectors 56/tip protectors 66a are held together in a single organizer in one embodiment. Patient line 52 can be a single lumen patient line (batch dialysis) or a dual lumen patient line (for batch or continuous dialysis) as desired. The first set of supply lines 48a, patient line 52 and drain line 54 are each connected to cassette 28.

FIG. 10 further illustrates one embodiment for a high volume disposable set (e.g., eight bags), which is provided by teeing a second set of supply lines 48b off of the first set of supply lines 48a (connected to cassette 28) and providing an organizer for holding four spike connectors 58 on the end of each supply line 48a or 48b. The spikes and organizers can be integrated into a single molded spike bundle that contains the spikes and features for gripping and holding the bundle during set up and operation. Each spike connector 58 of each supply line can connect fluidly and sealingly with a female connector 56 at the end of each supply bag pigtail 46. As mentioned, each spike connector 58 is protected by its own tip protector 66b. Line clamps 62 are provided on the first set of supply lines 48a. The clamps can be used to occlude the first set of supply lines 48a before an auto-connection mechanism (discussed below) disconnects connectors 58 of the first set of supply lines 48a from connectors 56 at the end of pigtails 46. The auto-connection mechanism can then connect the second set of supply lines 48b to a second set of supply bags 40 (not illustrated).

FIG. 11 illustrates a second embodiment for producing a high-volume disposable set 50. Here, the first set of supply tubes 48a is converted to a high volume set via four-to-one manifold 60. Four-to-one manifold 60 in one embodiment has at one end the same organizer holding four lines 48c terminating in spike connectors 58/tip protectors 66b as that described above for the supply lines 48a and 48b. Manifold 60 can therefore itself be connected to up to four supply bags 40. A connector 56/tip protector 66a of a single input line 64 from four-to-one manifold 60 is then inserted into the auto-connection mechanism (described below) in lieu of the connector 56/tip protector 66a at the end of pigtail 46 of a single supply bag 40. An auto-identification system described below automatically tracks the number of bags connected to each four-to-one manifold 60 and the volume of the solution that has been connected. Disposable set 50 using manifold 60 can operate with up to sixteen, e.g., six liter, bags of solution.

Auto-Connection

Figure 12:
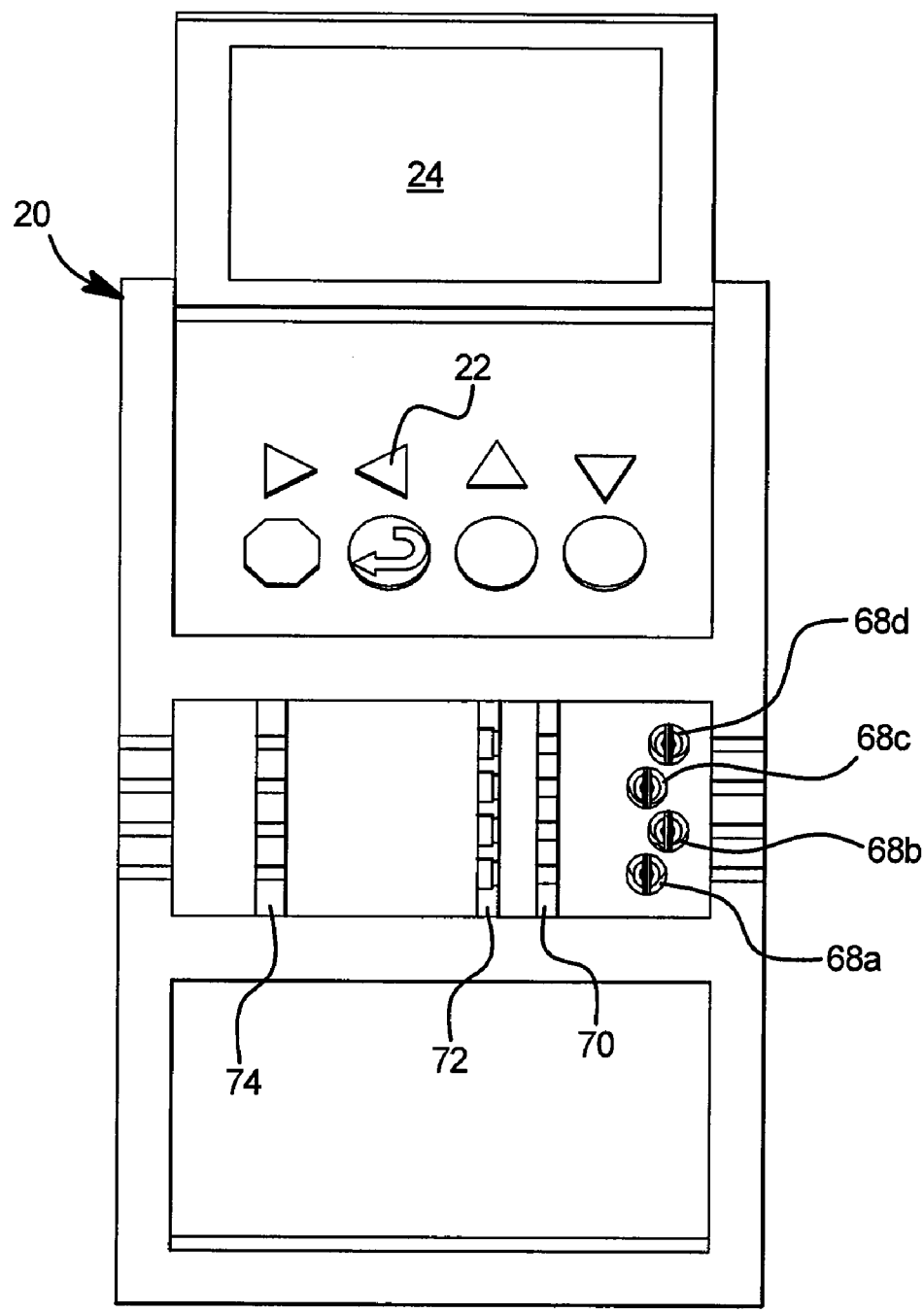
FIG. 12 is a perspective view of one embodiment of an instrument of the system of the present disclosure, which includes an auto-connection mechanism operable with the disposable set of FIG. 10.

Referring now to FIG. 12, instrument 20 in an embodiment includes pinch clamps or pinch valves 68a to 68d (referred to collectively herein as valves 68 or individually as valve 68), one valve 68 for each pigtail 46a to 46d of supply bags 40a to 40d, respectively (or manifold line 64 of four-to-one manifold 60). Valves 68a to 68d are positioned to hold and occlude pigtails 46a to 46d, respectively, when (i) connectors 56 at the end of the pigtails 46 are attached to a stationary connector holder 70 and (ii) the tip protectors 66a protecting each connector 56 are attached initially to a tip protector removal carriage 72 of the auto-connection mechanism. Tip protector removal carriage 72 is also configured to remove spike connector 58 tip protectors 66b as shown below. Valves 68 are opened, e.g., sequentially, to allow fluid to be withdrawn sequentially from supply bags 40. Valves 68 in an embodiment are closed automatically if there is a need to reload cassette 28 after supply bags 40 have been connected. Stationary holder 70 holds supply bag pigtail connectors 56 stationary during the auto-connection process.

FIG. 12 also illustrates a moveable connection carriage 74, which holds the organized spike connectors 58/tip protectors 66b at the end of supply lines 48a connected to cassette 28. The individual holders of stationary holder 70 and moveable carriages 72 and 74 are aligned in the Z-direction as shown by the coordinate system in FIG. 12.

Moveable carriage 72 moves in the +X and −X directions to remove tip protectors 66a from connectors 56 and tip protectors 66b from spike connectors 58. Moveable carriage 72 also moves in the +Y and −Y directions to pull the removed tip protectors 66a and 66b out of the way for line connection and possibly to reload the tip protectors. Moveable carriage 72 in an embodiment uses an XY gantry system, which includes a pair of lead screws each driven by a motor, such as a stepper motor. For example, moveable carriage 72 can be threaded and receive a ball screw supported on two ends by bearings and driven by a stepper motor to move carriage 72 back and forth in a precise manner in the +X and −X directions. That X-direction assembly can in turn be threaded, e.g., at a bearing support, and receive a ball screw supported on two ends by bearings and driven by a stepper motor to move the X-direction assembly (including carriage 72) back and forth in a precise manner in the +Y and −Y directions.

Moveable carriage 74 moves in the +X and −X directions to push spike connectors 58 of cassette supply lines 48a into sealed communication with pierceably sealed female connectors 56 of bag pigtails 46. Here, moveable carriage 74 can be threaded and receive a ball screw supported on two ends by bearings and driven by a stepper motor to move carriage 74 back and forth in a precise manner in the +X and −X directions.

System 10 is computer controlled and can for example include master processing and memory operating with delegate controllers including delegate processing and memory. Master processor and memory can also operate with a safety controller having safety processing and memory. In one embodiment, master processing and memory operates with a delegate motion controller having processing and memory (e.g., programmable or via an application specific integrated circuit ("ASIC")), which outputs to the stepper motors and receives inputs, e.g., positional inputs from position sensors.

Referring now to FIGS. 13A to 13J, an auto-connection sequence for the sealed mating of connectors 56 of pigtails 46 of supply bags 40 to the spike connectors 58 of the supply lines of set 48a (alternatively supply line set 48b and 48c as discussed above) of cassette 28 is illustrated. In FIG. 13A, an organizer holding four spike connectors 58/tip protectors 66b of cassette supply line set 48a connected to cassette 28 are loaded into the group holder of moveable carriage 74. Alternately, an integrated four-spike bundle with connectors 58/tip protectors 66b is loaded into the group holder of moveable carriage 74. In this step, cassette 28 is also loaded into instrument 20 (see FIGS. 2 and 3).

In FIG. 13B, connectors 56/tip protectors 66a located at the end of four supply bag pigtails 46 are loaded into individual holders of stationary holder 70 and moveable carriage 72. In particular, connectors 56 are loaded into individual holders of stationary holder 70 and tip protectors 66a are loaded moveable carriage 72. Thus in FIG. 13B, tip protectors 66a and 66b are set to be removed automatically from connectors 56.

After spike connectors 58/tip protectors 66b and connectors 56/tip protectors 66a have been loaded into the auto-connection mechanism, a cover or door is closed (not illustrated), isolating holder 70, carriages 72 and 74, spike connectors 58/tip protectors 66b and female connectors 56/tip protectors 66a from the environment. System 10 then injects filtered high-efficiency-particulate-air ("HEPA") or ultra-low-penetration-air ("ULPA") into the sealed compartment to reduce the bioburden in the region prior to tip protector removal from connectors 56 and 58. Pneumatic control of HEPA or ULPA air can be located on the motion controller mentioned above or on a separate pneumatic controller operating with the master controller.

The imaging system determines which supply bags have been loaded (quantity, size, solution type, expiration date, lot code, etc.) and alerts the user if a problem arises with any of the above identifiers. For example, the solution volume may be insufficient to perform the selected therapy. Alternatively, a connector may be distorted or damaged so that it will not connect properly.

In FIG. 13C, moveable carriage 72 moves in the −X direction (according to coordinate system of FIG. 12) to remove pre-loaded tip protectors 66a from supply bag connectors 56.

In FIG. 13D, moveable carriage 72 moves further in the −X direction (according to coordinate system of FIG. 12) to lock tip protectors 66b to protecting spike connectors 58.

In FIG. 13E, moveable carriage 72 moves in the +X direction (according to coordinate system of FIG. 12) to remove tip protectors 66b from spike connectors 58.

In FIG. 13F, moveable carriage 72 moves in the +Y direction (according to coordinate system of FIG. 12) to move out of the way of supply bag connectors 56 and spike connectors 58.

In FIG. 13G, moveable carriage 74 moves in the +X direction (according to coordinate system of FIG. 12) towards stationary holder 70 to push spike connectors 58 into pierceably-sealed supply bag connectors 56 and to fluidly connect supply bag 40 to cassette 28. After the connections of spike connectors 58 to supply bag connectors 56 have been made, an imaging system described below verifies that the connections have been made properly and that no leaks are present.

FIG. 13H(a) shows one removal embodiment in which a connected supply of set lines 48a and solution lines or pigtails 46 and associated empty supply bags 40 and cassette 28 are removed from carriage 74 and holder 70, respectively, together. In FIG. 13I, moveable carriage 72 is then moved in the −Y direction (FIG. 12) to allow the consumed tip protectors 66a and 66b to be retrieved.

FIG. 13H(b) shows another removal embodiment in which moveable carriage 74 moves in the −X direction to pull connectors 56 and 58 apart, after which moveable carriage 72 moves in the −Y direction (according to coordinate system of FIG. 12) and then back and forth in the + and −X directions to reattach tip protectors 66a and 66b to connectors 56 and 58, respectively, allowing supply lines of set 48a, pigtails 46 and associated supply bags 40 and cassette 28 to be removed from carriages 72 and 74 and holder 70, respectively. This latter removal method is preferable if it is common that the supply bags will not be completely empty when the bags have to be removed.

Auto-Identification

Figure 14:
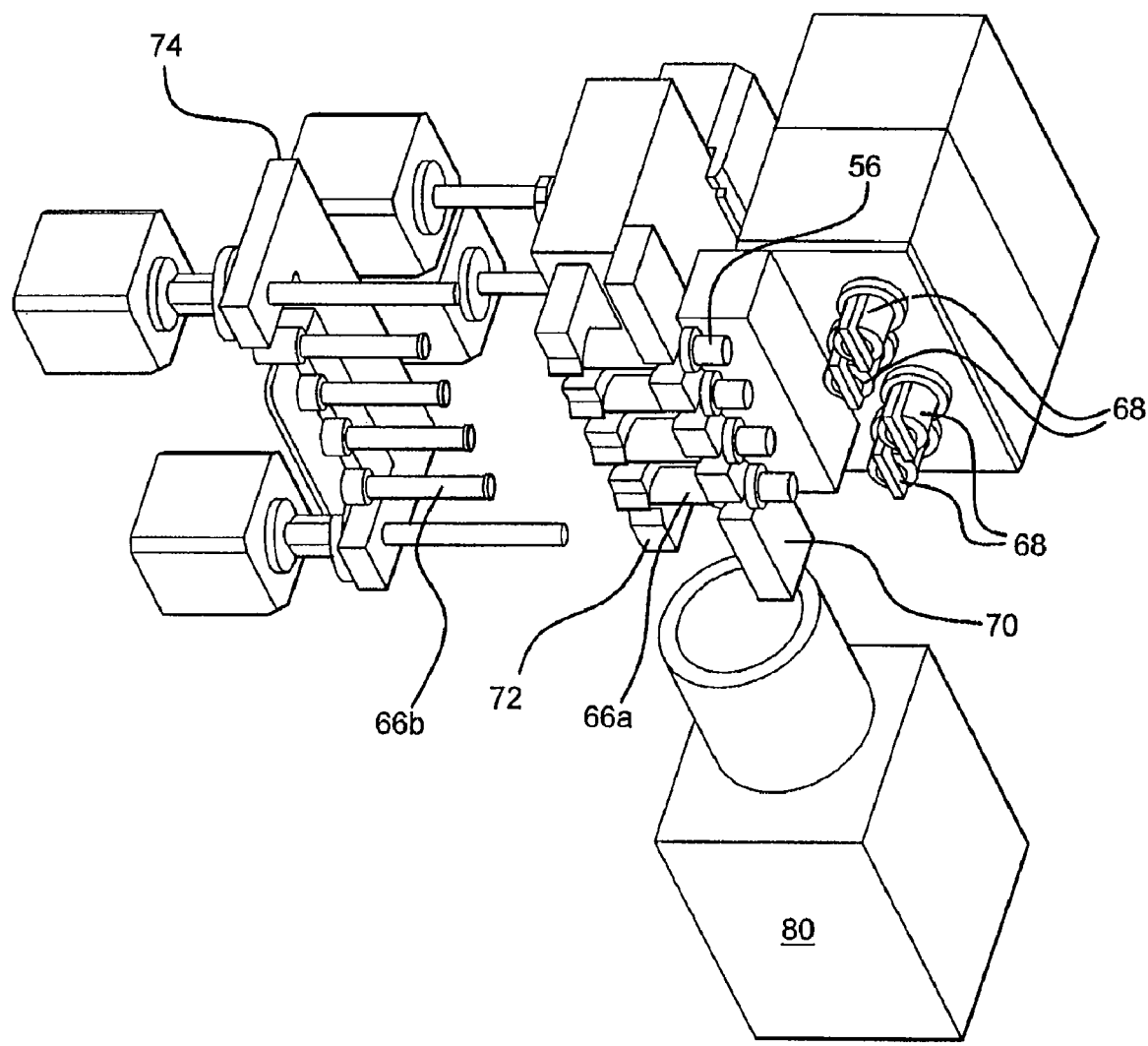
FIG. 14 is a perspective view of one embodiment of an auto-identification mechanism operable with the auto-connection mechanism of FIG. 12.

FIG. 14 illustrates one embodiment for an auto-identification system. The system includes a color-capture device ("CCD") camera 80, which uses a charge-coupled device image sensor and an integrated circuit containing an array of linked, or coupled, light-sensitive capacitors. Other cameras that create a three-dimensional image of a connection area shown in FIG. 14 may be used alternatively. The auto-identification system uses the image from camera 80 to determine characteristics of solution bags 40 and to verify that the correct, undamaged connectors 56 and 58 are loaded into the mechanism.

The auto-identification system accomplishes solution identification via a character recognition routine (located for example on the motion controller or a separate video controller operable with the central processing unit or master controller) that "reads" the codes printed on the pigtail connectors 56 connected to supply bags 40. The "codes" provide (i) solution type, e.g., glucose or bicarbonate concentrate or premixed dialysate, (ii) bag volume, e.g., six liters, and (iii) number of bags per connector 56, e.g., single bag or multiple bags via four-to-one manifold 60. The image of each connector 56 is compared against stored images of the range of acceptable geometries for connector 56. A deformed connector, or a connector that has been loaded incorrectly, or that does not match therapy prescription will fall outside of a range of acceptable geometries and cause system 10 to signal an alarm and cause other appropriate action, e.g., closing clamps 68 or not allowing them to be opened until the alarm is cleared. The imaging system also verifies that the "connected" joints fall within an acceptable range of geometries for a good joint connection. If a joint leaks and droplets form, the imaging system sees the droplets and causes an alarm.

Priming

In an embodiment, a dual lumen patient line 52 (FIG. 10) is used. One lumen is connected to a patient-drain port through a pumping chamber of disposable cassette 28. The other lumen is connected to a patient-fill port through a different pumping chamber of the disposable cassette 28. During priming of the patient line, the two lumens of the patient line are connected together. Cycler 20 causes one of the diaphragm pumps of cassette 28 to pump or push fresh fluid out the patient-fill port on the disposable cassette 28, down one lumen of patient line 52, until it reaches the end of the patient line. The fresh fluid is then pumped back up the other lumen of patient line 52, into cassette 28 through the patient-drain port and into another diaphragm pump of cassette 28, which removes air that the fluid pushes through the patient line 52. When fluid fills the second pump chamber, the patient line is fully primed.

Patient Connection/Disconnection

Primed dual lumen patient line (with fill lumen 52*a* and drain lumen 52*b* connected) and transfer set 82 (with fill line 84 and drain line 86 connected) are loaded into a patient line auto-connection device 90, as illustrated in FIGS. 15A to 15E. Device 90 can be separate from or integrated into instrument 20. Instrument 20 or cart 12 in an embodiment provides an area and apparatus for storing device 90. Device 90 can be powered or configured for manual or manual/automatic operation. Device 90 includes a stationary portion 92 and a portion 94, which is rotatable and translatable with respect to stationary portion 92.

Figure 15A:
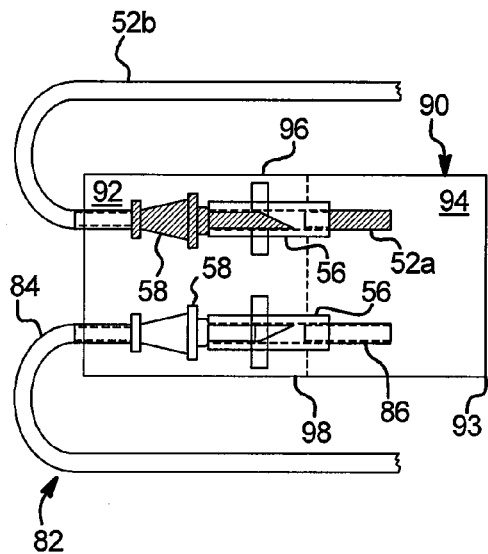
FIGS. 15A to 15E illustrate one embodiment of a patient line auto-connection sequence using the auto-connection mechanism of FIG. 12.
Figure 15B:
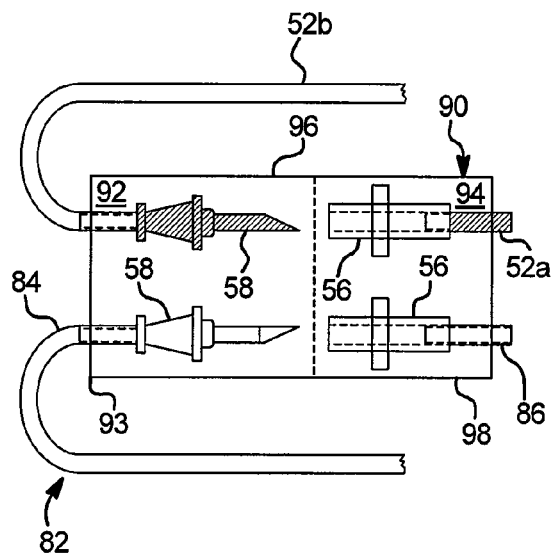
Figure 15C:
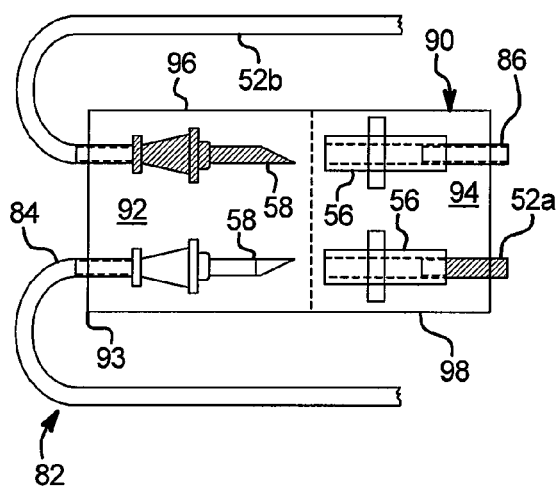
Figure 15D:
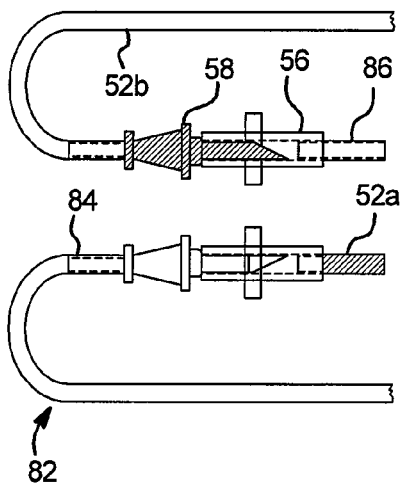
Figure 15E:
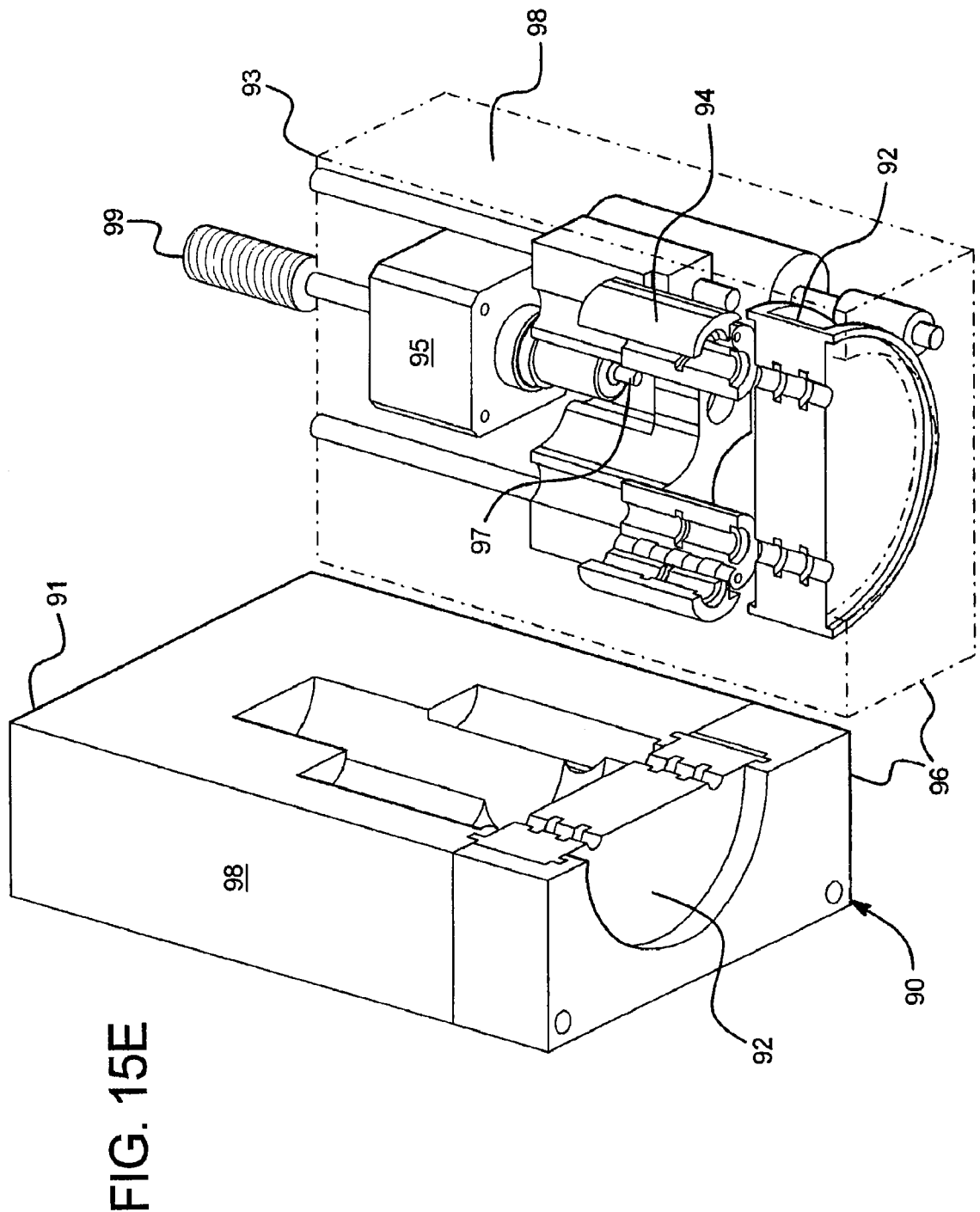

As seen in FIG. 15E, device 90 includes a cover 91 and base 93 which mate (e.g., hingedly or separately) to enclose connectors 56 (with pierceable membrane) and 58 (spike) of lumens 52*a* and 52*b* and lines 84 and 86 when loaded into portions 92 and 94. Cover 91 and base 93 can be plastic or metal as desired. FIG. 15E also illustrates that device 90 includes one or more motor 95 having an output shaft 97 connected operably to portion 94 to move, (e.g., to rotate and/or translate) portion 94 relative to portion 92, which is generally stationary. For example, output shaft 97 of motor 95 can drive a ball screw that in turn is connected threadingly to portion 94, which enables motor 95 to translate portion 94. In the illustrated embodiment, output shaft 97 of motor 95 is coupled to portion 94 in a manner such that motor 95 can rotate portion 94. A lever 99 is connected to the subassembly of motor 95 and moveable portion 94, such that the patient or caregiver can translate portion 94 back and forth with respect to stationary portion 92 via lever 99. Device 90 is alternatively fully automatic (e.g., AC or battery powered) or fully manual.

Device 90 also includes an apparatus for maintaining an aseptic environment when lumens 52*a* and 52*b* and lines 84 and 86 are pulled apart. For example, device 90 can employ an ultraviolet ("UV") light or radiator described in U.S. Pat. Nos. 4,412,834 and 4,503,333, owned by the eventual assignee of the present application, the entire contents of which are incorporated herein by reference. Device 90 can also introduce HEPA or ULPA filtered air into the volume around the connector prior to connection.

Referring additionally to FIGS. 15A to 15D, once the dual lumen patient line 52 and transfer set 82 are loaded into device 90, the patient line shown here as having fill lumen 52*a* (terminating in a female connector 56 as described above) and drain lumen 52*b* (terminating in a spike connector 58 as described above) are split apart and connected to the patient's transfer set 82. Transfer set 82 includes a fill line 84 (terminating in a spike connector 58) and a drain line 86 (terminating in a female connector 56).

In FIG. 15A, fill lumen 52*a* is connected via the prime sequence to drain lumen 52*b*. Fill line 84 and drain line 86 or transfer set 82 are also connected. Mated connectors 56 and 58 of each pair are loaded into device 90, such that return lumen 52*b* and fill line 84 (both having spike connectors 58) are loaded into stationary portion 92 of device 90 and fill lumen 52*a* and drain line 86 (both having female connectors 56) are loaded into rotatable portion 94 of device 90. In one embodiment portions 92 and 94 are structured such that portion 92 can only accept spike connectors 58 and portion 94 can only accept female connectors 56. Cover 91 of device 90 is closed and the aseptic apparatus is initiated or energized.

In FIG. 15B, portion 94 via, e.g., electrically actuated stepper motor 95 coupled to a ball screw (not illustrated), or solenoid (not illustrated), pulls lumens 52*a* and 52*b* and lines 84 and 86 apart, respectively. Portion 90 includes a carriage holding connectors 56 of lumen 52*a* and line 86, which are pulled apart from spike connectors 58. Translatable portion 94 and motor 95 can be housed completely within device 90 and sealed from the outside environment.

In the illustrated embodiment, the translator is operated manually via lever 99 that the patient grabs and translates to translate portion 94 carrying connectors 56 of lumen 52*a* and line 86 towards/away from spike connectors 58. In the illustrated embodiment, a thinner shaft of lever 99 is sealed to device 90, such that the handle portion of lever 99 remains outside device 90 and is configured for the patient to grasp and move comfortably. The shaft of lever 99 is connected to motor 95, which in turn is coupled to portion 94 holding connectors 56 of lumen 52*a* and line 86.

In FIG. 15B, the aseptic apparatus of device 90 continues to be energized to prevent the tips of connectors 56 and 58 from becoming contaminated.

In FIG. 15C, motor 95 rotates rotatable portion 94 holding female connectors 56 one-hundred-eighty degrees relative to stationary portion 92, such that return lumen 52*b* of dual lumen patient line 52 is aligned with drain line 86 of transfer set 82. Also in this configuration, fill lumen 52*a* of dual lumen patient line 52 is aligned with fill line 84 of transfer set 82. The aseptic apparatus of device 90 continues to be energized to prevent the tips of connectors 56 and 58 from becoming contaminated.

In FIG. 15D, translatable portion 94 (electric or manual) pushes fill lumen 52*a* of dual lumen patient line 52 towards fill line 84 of transfer set 82, connecting spike connector 58 to female connector 56. Simultaneously, return lumen 52*b* of dual lumen patient line 52 is connected sealingly and operably with drain line 86 of transfer set 82. System 10 can now perform an initial patient drain to remove the prior procedure's spent last-bag fill and ready the patient for a first fill of the present therapy.

It should be appreciated that the sequence of FIGS. 15A to 15D works no matter which side 96 or 98 of device 90 connected lumens 52a and 52b and connected lines 84 and 86 are loaded in FIG. 15A.

In a patient disconnection sequence, connected inflow lines 52a and 84 are loaded into one side 96 or 98 of device 90. Connected outflow lines 52b and 86 are loaded into the other side of device 90. In a next step, device 90 (manually or automatically) disconnects cassette inflow line 52a from transfer set inflow line 84 and cassette outflow line 52b from transfer set outflow line 86.

Next, rotatable portion 94 holding female connectors 56 is rotated one-hundred-eighty degrees relative to stationary portion 92, such that now return lumen 52b of dual lumen patient line 52 is aligned with fill lumen 52a of dual lumen patient line 52, and drain line 86 of transfer set 82 is now aligned with fill line 84 of transfer set 82.

In a next step, device 90 (manually or automatically) connects cassette inflow line 52a to cassette outflow line 52b and transfer set inflow line 84 to transfer set outflow line 86. Device 90 provides an aseptic environment for the above four steps. The patient can then remove the connected dual lumen line 52 and transfer set 82 from device 90 and is free from the dialysis instrument.

It should be appreciated that device 90 is not limited to the dual lumen patient line 52/transfer set 82 connection/disconnection application just described or even to APD. For example, a single patient line 84 having a spike connector 58 protected by a female cap 56 could be loaded instead into side 98 of device 90, while a supply bag pigtail 46 having a female pierceable connector 56 and a cap is loaded into side 96 of device 90. The female cap 56 is next removed from male-ended patient line 84, while a cap is removed from female-ended supply pigtail 46 simultaneously from its cap (by pulling rotatable portion 94 away from portion 92). Next, rotatable portion 94 is rotated with respect to portion 92. Afterwards, female portion 94 is slid towards portion 92, mating spike connector 58 of patient line 84 with female connector 56 of supply bag pigtail 46, thus connecting a supply bag 40 to the patient, for example for CAPD. A similar connection could be made connecting the patient to pumping cassette 28.

Patient Drain and Fill

During patient drain, system 10, removes effluent from the patient through return lumen 52b of dual lumen patient line 52. When drain is completed and system 10 advances to a fill cycle, system 10 delivers fresh fluid to the patient through fill lumen 52a of dual lumen patient line 52. Here, the only effluent that is "recirculated" back to the patient is the small volume of effluent in fill line 84 of transfer set 82 and the patient's catheter. Even this volume need not be recirculated to the patient if a dual lumen catheter and transfer set is used. Further, if a dual lumen catheter and dual lumen transfer set is used with system 10, system 10 can perform a multiple pass continuous flow peritoneal dialysis ("CFPD") therapy. The multiple pass CFPD therapy can employ a single fill, with a long recirculating flow dwell, or the CFPD therapy can be tidal in nature and recirculate flow during at least one of the dwell periods.

Cassette Improvements

Referring now to FIG. 16, cassette 100 illustrates one embodiment of a cassette and method of making same, in which a rigid plastic portion 110 of the cassette is encapsulated within cassette sheeting 102. However, sheeting 102 is not welded to the sides of the rigid portion 110, sheeting 102 is instead welded to itself. Plastic portion 110 in one embodiment is rigid and made of acrylonitrile butadiene styrene ("ABS"), acrylic, polyolefin, polycarbonate, polyethylene or polypropylene. Sheeting 102 in one embodiment is flexible, e.g., for flexing to pump liquid, and opening and closing valve chambers. Sheeting 102 can be made of polyvinyl chloride ("PVC"), polyethylene, kraton or polyolefin. Also, two or more plies of the different or same materials can be used, wherein the grains of the plies can flow perpendicular to each other to increase strength and minimize the potential for slits, holes and tears. For example, the outside layer opposite the cassette can have good abrasion, puncture and tear resistant properties and a middle layer having good strength properties.

Sheeting 102 is folded to produce a first side 104a, a second side 104b, a folded top 106 and edges 108a to 108c as illustrated. Folded sheet 102 is slid over rigid portion 110 as shown in FIG. 16. Next, side edges 108a of sides 104a and 104b are welded together and around supply lines 48, patient lines 52 or drain line 54. Alternatively, edges 108a of sides 104a and 104b are welded together and around ports extending from rigid portion 110 (not seen in FIG. 16), to which supply lines 48, patient lines 52 or drain line 54 are fitted sealingly. Bottom edges 108b of sides 104a and 104b are welded together. Side edges 108c of sides 104a and 104b are welded together. Flexible sheeting 102 in this manner forms a sealed pouch around rigid portion 110. Sides 104a and 104b are alternatively separate sheets welded together along four sides.

Rigid portion 110 includes or forms pump chambers 112. As described below, an alternative cassette includes three pump chambers. Rigid portion 110 in the illustrated embodiment also includes a plurality of valve chambers 114. Pump chambers 112 and valve chambers 114 each include ridges 116 defining the respective pump or valve chamber, which extend outwardly from a base wall 118 of rigid portion 110. The opposite side of rigid portion includes ridges 116 extending in the other direction from base wall 118 and defining flow paths (not seen) that communicate with the pump chambers 112 and valve cambers 114.

In operation, side 104a of sheeting 102 needs to be sealed to ridges 116 of the pump and valve chambers for the pneumatic movement and control of fluid. A dialysis instrument operating with pouch cassette 100, which has sheeting 102 sealed to itself around rigid portion 110 (and to the tubes as discussed above) but not directly to raised ridges 116, applies a positive pressure across the surface 104a relative to rigid portion 110. The positive pressure seals surface 104a to the raised ridges 116 temporarily during operation so that pumps 112 and valves 114 can function properly. Positive pressure is also provided on reverse surface 104b of sheeting 102 to compress surface 104b to raised ridges 116 of the flow paths (not seen). The positive pressure can be provided pneumatically, e.g., via an inflatable bladder, and/or mechanically, e.g., via spring biasing, solenoid actuation and/or the closing of a door behind which cassette 100 is loaded.

FIG. 16 also shows that base wall 118 can include instrument loading and locating holes 120, which enable a locating guide 122 to be snapped in place after sheeting 102 has been welded to itself and to tubing 48, 52 and 54. In an embodiment, sheeting 102 is welded via a heat seal process, which uses a die. That same die can also punch aligning holes 124 through sheeting 102 to facilitate the installation of the loading/locating guide 122.

Cassette 100 includes integrated valve ports 114. System 10 of FIGS. 1 to 3 and instrument 20 of FIG. 12 show pinch valves 68 external to the cassette, which occlude associated tubing. Pinch valves 68 allow system 10 to access each of the supply lines independently but also to eliminate the need for the manual clamps that are typically present on cassette supply lines 48. Machine 20, not the user, occludes supply lines 48 when it is necessary to do so, for example when bag connections are made and opened to perform the therapy. Supply lines 48 also need to be occluded after many alarm/failure conditions or if the power fails.

The pinch valves 68 also aid in the drawing of fluid from the solution lines 46. For example, the pinch valve 68 to only the top shelf 38 can be opened, allowing bag 40d to drain partially, e.g., more than 50%, before opening valve 68 to supply bag 40c on the second-to-top shelf 36 allowing bag 40c to drain partially, e.g., more than 50%, before opening valve 68 to supply bag 40b on the third-to-top shelf 34, allowing bag 40b to drain partially, e.g., more than 50%, before opening valve 68 to supply bag 40a on bottom shelf 32. Fluid will flow via gravity into the pumps and air will tend to float to the back of each bag 40. Using this sequence, all of supply bags 40 can be emptied without sucking any air into the solution lines 46. If all supply lines 48 are opened at once, lower bags 40a and 40b will become bloated due to the weight of fluid from the upper supply bags 40c and 40d.

It should be appreciated that flexible pouch cassette 100 can include valve chambers 114 or not include valve chambers 114 if the above described pinch valves 68 are used instead. Further, it should be appreciated that the apparatuses and methods disclosed in connection with system 10 and instrument 20 are not limited to use with pinch valves 68 and instead can be used with valve chambers 114 discussed above. Further alternatively, system 10 can operate with a combination of valve chambers 114 and pinch valves 68, e.g., using cassette-based valve chambers 114 during treatment and pinch valves 68 during setup and alarm conditions.

Referring now to FIGS. 17A, 17B, cassette 130 illustrates one embodiment of a three pump chamber disposable pumping and valving cassette. FIGS. 18A to 18C illustrate three methods for operating the three pump chambers to achieve desired outputs.

Cassette 130 in the illustrated embodiment includes many of the same structures or types of structures as cassette 100, such as rigid portion 110 having a base wall 118 with ridges 116 extending from the base wall 118 to form pump chambers 112a to 112c (referred to herein collectively as chambers 112 or generally, individually as chamber 112). Ridges 116 also define valve chambers 114 as described above. Alternatively, cassette 130 with three valve chambers 112 operates with pinch valves 68 and does not use or provide valve chambers 114.

Figure 17C:
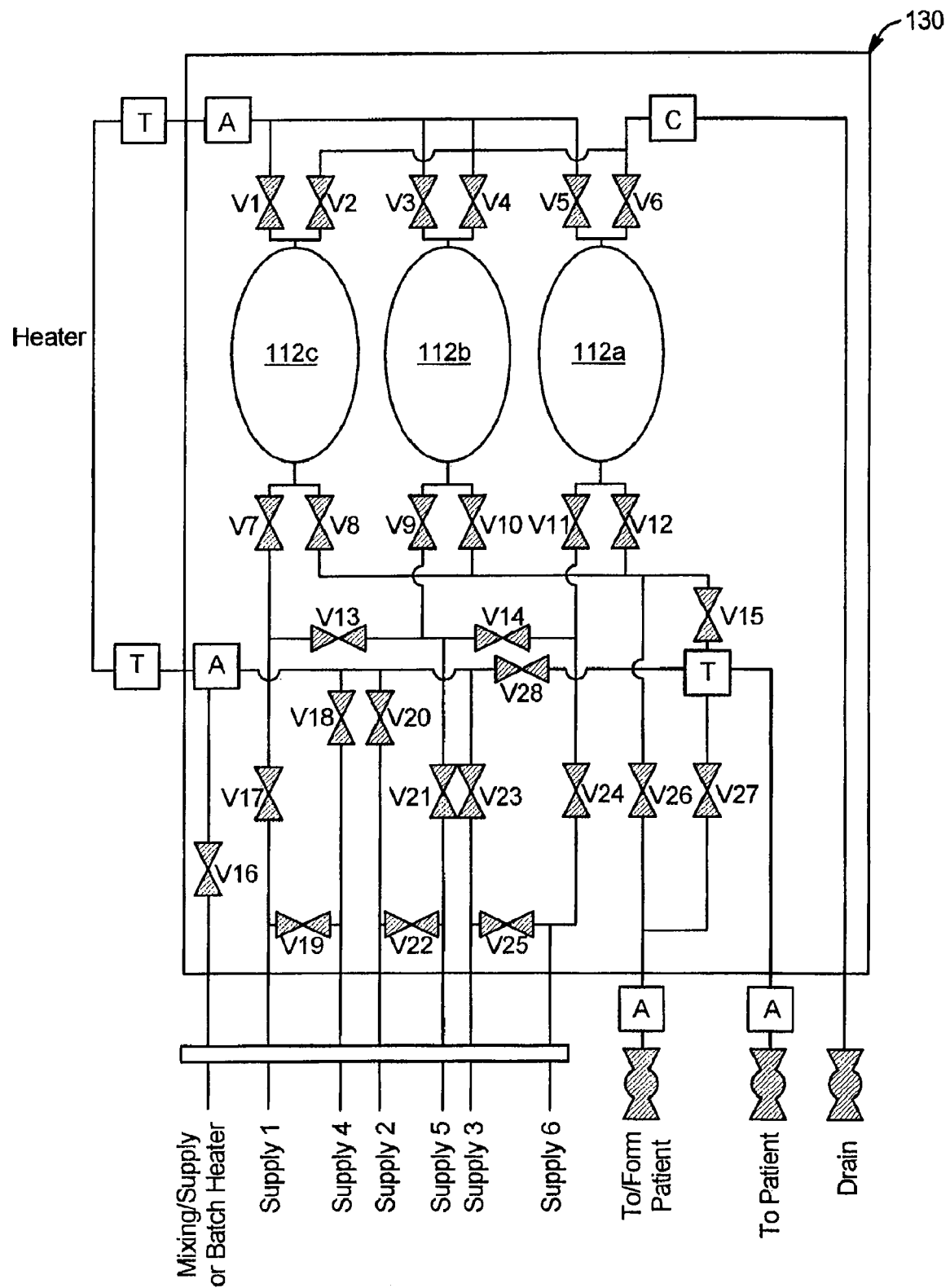
FIG. 17C shows one possible valve arrangement for the three pump chamber cassette of FIGS. 17A and 17B for achieving the pumping regimes shown in connection with FIGS. 18A to 18C.
Figure 18A:
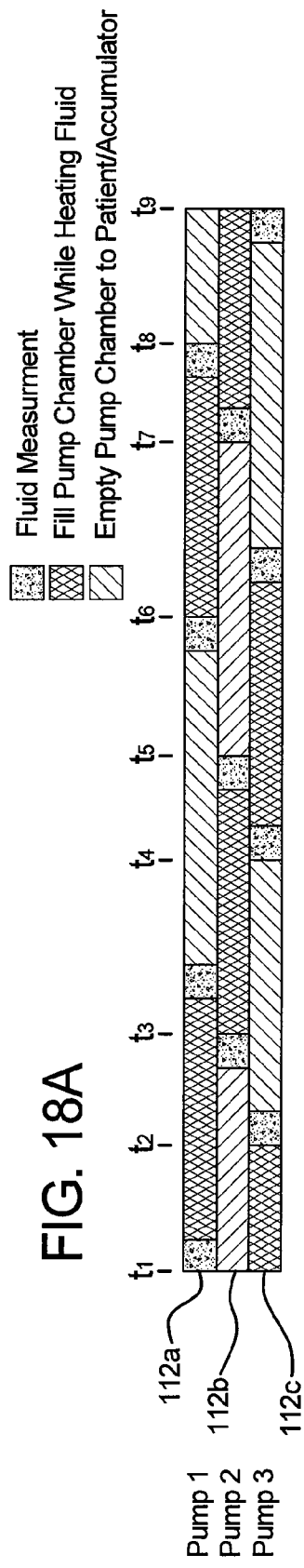
FIGS. 18A to 18C are schematic views showing pumping sequences using the three pump chamber cassette of FIGS. 17A and 17B.
Figure 18B:
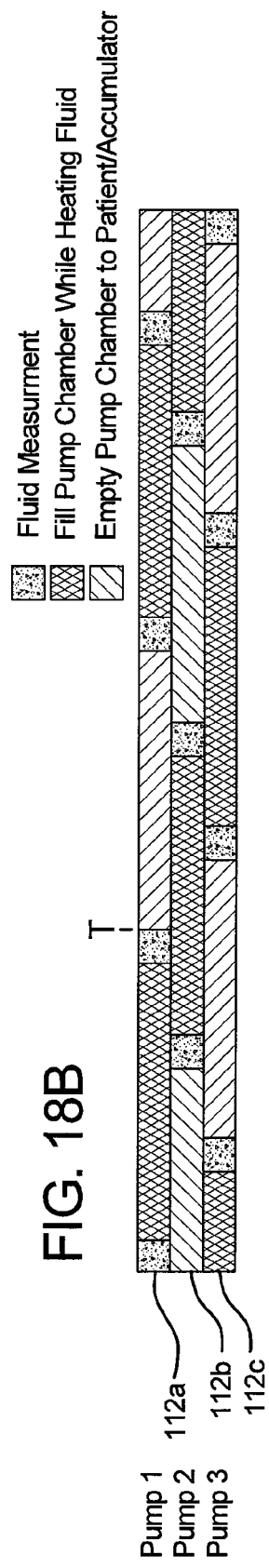
Figure 18C:
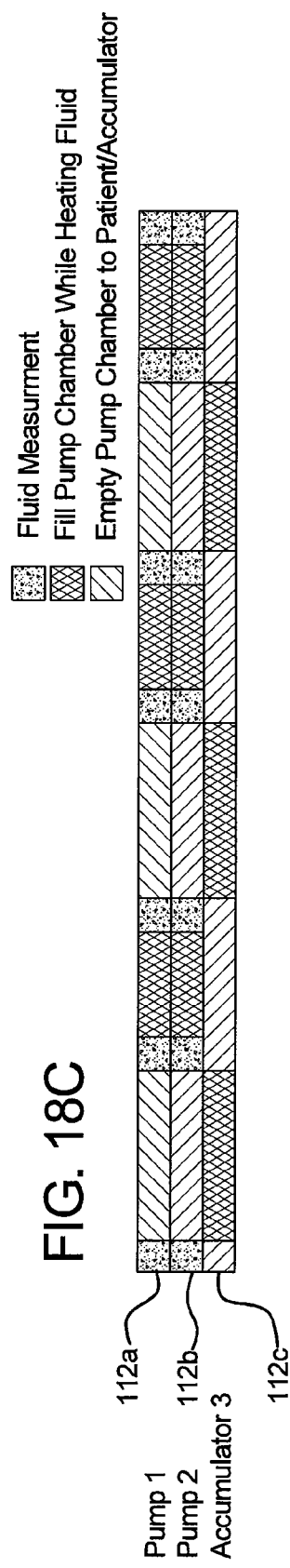

FIG. 17B illustrates the back side of cassette 130. Here, ridges 116 extending from base wall 118 define a flow path 132. Flow path 132 includes manifold sections 134a and 134b and baffled sections 136a to 136f extending between manifold sections 134a and 134b. Manifold sections 134a and 134b and baffled sections 136a to 136f of flow path 132 enable cross-talk between pump chambers 112, so that the flow patterns discussed below in connection with FIGS. 18A to 18C can be achieved as shown in more detail below in connection with FIG. 17C.

Cassette 130 includes flexible sheeting 104a and 104b as discussed above. Sheeting 104a and 104b can be separate sheets welded or bonded to the sides of rigid portion 110 and ridges 116 of pump chambers 112 and valve chambers 114. Alternatively, sheeting 104a and 104b is provided via a single sheet 102 shown above, which includes a folded edge 106 and welded or bonded edges 108a to 108c as shown and described in connection with FIG. 16.

FIG. 17C illustrates one possible valve arrangement for the three pump cassette 130 of FIGS. 17A and 17B. FIG. 17C illustrates the ports extending out the bottom of cassette 130, which is one preferable arrangement for air handling because any air in cassette 130 will tend to rise to the top of the cassette, leaving only fluid to exit the cassette from the bottom. Boxes marked "A" are areas of cassette 130 that interact with air sensors located within instrument 20. Boxes marked "T" are areas of cassette 130 that interact with temperature sensors located within instrument 20. The Box marked "C" is an area of cassette 130 that interacts with a conductivity sensor located within instrument 20.

As illustrated, cassette 130 includes six supply ports, a dedicated to-patient port, a to/from-patient port, a drain port, and an additional port for mixing, further supplying, or sending or receiving fluid from a batch heater. Cassette 130 includes three pump chambers 112a to 112c described above. Valves 114 in FIGS. 17A and 17B are differentiated via valves V1 to V28. The following valve states are merely examples showing different flow regimes achievable via cassette 130.

Filling the patient with a premixed solution can for example occur by allowing fresh mixed solution into cassette 130 via valve V16, flowing through the heater via valve V1 into pump chamber 112c. At the same time, pump chamber 112b pushes the same fluid to patient via open valves V10, V15, V27 and the to/from patient port valve. In this regime, to-patient port and valve are not needed. At the same time, pump chamber 112c can be performing a volume measuring determination as discussed below. In an alternative embodiment, dedicated to-patient port and valve are used as a second outlet to the patient.

Draining effluent from the patient can for example occur by allowing effluent into cassette 130 via to/from patient valve and port, flowing through valves V26 and V12 into pump chamber 112a. At the same time, pump chamber 112b pushes the effluent to drain via open valves V4 and the drain valve. In this regime, dedicated to-patient port and valve are not needed. At the same time, pump chamber 112a can be performing a volume measuring determination as discussed below. In an alternative embodiment, temperature sensor access valve V15 can be opened simultaneously to allow temperature of the effluent entering chamber 112a to be sensed.

In a concentrate mixing regime, chamber 112c can be filling from concentrate supply 1 through valves V17 and V7. Chamber 112b can be filling from concentrate supply 2 through valves V20 and V9. Chamber 112a, here acting as an accumulator as described below in FIG. 18C, outputs mixed concentrates via valves V5 and V16 to a mixer, for example. In an alternative embodiment, a separate mixer is not used, the length of the patient line is sufficient to mix the concentrates, and chamber 112a outputs alternatively through valves V5, V28, V27 and the to/from patient valve collectively to the patient.

In a second stroke as described below in FIG. 18C, chambers 112c and 112b empty half of their respective concentrates through valves V1 and V3, respectively and V5 collectively into chamber 112a. At the same time, chambers 112c and 112b empty the other half of their respective concentrates through valves V1 and V3, respectively and valve V16 collectively to a mixer. In an alternative embodiment, a separate mixer is not used, the length of the patient line is sufficient to mix the concentrates, and chambers 112c and 112b empty the other half of their respective concentrates alternatively through valves V1 and V3, respectively and valves V28, V27 and the to/from patient valve collectively to the patient.

In a multi-pass flow regime, chamber 112c fills with fresh, e.g., premixed, solution from supply 1 through valves V17 and V7. At the same time, chamber 112b empties fresh solution to the patient via valves V3, V28 and the to-patient valve to the patient. At the same time, chamber 112a fills with effluent from the patient via the to/from patient valve, and valves V26 and V12. Here, the fluid can be recirculating because there is no net fluid loss or ultrafiltration ("UF") taking place.

In a UF to drain mode multi-pass flow example, chamber 112c empties fresh solution to the patient via valves V1, V28 and the to-patient valve to the patient. At the same time chamber 112b fills with effluent from the patient through the to/from patient valve, and valves V26 and V10. At the same time, chamber 112a empties effluent to drain via valve V6 and the drain valve. In an alternative UF bag to bag multi-pass mode, chamber 112a alternatively empties effluent to an empty supply bag, e.g., supply 3 via valves V11, V24 and V25.

In a second state of the UF bag to bag multi-pass mode, chamber 112c fills with fresh, e.g., premixed, solution from supply 1 through valves V17 and V7. At the same time, chamber 112b empties fresh solution to the patient via valves V3, V28 and the to-patient valve to the patient. At the same time, chamber 112a fills with effluent from the patient via the to/from patient valve, and valves V26 and V12.

A test can be run to see if a dual or multi-chamber bag has been opened properly. Here one of pump chambers empties fluid to drain, flowing the fluid past conductivity sensor ("C"), which checks to see if the conductivity measured is indicative of a properly mixed solution, in which case therapy can proceed, and an improperly mixed case in which an alarm is generated.

FIG. 18A illustrates one pumping sequence for pump chambers 112 in which a chamber fill stroke (cross-hatched segments) is slightly shorter in duration than a chamber empty stroke (diagonal segments), which are separated by relatively short fluid measurement periods (dotted segments). A fluid measurement (amount of fluid pumped) method is discussed in detail below. Also discussed below is a way to eliminate the fluid measurement periods (dotted segments) occurring after the chamber empty strokes (diagonal segments).

In one embodiment, a pneumatic actuator applies negative and positive pressure to sheet 104a to pump fluid into or out of one of pump chambers 112. A pump controller, e.g., microprocessor and computer program memory, controls pneumatic actuators to apply positive, negative or no pressure to the appropriate chamber 112 at the appropriate time. The processor cycles through a program which at any given time tells the processor which state each pump actuator should be in. The processor controls each actuator based upon that cycle.

Three pump cassette 130 provides continuous flow to the patient during fill, while also drawing fluid continuously from the supply bag through an inline heater for example. As seen in FIG. 18A, at any given time at least one pump chamber 112a to 112c is delivering fluid to the patient or to an accumulator (one purpose for an accumulator is described below in connection with FIG. 18C). At any given time at least one pump chamber 112a to 112c is filling the patient with heated dialysate.

As seen in FIG. 18A, at time t1, pump chamber 112a is at rest for a measurement calculation from a previous emptying stroke, pump chamber 112b is emptying fluid to the patient, pump chamber 112c is filling with fluid. At time t2, pump chamber 112a is filling with fluid, pump chamber 112b is still emptying fluid to the patient, pump chamber 112c is at rest for a measurement calculation from a previous filling stroke. At time t3, pump chamber 112a is still filling, pump chamber 112b is starting a fill stroke, pump chamber 112c is emptying. At time t4, pump chamber 112a is emptying, pump chamber 112b is filling, pump chamber 112c is starting a rest period for measurement calculation. At time t5, pump chamber 112a is still emptying, pump chamber 112b is beginning to empty, pump chamber 112c is filling. At time t6, pump chamber 112a is filling, pump chamber 112b is emptying, pump chamber 112c is filling. At time t7, pump chamber 112a is still filling, pump chamber 112b is starting a rest period for measurement calculation, and pump chamber 112c is emptying. At time t8, pump chamber 112a is starting an emptying stroke, pump chamber 112b is filling, and pump chamber 112c is emptying. At time t9, pump chamber 112a is emptying, pump chamber 112b is filling, and pump chamber 112c is starting a fill stroke.

While the above sequence is described in connection with fresh fluid either filling the pump chambers 112a to 112c or emptying chambers 112 to the patient, the same sequence can be employed in connection with spent fluid either filling the pump chambers 112a to 112c or emptying chambers 112 to drain. In either case, filling and emptying pump chambers 112 is continuous when the operation of the three chambers 112 is superimposed.

FIG. 18B shows a similar sequence to that of FIG. 18A. Here, however, the overlap of the filling strokes and emptying strokes is the same. FIG. 18B illustrates that the relative durations of the filling and emptying strokes can be modified to suit a particular pump chamber and actuation configuration. FIGS. 18A and 18B also show that each time an emptying stroke is about to start, another emptying stroke already in progress is going to stay in progress long enough such that the start of the empty stroke can be delayed for a short period of time, e.g., to discharge a small amount of air from the chamber about to start without disrupting the continuity of the fluid emptying. For example, at time T in FIG. 18B, pump chamber 112a is supposed to start emptying either fresh fluid to the patient or spent fluid to drain. The start of the pump-out stroke could be delayed for a short period of time to discharge air for example, without disrupting the continuous flow because pump chamber 112c still has some of its emptying stroke remaining.

FIG. 18C illustrates a sequence in which fluid is being mixed, e.g., from two sources to make a stable dialysate for the patient. This can be done for either PD or HD, either online or from bags or containers. Here, pump chambers 112a and 112b are synchronized. Pump chambers 112a and 112b receive fresh fluid that has already been mixed in one embodiment. Alternatively, pump chamber 112a pumps one fluid, while pump chamber 112b pumps a second fluid, each to a same line in which the two fluids are mixed properly. Pump chamber 112c is an accumulator that receives mixed fluid from pump chambers 112a and 112b. Pump chamber 112c outputs to the patient.

The system operating the sequence of FIG. 18C is valved or the flow paths of the system are structured such that half of the mixed fluid leaving pump chambers 112a and 112b during the emptying stroke flows to the patient, while the other half flows to fill pump chamber or accumulator 112c. When pump chambers 112a and 112b are filling, accumulator or pump chamber 112c sends its mixed fluid volume to the patient. Since all fluid flowing to and from accumulator 112c has been accounted for in the measurement periods of pump chambers 112a and 112b, separate measurement periods for pump accumulator 112c are not needed. Here, flow to the patient is continuous. Filling from the concentrate sources is intermittent. A similar routine could be used to remove effluent from the patient. Accumulator 112c is always attempting to fill with effluent from the patient with this routine. When pumps 112a or 112b fill, the pumps pull some fluid from accumulator 112c as well as from the patient. A routine such as one of FIG. 18A or FIG. 18B can also be used instead to pull effluent so that flow from the patient is continuous and smoother.

Cassette Interface Improvements

Referring now to FIGS. 19 to 22, pneumatic system 150 illustrates one embodiment of a disposable cassette pumping interface of the present disclosure. System 150 includes a disposable cassette 140. Disposable cassette 140 is similar to cassettes 100 and 130 described above and includes many of the same components, which are numbered the same. Cassette 140 includes a rigid housing or portion 110. Flexible sheets 104a and 104b (not seen in FIG. 19) are welded or bonded to rigid portion 110. Alternatively, sheets 104a and 104b are formed from the single folded sheet 102 discussed above in connection with cassette 100. Cassette 140 is shown from the reverse side as that shown in FIG. 16 for cassette 100. Here, pump chambers 112a and 112b bulge outwardly, showing the reverse side of pump chambers 112 as shown in FIG. 16. Cassette 140 can alternatively include the third pump chamber 112c discussed above in connection with cassette 130.

Figure 19:
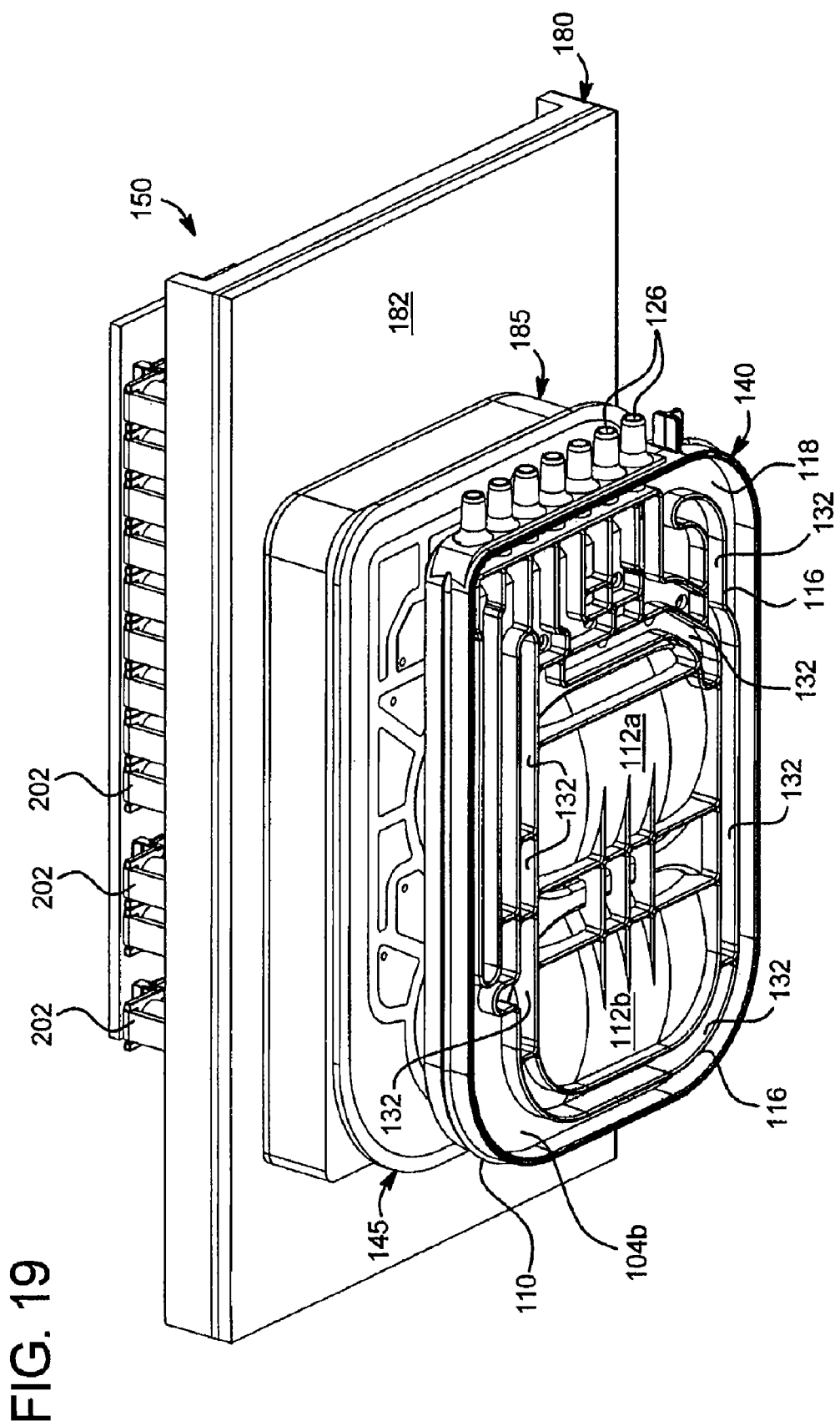
FIG. 19 is a perspective view of one embodiment of a pneumatic pumping system of the present disclosure, which includes a manifold cassette interface, a membrane gasket and a disposable cassette.

Cassette 140 includes a base wall 118 as described above. Ridges 116 extend outwardly from base wall 118 to form a plurality of flow paths 132. The valve chambers 114 and surfaces of pump chambers 112 interacting with the cassette sheeting are provided on the opposite side of cassette 140 than the side that is shown in FIG. 19. Cassette 140 further includes a plurality of valve ports 126, which communicate fluidly with flow paths 132 and connect sealingly to tubes, such as supply tubes 48, patient line 52 and drain line 54 shown above for example in connection with FIG. 16.

Figure 20:
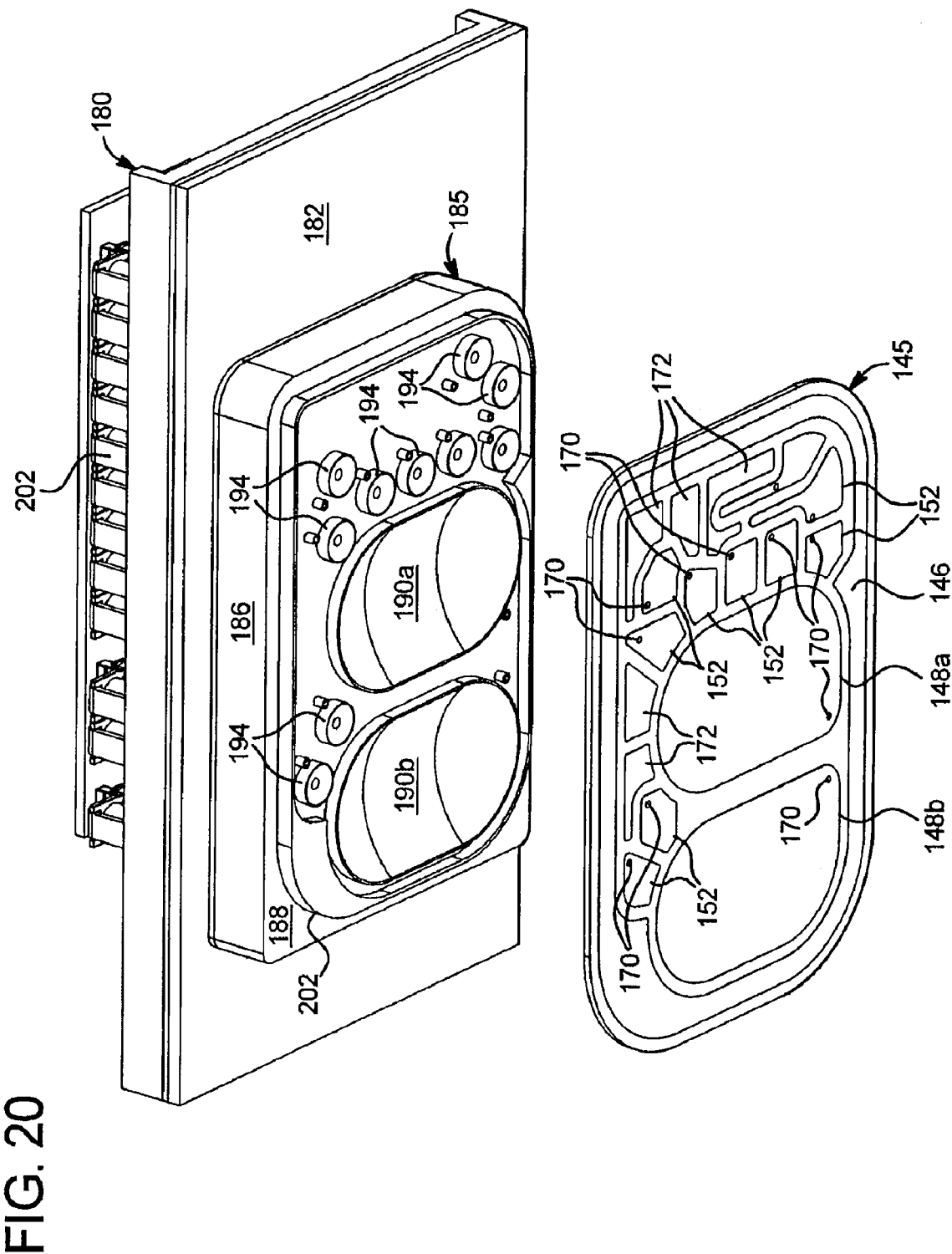
FIG. 20 is a perspective view of a manifold cassette interface and membrane gasket of the pneumatic pumping system of FIG. 19.
Figure 21:
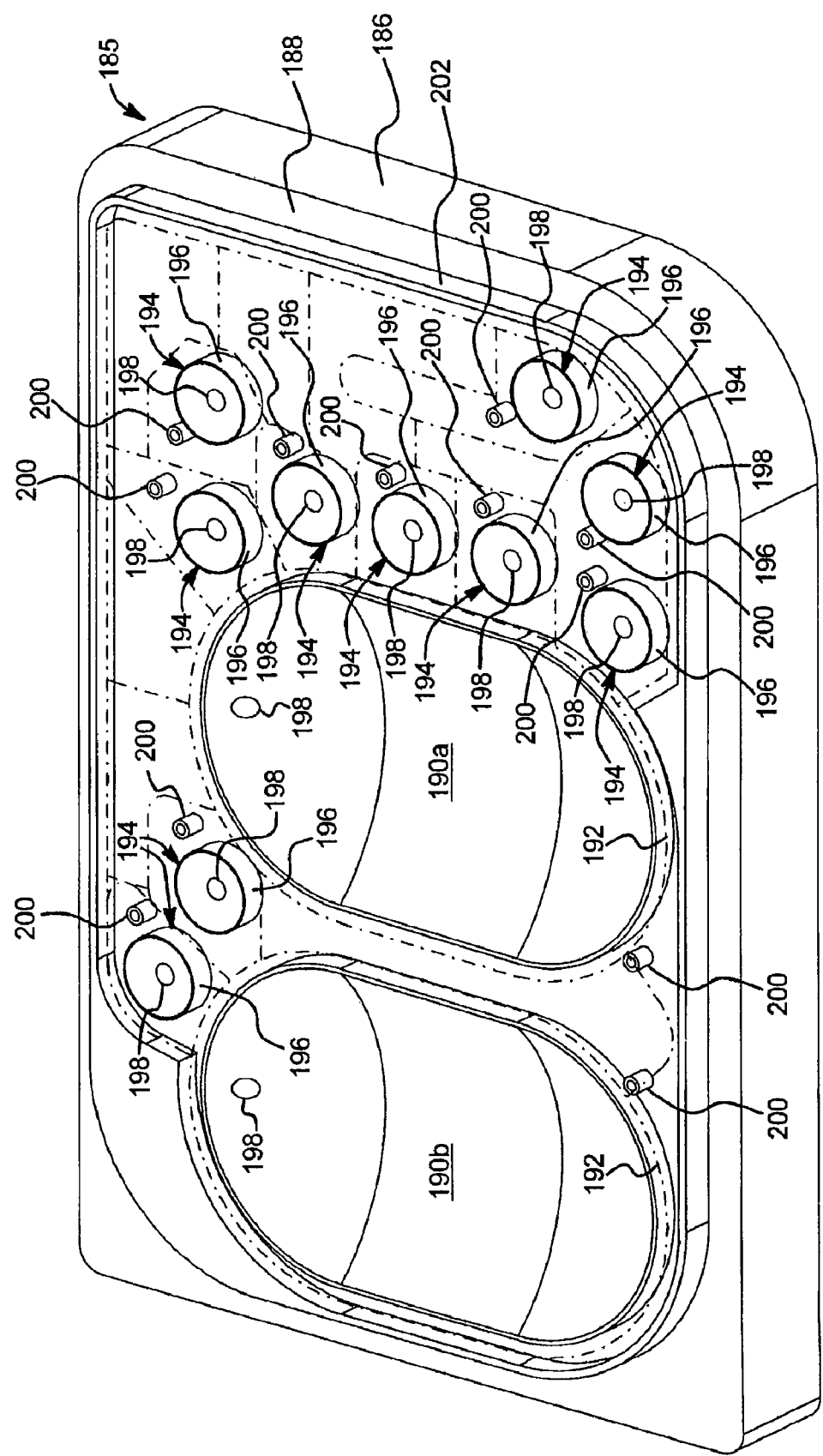
FIG. 21 is a perspective view of an interface plate of the cassette interface of the pneumatic pumping system of FIG. 19.
Figure 22:
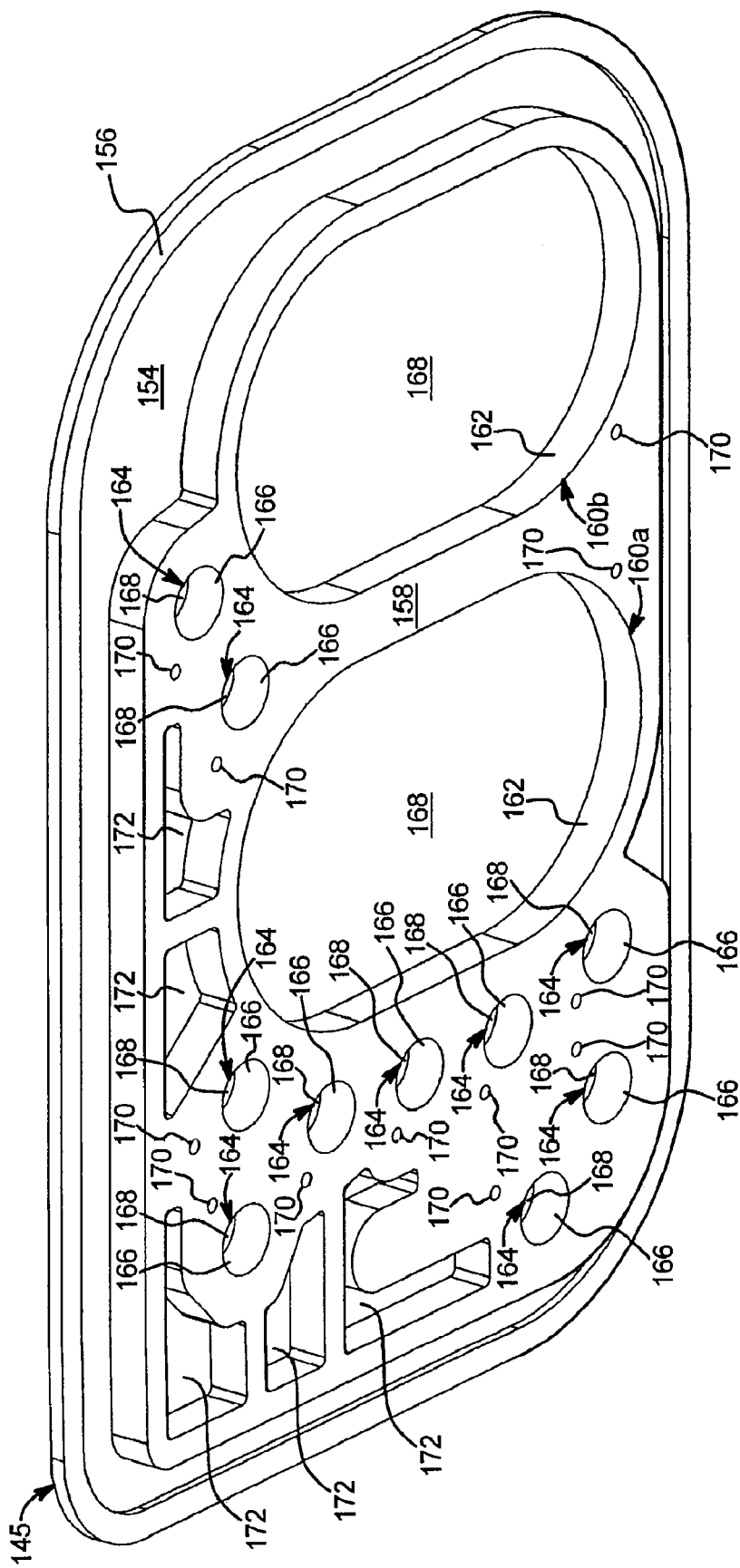
FIG. 22 is a perspective view of a membrane gasket of the pneumatic pumping system of FIG. 19.

Pneumatic system 150 includes a membrane gasket 145, which is shown in detail in connection with FIGS. 20 and 22. Membrane gasket 145 press-fits and seals in a plurality of places to a cassette manifold 180, which is shown in detail in connection with FIGS. 20 and 21. In particular, cassette manifold 180 includes a interface plate 185, to which membrane gasket 145 is attached and sealed.

Referring now to FIGS. 20 and 22, membrane gasket 145 is described in detail. Membrane gasket 145 is made of a suitable compressible and watertight material, such as silicone rubber, ethylene propylene diene monomer ("EPDM") rubber, viton or other elastomers having a good fatigue life. In one embodiment, membrane gasket 145 is made of compression molded silicone rubber. Membrane gasket 145 includes a side 146, which interfaces with, and indeed moves with, sheet 104a of cassette 140. Membrane gasket 145 includes an opposite side 154, which interfaces with and seals in various places to interface plate 185.

Cassette side 146 of membrane gasket 145 includes raised pump ridges 148a and 148b, which in an embodiment mate with and press seal against raised ridges 116 shown for example in FIGS. 16 and 17A as forming the shape of pump chambers 112. A pneumatic bladder, e.g., contained in the door of instrument 20, can be inflated when the door is closed to press a gasketed plate (not shown) against cassette 140 which, in turn, compresses sheeting 104a of cassette 140 against raised ridges 148a and 148b, such that ridges 148a and 148b form an o-ring-like seal around raised ridges 116 of pump chambers 112 of disposable cassette 140. This seal is described in U.S. Patent Application No. 2004/019313 A1, entitled, "Systems, Methods and Apparatus for Pumping Cassette Based Therapies", and U.S. Pat. No. 6,261,065, entitled, "Systems and Methods for Control of Pumps Employing Electrical Field Sensing", both of which are incorporated herein by reference and are assigned to the eventual assignee of the present disclosure.

Cassette facing surface 146 of membrane gasket 145 further includes raised ridges 152 forming an enclosed path which, in the same manner, seals around raised ridges 116 of valve chambers 114 of disposable cassette 140. FIG. 16 shows ten valve chambers 114, which are generally aligned with and have the same shape as the ten enclosed ridges 152 of cassette surface 146 of membrane gasket 145. Again, in an embodiment, enclosed ridges 152 mate with and press seal against ridges 116 of valve chambers 114 of the disposable cassette 140.

FIG. 22 illustrates the opposite surface 154 of membrane gasket 145, which faces and interacts with interface plate 185 of cassette manifold 180. A raised rim 156 runs along the outside of surface 154, so that the gasket holds its shape. An inner plateau 158 also extends out from surface 154. The removal of material between plateau 158 and raised rim 156 allows the two structures to move independently when the instrument door is closed and cassette 140 is pressed between the instrument door and membrane gasket 145, which is retained by interface plate 185. Raised rim 156 optionally seals about a raised edge 202 of interface plate 185, helping membrane gasket 145 to seal to the interface plate and prevent water or particle ingress.

Plateau 158 defines a pair of blind pump wells 160a and 160b. Blind pump wells do not extend all of the way through the thickness of membrane gasket 145. Instead, pump wells 160a and 160b each include sidewalls 162, which extend most of the way through the thickness of membrane gasket 145 but leave a thin wall 168. As described in detail below, thin walls 168 move with sheeting 104 of cassette 140 residing within pump chambers 112a and 112b of the cassette.

In a similar manner, plateau 158 defines a plurality of blind valve wells 164. Blind valve wells 164 likewise do not extend all of the way through plateau 158 of membrane gasket 145. Instead, blind valve wells include sidewalls 166 that extend most of the way through plateau 158 but terminate at blind wall 168. Blind wall 168 of blind valve wells 164 in turn operate with sheeting cassette 104a at valve chambers 114.

Membrane gasket 145 defines ports or apertures 170 that extend all of the way through plateau 158 of membrane gasket 145. Accordingly, apertures 170 are seen on both plateau 148 of FIG. 22 and surface 146 of FIG. 20. As further seen in FIG. 20, raised pump ridges 148a and 148b and raised valve ridges 152 on surface 146 of membrane gasket 145 enclose or encompass pneumatic ports 170. As discussed in detail below, pneumatic ports 170 enable a negative pressure asserted through membrane gasket 145 to pull surface 168 of blind pump wells 160a and 160b and surface 168 of valve wells 164 together with sheeting 104a of cassette 140. The configuration makes wall 168 and sheeting 104a operate as a single membrane for each of the individual pump chambers 112 and valve chambers 114 of the disposable cassette.

Membrane gasket 145 also includes dead spaces 172 which do not extend all of the way through plateau 158. Accordingly, dead spaces 172 are only seen on the bulk surfaces 154 of FIG. 22. Dead spaces 172 remove material from the membrane gasket where it is not needed and, accordingly, enable membrane gasket 145 to be made more cost effectively.

FIGS. 20 and 21 illustrate interface plate 185. Interface plate 185 can be made of metal, such as aluminum, or plastic. Various configurations for interface plate 185 and cassette interface 180 are discussed below in connection with FIGS. 23 to 30. Interface plate 185 includes a sidewall 186, top wall 188 and an enclosed edge 202 extending from top wall 188. As discussed above, edge 202 fits frictionally within rim 156 of membrane gasket 145 to help maintain a sealed environment between the two structures.

Pump chamber wells 190a and 190b are defined in or provided by membrane plate 185. Pump wells 190a and 190b cooperate with pump chambers 112a and 112b respectively of disposable cassette 140. In particular, pump wells 190a and 190b include pneumatic actuation ports 198. When negative air pressure is supplied through ports 198, the negative pressure pulls the combination of blind wall 168 and sheeting 104a associated with the pump chamber towards the wall of well 190a or 190b. This expands the volume between sheet 104a and pump chamber, 12 of rigid portion 110 of cassette 140 causing a negative pressure to be formed within the cassette, which in turn causes a volume of fluid (fresh or spent) to be pulled into the pump chamber 112. Likewise, when positive pressure is applied through aperture 198, the positive pressure pushes the combination of blind wall 168 and cassette sheeting 104a at the pump well 190/pump chamber 112 interface, pushing wall 168 and sheeting 104a into or towards pump chamber 112 of rigid portion 110, which in turn dispels or pushes fluid from the respective pump chamber 112 to the patient or drain.

Pump wells 190a and 190b each include a wall 192. Wall 192 fits sealingly and snugly within wall 162 of a respective blind well 160a or 160b of membrane gasket 145. The sealed interface between walls 192 of interface plate 185 and walls 162 of pump wells 160a and 160b further enhances the sealed and separated operation of the various pumps and valves within system 150.

Interface plate 185 also includes a plurality of raised valve seats 194. In particular, a valve seat 194 is provided for each blind valve well 164 of membrane gasket 145. Each valve seat 194 and blind valve well 164 corresponds to one of the valve chambers 114 of disposable cassette 140. Valve seats 194 include raised sidewalls 196 that extend outwardly from top surface 188 of interface plate 185. Valve wells 164 of membrane gasket 145 fit snugly around valve seats 194, so that walls 166 of valve walls 164 seal against walls 196 of valve seats 194.

Valve actuation ports 198 are defined at least substantially at the center of seats 194. In an embodiment, the top surfaces of valve seats 194 slope downwardly towards the actuation ports 198. This enables mating blind surface 168 and cassette sheeting 104a to be pulled away from valve chambers 114 of cassette 140 to open a respective valve to allow fluid to flow therethrough.

As seen in FIG. 16, each valve chamber 114 includes a relatively centrally located protruding volcano-type port. When cassette 140 is used with system 150 the volcano ports each become aligned with one of the actuation ports 198. When positive pressure is applied through one of the actuation ports 198, the positive pressure pushes the cooperating blind wall 168 and cassette sheeting 104a at the respective valve seat 194 and valve chamber 114 of cassette 140, to cover or close the volcano port, closing the respective valve chamber 114.

As seen best in FIG. 21, interface plate 185 includes a plurality of gasket seal ports 200. A gasket seal port 200 is provided for each pump well 190a and 190b and for each valve seat 194. It should be appreciated from viewing FIGS. 21 and 22 that seal ports 200 mate with apertures 170 of membrane gasket 145. Seal ports 200 can extend part way or all of the way through apertures 170. In an embodiment, apertures 170 press-fit around ports 200 to create a sealed fit between ports and the walls defining apertures 170.

Sealing membrane gasket 145 on the vertical surfaces 196 of the protruding valve seats 194, walls 192 of pump wells 190a and 190b and vacuum ports 200 provide multiple seals for the pump areas and valve areas of the cassette interface. That is, besides the membrane gasket side seals, additional compression seals exist between interface plate 185 and membrane gasket 145 as well as between gasket 145 and cassette sheeting 104a.

In one embodiment the face of the membrane gasket 145 in the thin flexing sections facing the sheeting 104a above the pump and valve chamber of cassette 140 is textured. The surface of that same side of membrane gasket 145 at the thicker sections that compress and seal against the cassette ribs of the pump chambers, valve chambers and flow path separators of cassette 140 are not textured and have a fine, smooth surface finish for creating a good seal between the cassette sheeting 104a and the gasket ridges 148a, 148b and 152.

The texturing of the thin sections of membrane gasket 145 provides flow channels for the air from the vacuum ports to migrate across the face of each of the valve and pump chambers of cassette 140. The texturing also tends to prevent membrane gasket 145 and cassette sheeting 104a from sticking together when it is time to remove the cassette from the system. It is also contemplated to introduce a small positive pressure through ports 200 at the end of the therapy to eject the cassette 140 from the interface plate 185. Alternately, positive pressure can be applied through valve actuation ports 198 (used to close the cassette valve chambers 114 of cassette 140 when it is time to remove the cassette. This action bulges membrane gasket 145 above pump chambers 112 and valve chambers 114 and push cassette 140 away from interface plate 185.

In operation, negative pressure is applied through ports 200 and apertures 170 to pull cassette sheet 104a tight against blind wall 168 of membrane gasket 156 for a given pump chamber or valve chamber. This negative pressure is applied throughout the treatment, regardless of whether a positive pressure or a negative pressure is being applied via the actuation ports 198 of pump wells 190a and 190b and valve seats 194.

As discussed above, the operation of applying positive and negative pressure to cassette 140 is computer-controlled. The processor controlling such actuation is also capable of receiving and processing inputs, such as pressure sensor inputs. For example, a pressure sensor can be fitted and applied to sense the pressure within a manifold linking each of valve seal ports 200.

Using the pressure sensor, the processor in combination with a computer program can perform an integrity test having precision not previously available. Given the above described apparatus, if a hole develops in either membrane gasket 145 or cassette sheeting 104a, the vacuum level in the manifold sensed by the sensor begins to degrade. The sensor output to the processor or logic implementor is indicative of the negative pressure degradation. The processor and computer program detect the decreasing signal and output that a leak is present. The output can prompt any of: (i) shutting down therapy, (ii) sounding an alarm, (iii) showing a visual message, and/or (iv) audibly describing that a leak is present to the patient or caregiver.

The processor also accepts one or more signal from one or more moisture sensor, such as a conductivity sensor. The one or more sensor is placed in the instrument below cassette 140, e.g., in a channeled well beneath cassette 140. The output of the conductivity sensor is combined logically with the output of the pressure sensor.

The logically combined signals from the pressure and conductivity sensors result in the following diagnostic ability. If a leak is detected, e.g., negative pressure degradation is detected, but no moisture is detected, the leak is logically determined to be from membrane gasket 145. That is, cassette 140 is not leaking fluid into the conductivity sensor. If the leak is detected and fluid is detected, the leak is logically determined to be from cassette 140.

To the extent that it is feasible to use multiple pressure sensors with individual pump walls 190a and 190b and valve seats 194 or to multiplex one or more pressure sensors, the diagnostic ability of system 150 can be expended to be able to pinpoint not only which component is leaking, but which area of which component is leaking. For example, the tubing running to ports 200 could be split between pump tubing and valve tubing. A first pressure sensor could multiplex between the tubing leading to the different pumps to pinpoint a leak in either the first or second pump. The conductivity sensor then tells the system if it is a cassette pump leak or a gasket pump leak. A second pressure sensor could multiplex to look for leaks in the different valves. Valve one to valve five for example might all check-out to be holding pressure, while valve six shows a leak, meaning the portion of the cassette sheeting or gasket in operation with valve six is leaking. The conductivity sensor tells the system if it is the cassette sheeting or the gasket at the valve six position that is experiencing a leak.

Another advantage of the cassette interface of the present disclosure is illustrated via FIGS. 23, 24, 25A and 25B, 26A and 26B. System 10 in one embodiment uses a Boyle's Law based fluid measurement method taught in U.S. Pat. No. 4,826,482 ("the '482 Patent"), the entire contents of which are hereby incorporated by reference and relied upon. That method operates on the premise that the air being injected into (or evacuated from) pump actuation port 198 is at the same temperature as the fluid flowing through cassette 140, and at the same temperature of the air within reference chambers 210a and 210b, which is heated to body temperature or about 37° C. If a temperature difference exists between the dialysate and operating air temperatures, volumetric accuracy is compromised.

It is difficult to quickly and accurately measure the temperature of air when the components mounting the temperature sensor are not at the same temperature as the air that is being measured. Also at the present time, a minimum two-hour warm-up time is required before performing a volumetric calibration on the HomeChoice® Pro APD System, which requires that interface plate 185, reference chambers 210a and 210b, pump chambers 112 in pumping cassette 110 and the fluid being pumped all be warmed to about 37° C.

FIGS. 19 and 20 illustrate that pneumatic solenoid valves 202 are mounted directly to plate 182. FIG. 23 illustrates that volumetric reference chambers 210a and 210b, which hold a known volume of air, are located on the reverse side 204 of interface plate 185 in one embodiment. The purposes and operation of volumetric reference chambers 210a and 210b is discussed in the '482 patent and in detail below in connection with FIGS. 27, 28A to 28F and 29, which disclose an improvement over the '482 patent method. It is enough now to understand that chambers 210a and 210b are used to calculate a volume of fluid pumped through the cassette. The advantage here is that valves 202 and volumetric reference chambers 210a and 210b are placed in close proximity to each other and to the pneumatic pathways to membrane gasket 145.

For reference, side 204 of interface plate 185 in FIG. 23 shows actuation ports 198 and gasket seal ports 200 as described above in connection with FIGS. 20 and 21. In the illustrated embodiment, reference chambers 210a and 210b are blind wells formed in interface plate 185 with precision to have a fixed and known volume. In an embodiment, a controlled volume (weighed amount) of a highly thermally conductive material such as cooper mesh is placed in volumetric reference chambers 210a and 210b, which tends to counter a cooling effect created when high pressure air flows back from the pump chambers into the low pressure reference chambers 210a and 210b. Air within pressure reference chamber 210a and 210b quickly equilibrates to the temperature of the copper mesh and the walls of the reference chambers.

In FIG. 23, interface plate 185 is formed from a thermally conductive material, such as metal, e.g., aluminum, copper, steel or stainless steel. In the present system, the thermally conductive interface plate 185 is heated, e.g., by inductively producing a current that flows within interface plate 185, causing the plate to heat due to its bulk resistance. Alternatively a resistive heater is conductively coupled to plate 185, e.g., via heating strip 208.

Although not illustrated, a temperature sensing device, such as a thermistor or thermocouple is attached to the manifold, e.g., near reference chambers 210a and 210b. The temperature sensor sends a signal back to the processor or logic implementor, which controls a power supply supplying power to the resistive heater or the current providing device, such that the temperature of interface plate 185 is maintained steady at a desired temperature. In one embodiment, interface plate 185 is heated to about 36° or 37° C.

Figure 25A:
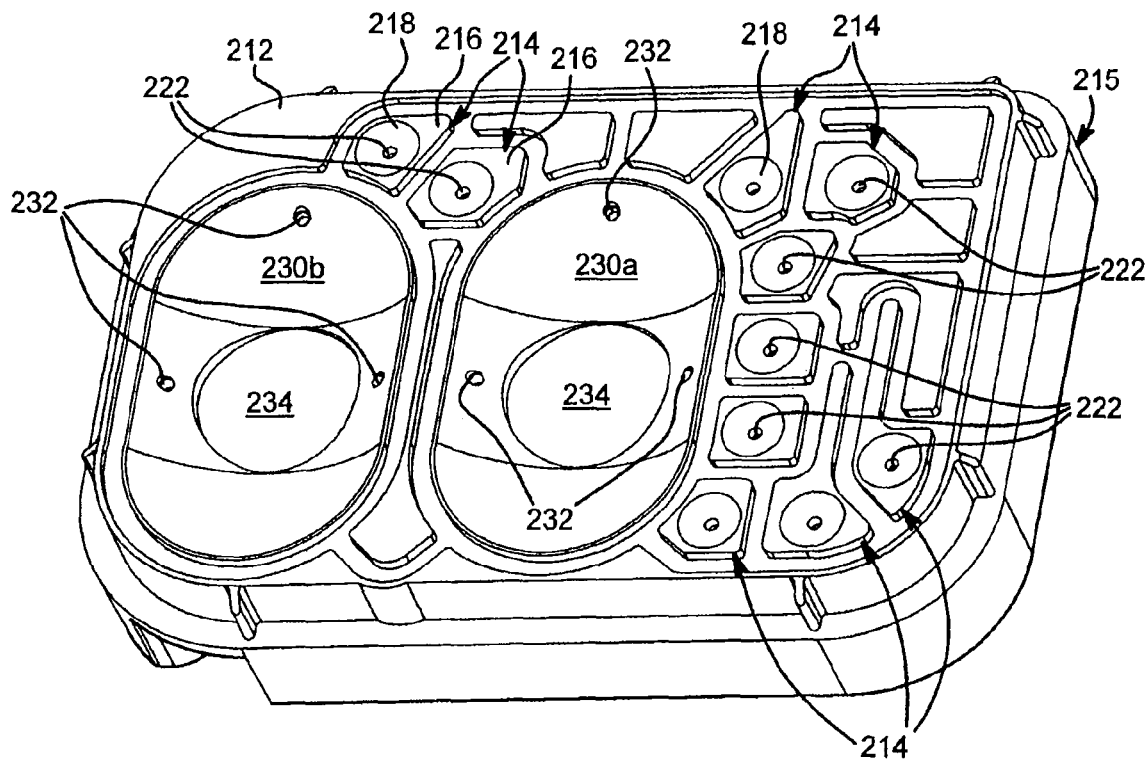
FIGS. 25A and 25B are front and rear perspective views of the plastic interface and control valve connection portion of the assembly of FIG. 24.
Figure 25B:
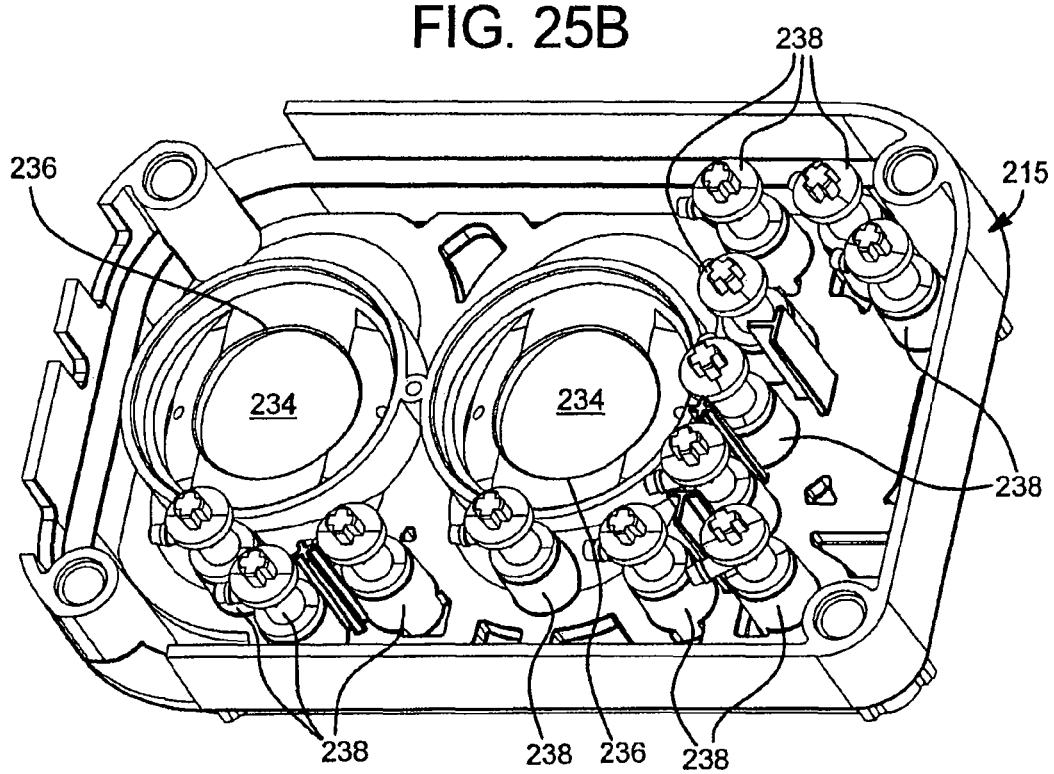
Figure 26A:
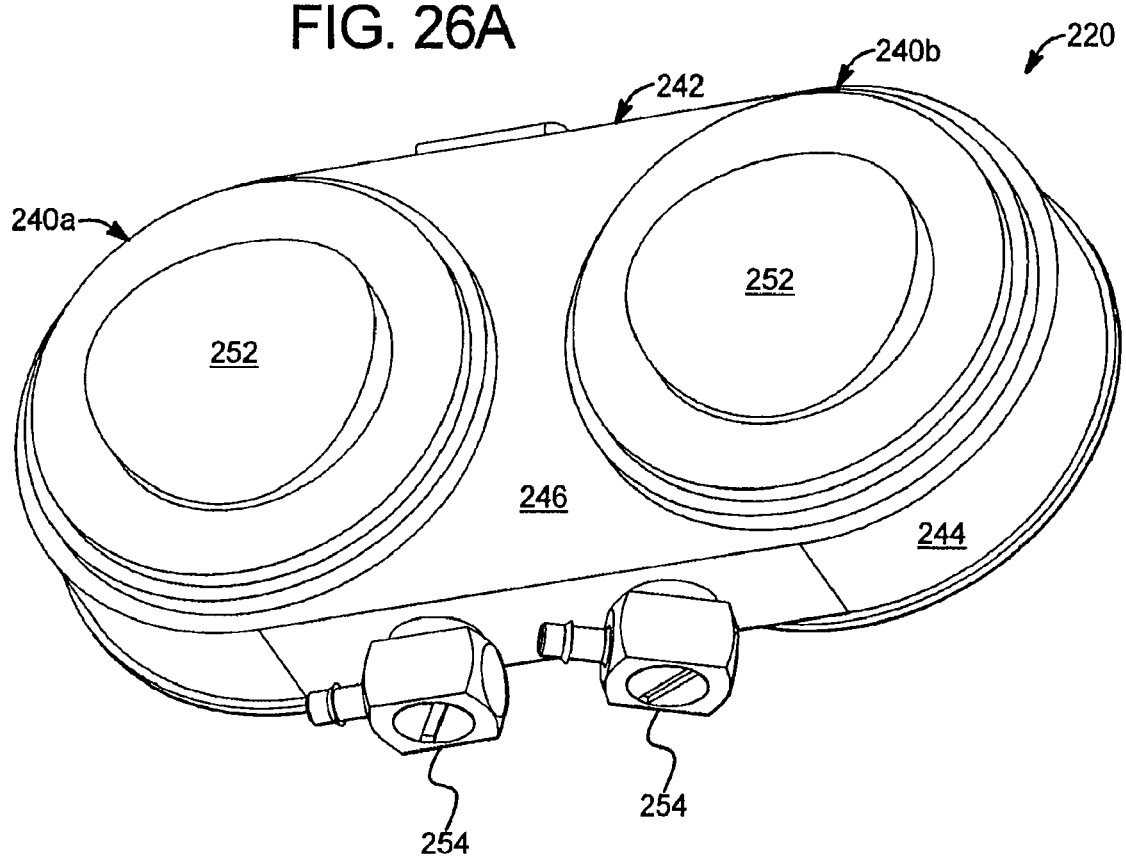
FIGS. 26A and 26B are front and rear perspective views of the heated reference chamber module of the assembly of FIG. 24.
Figure 26B:
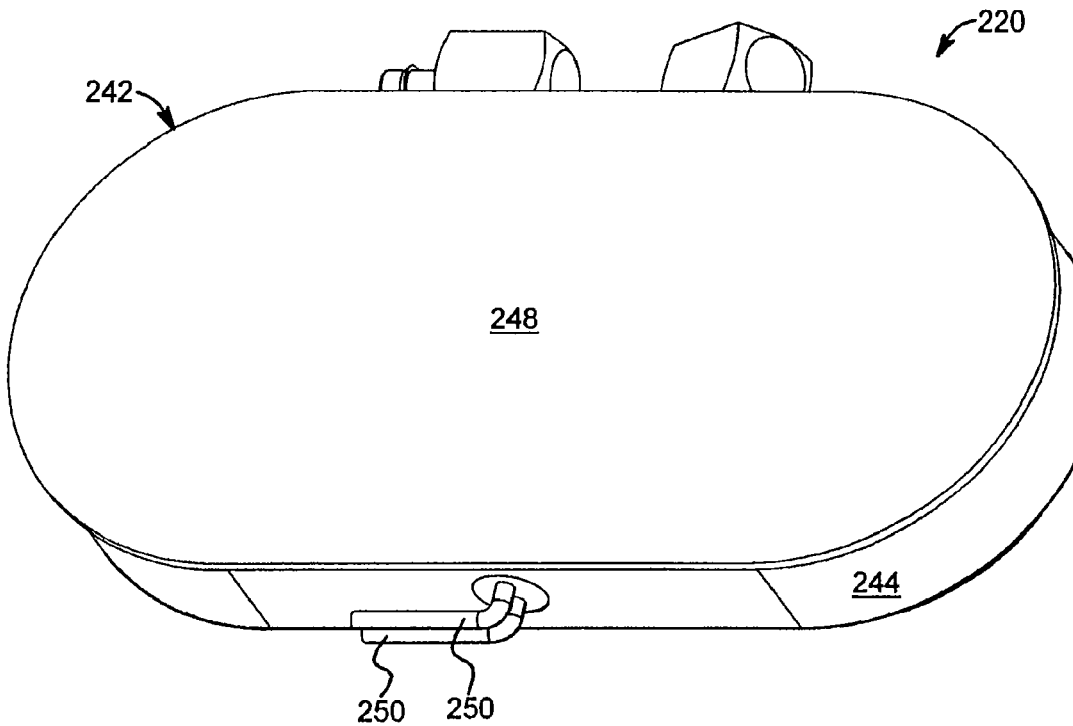

Referring now to FIGS. 24, 25A, 25B, 26A and 26B, system 210 illustrates an alternative heated cassette interface embodiment that connects to a remotely located valve manifold, such as that used in the HomeChoice® Pro APD System. System 210 includes alternative interface plate 215 and a separate heated reference chamber module 220. FIG. 24 illustrates module 220 attached to alternative interface plate 215. FIGS. 25A and 25B illustrate alternative interface plate 215 from the front and back, respectively. FIGS. 26A and 26B illustrate the reference chamber module 220 from the front and back, respectively.

Alternative interface plate 215 in one embodiment is made of plastic, such as injection molded ABS, Delrin®, Noryl®, polycarbonate or any other suitable plastic. A front surface 212 of plate 215 provides the cassette interface, which is shaped largely the same as the cassette interface of interface plate 185. Interface plate 215 includes a plurality of valve seats 214, each including a raised plateau 216. Plateaus 216 each form a downwardly angled or conical inset 218, which defines an actuation port 222. In the illustrated embodiment, gasket seal ports 200 are not illustrated. It should be appreciated however that gasket seal ports 200 could be added and that the membrane gasket 145 shown above can be employed with alternative interface plate 215.

Alternative interface plate 215 includes alternative pump wells 230a and 230b, which each include a plurality of actuation ports 232 and a conductive metal, e.g., aluminum or cooper, interface 234. Interfaces 234 are shown in the rear view of plate 215 in FIG. 25B as extending through an aperture 236 in the back of pump wells 230a and 230b. The conductive interfaces 234 contact the heated reference chambers of heated reference chamber module 220, such that heat from the heated reference chambers in turn heats conductive interfaces 234. Heated conductive interfaces 234 in turn heat air present between pump wells 230a and 230b and the mated membrane gasket.

FIGS. 24 and 25B show pneumatic fittings 238, which in one embodiment are connected to a remotely located valve manifold and to the molded plastic interface plate 215. Because fittings 238 direct positive and negative air flowing to the valve seats 214 (FIG. 25A) or 194 (FIG. 21) and to the valve wells 164 of membrane gasket 145, the temperature of this air is not relevant to volumetric pumping accuracy. That is, only the air flowing to the pump chambers 112 of cassette 140 needs to be heated. Accordingly, module 220 can be made in a relatively small package, which fits onto interface 215.

FIGS. 26A and 26B illustrate heated volumetric reference chamber module 220. As seen in FIG. 26A, volumetric reference chambers 240a and 240b are fitted into a casing 242 having a sidewall 244, a mounting plate 246 and a cover 248. Sidewall 244, mounting plate 246 and cover 248 can be made of metal or a thermally conductive plastic. Volumetric reference chambers 240a and 240b can be formed integrally as part of mounting plate 246 or be separate items attached to the mounting plate. Heating wires 250 run to a cartridge style heating element, such as those made by Watlow Electric Manufacturing Company (St. Louis, Mo.), Chromalox Corporation (Pittsburgh, Pa.) or Tempco Electric Heater Corporation (Wood Dale, Ill.) and fit into an, e.g., round, mounting aperture. Heating wires 250 can also run to resistive heating elements that can for example coil around or otherwise contact volumetric reference chambers 240a and 240b so as to heat the volumetric reference chambers conductively, convectively or via radiant energy. Again, a temperature sensor is incorporated into heated module 220, so as to provide feedback to a heating controller, which maintains the volumetric reference chambers at a steady and desired temperature, such as 36° or 37° C., or alternatively at an equilibrium or average operating temperature that the corresponding disposable cassette reaches when pumping dialysis fluid.

Volumetric reference chambers 240a and 240b each include a conductive interface 252, which mate with conductive interfaces 234 of pump wells 230a and 230b shown in FIGS. 25A and 25B. Conductive interfaces 252 are made of a thermally conducting material, such as copper or aluminum. Thus, it should be appreciated that heat from the heating elements is transferred to the reference chambers, which are also conductive aluminum or copper in one embodiment. Heat conducts to conductive interface 252, to conductive interfaces 234 and to the activation air, which is pumped back and forth from reference chambers 240a and 240b via valves or fittings 254, through actuation ports 232 of pump wells 230a and 230b of interface plate 215 to the membrane and gasket.

Although not shown, a suitable insulating material, can be dispersed around conductive reference chambers 240a and 240b and housing 242 of module 220. The insulating material can be insulating wool or fiberglass, for example. The insulative material can also be applied to the tubing running from fittings 254 to the remotely located valve manifold and back to the pump ports 232 over the relatively short tubing pathway to further minimize heat loss to the atmosphere. The close proximity of the pneumatic components also lends the configuration to being heated, which enables the components to be kept at a desired, stable temperature. These features reduce temperature related errors in measuring volume of fluid pumped using both the method of the '482 patent and the improved method discussed below. The remotely located valve manifold can also be heated to further improve volumetric accuracy. The embodiments shown in FIGS. 24 to 26 are more complex than the embodiments of FIGS. 19 to 23; however, the latter embodiments move the valves away from the cassette interface and allow the valves to be incased within a sound enclosure.

Real Time Volume Measurement

Figure 27:
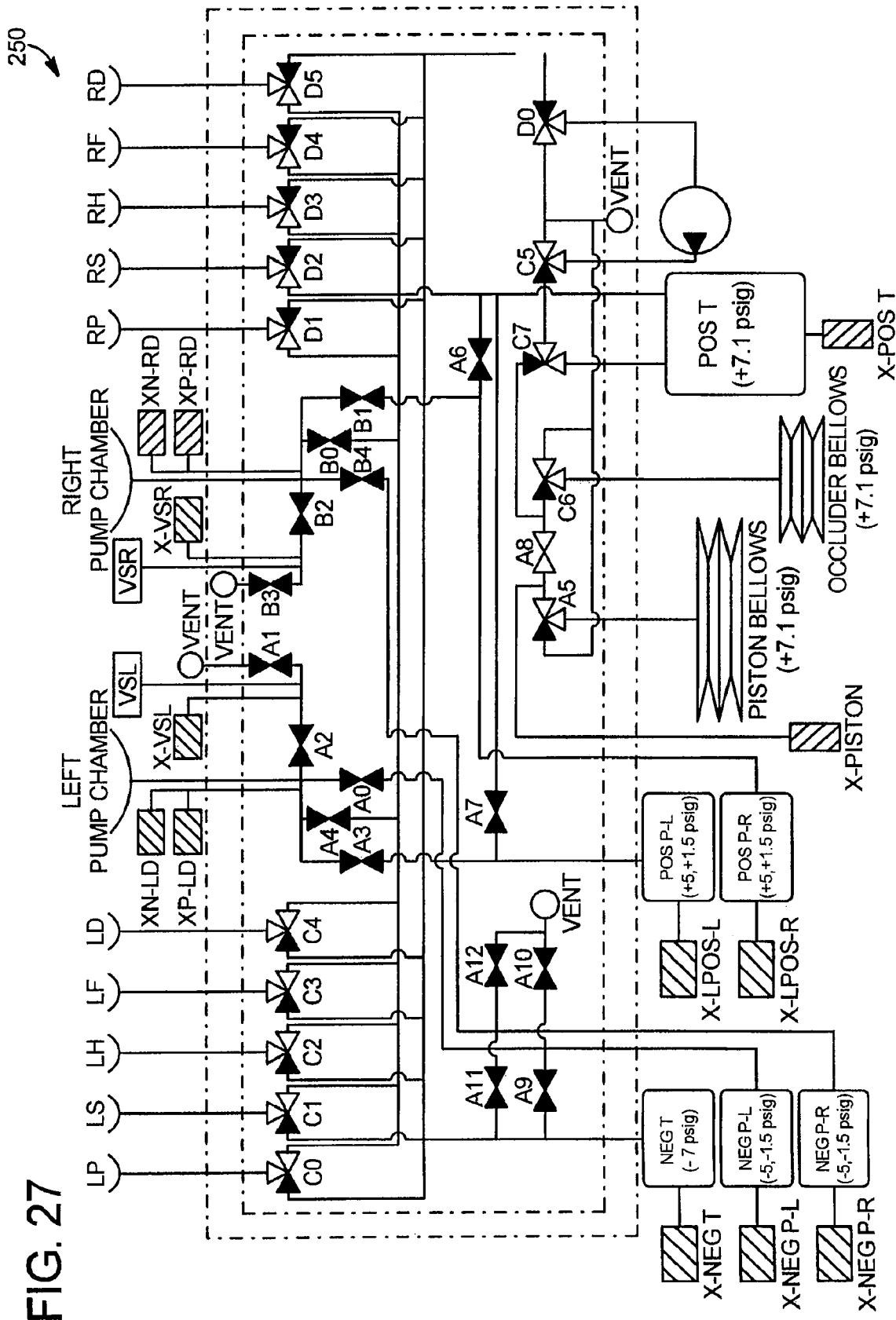
FIG. 27 is a schematic view of an embodiment of a pneumatic system for operating a real time method for determining volume of fluid moved.

Referring now to FIG. 27, system 250 illustrates one embodiment for a pneumatic control of dialysis system 10 described herein. The top of system 250 represents the components described above in connection with FIGS. 19 to 24, 25A, 25B, 26A and 26B. LP, LS, LH, LF, LD, RP, RS, RH, RF, RD represent the valve wells of the membrane gasket and the valve chambers of the disposable cassette. Although ten valves are described here and in FIGS. 19 to 24, 25A, 25B, 26A and 26B, more or less valves may be provided based on many factors, such as supply bag capability, whether or not admixing is supported and whether inline or batch heating is used.

The valving and pneumatic lines for gasket seal ports 200 are not shown in FIG. 27. As described above, ports 200 can be pressurized together such that one or a couple of valves in combination with a manifold running to each of ports 200 can control all the gasket seal ports 200.

Left and right pump chambers represent the pump wells of the manifold and pump chambers 112 of the disposable cassette. VSL and VSR are the volumetric reference chambers discussed above. As illustrated, pressure transducer X-VSL monitors the pressure in reference chamber VSL. Pressure transducer X-VSR monitors the pressure in reference chamber VSR.

Valves C0 to C4 and D1 to D5 are three way valves 238 shown in FIGS. 24 and 25B. Valves A0 and B4 are pump control valves 254 shown in FIG. 26A. The remainder of valves A, C and D are located elsewhere in instrument 20.

System 250 also includes a plurality of positive and negative pressure tanks, NEG T (negative pressure, communicates with chambers VSL and VSR), POS T (positive pressure, communicates with chambers VSL and VSR), NEG P-L (negative pressure, communicates with left pump chamber), NEG P-R (negative pressure, communicates with right pump chamber), POS P-L (positive pressure, communicates with left pump chamber), and POS P-R (positive pressure, communicates with right pump chamber). Separate pressure transducers X-NEG T, X-POS T, X-NEG P-L, X-NEG P-R, X-POS P-L, X-POS P-R monitor the pressure in the respective pressure tanks.

The separate pressure and vacuum reservoirs NEG P-L, NEG P-R, POS P-L and POS P-R allow a pressure (vacuum) decay to be measured as fluid is pushed from (pulled into) pumping chambers 112 as described in detail below.

For reference, a piston bellows, which can be located in the door of instrument 20, pushes the cassette against the interface plate and an occluder bellows which can unclamp all lines (fail closed) are shown. Both bellows and the occluder are actuated pneumatically in one embodiment.

System 250 also includes a processor or logic implementer operating with computer memory having program code configured to perform the below described real time method. System 250 can be operated with the heated manifolds discussed above, making the assumption of constant temperature a more correct assumption.

Referring now to FIGS. 28A to 28F, an improved method for measuring the volume of fluid pumped via pneumatic actuation is illustrated. FIGS. 28A to 28D illustrate by example how the volume of fluid moved is calculated after its has been moved. Valves shown blackened are closed, while non-shaded valves are open. The actions shown in FIGS. 28A and 28B occur during the relatively short rest measurement periods just prior to a pump-out stroke shown above in connection with FIGS. 18A to 18C. The actions shown in FIGS. 28C and 28D occur during the short rest measurement periods just after the pump-out strokes of FIGS. 18A to 18C.

The chamber is full of fluid in FIGS. 28A and 28B. In FIG. 28A, the valve (or valves) between chamber POS T and the pump chamber (e.g., left pump chamber) is (are) open. The valve (or valves) between the pump chamber e.g., the left pump chamber) and the associated volumetric reference chamber (e.g., VSL) is (are) closed. This allows the pump chamber to become pressurized to the pressure of POS T, e.g., 7 psig. A vent valve (e.g., A1 in FIG. 27) is opened such that the pressure in the volumetric reference chamber (e.g., VSL) is zero. Volumetric reference chamber (e.g., VSL) has a known volume of 16.5 milliliters in the illustrated embodiment.

In FIG. 28B, the valve states switch such that the valve (or valves) between chamber POS T and the pump chamber (e.g., left pump chamber) is (are) closed. The valve (or valves) between the pump chamber (e.g., the left pump chamber) and the associated volumetric reference chamber (e.g., VSL) is (are) opened. Vent valve (e.g., A1) is closed. This allows the pump chamber to pressurize the volumetric reference chamber (e.g., VSL) to 2.4 psig, causing the pump pressure to drop from 7 psig to 2.4 psig.

The processor is configured to calculate the volume of air or gas $V_{gas}$ behind the fluid pump chamber when full as follows:

$$V_{gas,full} = (P_{ref,final} - P_{ref,initial})/(P_{press1,initial} - P_{press1,final}) * V_{ref},$$

wherein $P_{ref,final}$ is a final pressure in the volumetric reference chamber (e.g., VSL) after the fluid pump is allowed to pressurize the volumetric reference chamber (e.g., VSL), 2.4 psig in the example;

$P_{ref,initial}$ is the initial pressure in the reference chamber before the fluid pump is allowed to pressurize the volumetric reference chamber (e.g., VSL), zero psig in the example;

$P_{pump, initial}$ is an initial pressure in the pressure chamber before the medical fluid pump is allowed to pressurize the volumetric reference chamber (e.g., VSL), here 7 psig. $P_{press1, final}$ is a final pressure in the pressure chamber after the medical fluid pump is allowed to pressurize the volumetric reference chamber (e.g., VSL), here 2.4 psig; and $V_{ref}$ is the volume of the reference chamber, here 16.5 milliliters.

Thus $V_{gas, full} = (2.4-0)/(7-2.4) * 16.5$ milliliters=8.6 milliliters.

Next, the valve chambers 114 of the disposable cassette are changed such that positive pressure from one of the pump stroke tanks POS P-L and POS P-R (illustrated in FIGS. 28E and 28F) pushes fluid from the pump chamber to the patient or drain. The pump-out stroke is performed in combination with the real time fluid volume measurement shown below in connection with FIGS. 28E and 28F. This is described below with the real time pressure decay method.

Next, as shown in FIG. 28C the chamber has already been emptied. The valve (or valves) between chamber X-POS T and the pump chamber (e.g., left pump chamber) is (are) open. The valve (or valves) between chamber X-POS T and the associated volumetric reference chamber (e.g., VSL) is (are) closed. This allows the pump chamber to become pressurized to the pressure of X-POS T, e.g., 7 psig. A vent valve (e.g., A1 in FIG. 27) is opened such that the pressure in the volumetric reference chamber (e.g., VSL) is zero. Volumetric reference chamber (e.g., VSL) has the known volume of 16.5 milliliters.

In FIG. 28D, the valve states switch such that valve (or valves) between chamber X-POS T and the pump chamber (e.g., left pump chamber) is (are) closed. The valve (or valves) between the pump chamber and the associated volumetric reference chamber (e.g., VSL) is (are) opened. Vent valve (e.g., A1) is closed. This allows the pump chamber to pressurize the volumetric reference chamber (e.g., VSL) to 4.2 psig, causing the pump pressure to drop from 7 psig to 4.2 psig.

The processor is configured to perform the same calculation as shown above, this time to calculate the volume of air or gas $V_{gas}$ behind the fluid pump chamber when empty:

$$V_{gas,empty} = (4.2-0)/(7-4.2) * 16.5 \text{ milliliters} = 24.75 \text{ milliliters}.$$

The volume of fluid pumped between the measurement periods of FIGS. 28B and 28C is then: fluid moved $V_{fluid}$=empty chamber air volume $V_{gas, empty}$—full chamber air volume $V_{gas, full}$ which is 24.75 milliliters −8.6 milliliters=16.15 milliliters. P Referring now to FIGS. 28E and 28F, the apparatus for performing a real time calculation of fluid pumped is illustrated. Here, pressure decay in the pressure tank driving the pump chamber during the pump-out stroke (POS P-L and POS P-R) is monitored in real time. The processor calculates the volume pumped in real time according to the equation: $V_{fluid,t} = (P_{POS\ P,\ initial}/P_{POS\ P,t} - 1)(V_{POS\ P} + V_{gas, full})$, wherein $P_{POS\ P, initial}$ is an initial pressure of the pressure tank POS P-L and POS P-R prior to the pump-out stroke;

$P_{POS\ P,t}$ is a pressure of the second pressure chamber at a time t during the pump-out stroke;

$V_{POS\ P}$ is a known volume of the second pressure chamber; and $V_{gas, full}$ is the calculated volume of gas in the pump chamber when full made above in connection with FIGS. 28A and 28B.

The steps of FIGS. 28E and 28F are made between the before and after calculations above, that is, between the steps of FIGS. 28B and 28C. In FIG. 28E, at the beginning of the pump-out stroke, the valve (or valves) between chamber POS T and the pump chamber (e.g., left pump chamber) is (are) closed. The valve (or valves) between chamber POS T and the associated volumetric reference chamber (e.g., VSL) is (are) closed. Vent valve (e.g., A1 in FIG. 27) is also closed. The volume of air in the pump chamber $V_{gas, full}$ is known to be 8.6 milliliters as discussed above in connection with FIG. 28B. The volume of fixed volume tank POS P-L or POS P-R is known, e.g., 500 milliliters. The initial pressure $P_{POS\ P, initial}$ is known, e.g., 1.5 psig.

The valve (or valves) between chamber POS P-L or POS P-R is (are) opened beginning the pump-out stroke. At this moment the pressure begins to decay. The processor is configured to sample the pressure readings ($P_{POS\ P,t}$) from pressure transducer X-POS P-L or X-POS P-R, for example every twenty milliseconds. The processor also calculates the real time amount of fluid pumped using the above equation and the measurement of $P_{POS\ P,t}$. FIG. 28F shows an end of the pump-out stroke and a corresponding end of the pressure decay.

FIG. 29 shows a chart of what the decay ($P_{POS\ P,t}$), and resulting fluid volume (milliliters) calculated according to the above equation, could look like over the pump-out stroke. For ease of illustration, only a few data points are shown. The pressure begins at the time that the pump-out stroke begins. Here, $P_{POS\,P,t} = P_{POS\,P,initial}$, such that the ratio of same is one, causing the first term in the equation and the resulting fluid volume pumped to be zero.

At the second pump stroke time in FIG. 29, $P_{POS\,P,t}$ has dropped to 16.1 psi (absolute), making the first term in the equation above equal to 0.0062, which when multiplied by the combined volume of tank POS P-L or POS P-R (500 milliliters) and the initial volume of air in the pump chamber (8.6 milliliters) yields an absolute volume pumped of (0.0062)*508.6=3.16 milliliters.

At the third pump stroke time in FIG. 29, $P_{POS\,P,t}$ has dropped to 16.00 psia, making the first term in the equation above equal to 0.0125, which when multiplied by the combined volume of tank POS P-L or POS P-R (500 milliliters) and the initial volume of air in the pump chamber (8.6 milliliters) yields an absolute volume pumped of (0.0125)*508.6=6.35 milliliters.

At the fourth pump stroke time in FIG. 29, $P_{POS\,P,t}$ has dropped to 15.90 psia, making the first term in the equation above equal to 0.0189, which when multiplied by the combined volume of tank POS P-L or POS P-R (500 milliliters) and the initial volume of air in the pump chamber (8.6 milliliters) yields an absolute volume pumped of (0.0189)*508.6=9.59 milliliters.

At the fifth pump stroke time in FIG. 29, $P_{POS\,P,t}$ has dropped to 15.80 psia, making the first term in the equation above equal to 0.0253, which when multiplied by the combined volume of tank POS P-L or POS P-R (500 milliliters) and the initial volume of air in the pump chamber (8.6 milliliters) yields an absolute volume pumped of (0.0253)*508.6=12.87 milliliters.

At the sixth and final pump stroke time in FIG. 29, which is also illustrated in FIG. 28F, $P_{POS\,P,t}$ has dropped to 15.70 psia (1.0 psig), making the first term in the equation above equal to 0.0318, which when multiplied by the combined volume of tank POS P-L or POS P-R (500 milliliters) and the initial volume of air in the pump chamber (8.6 milliliters) yields an absolute volume pumped of (0.0318)*508.6=16.19 milliliters.

The final absolute fluid volume moved or pumped via the real time algorithm, 16.19 milliliters, is virtually the same as the volume of fluid calculated via the before and after algorithm of FIGS. 28A to 28D, 16.15 milliliters (0.25% difference). The real time method however enables mid-pump stroke volumes to be known. As described above and shown below, there are many uses for the intermediate volumes including but not limited to determining: (i) if a full pump stroke has occurred; (ii) if a line occlusion has occurred; (iii) if a leak has occurred; and (iv) if multiple concentrates have been mixed properly, for example.

As discussed above, the real time fluid volume calculation can be used in combination with the before and after fluid volume calculation. It should be appreciated however that the real time fluid volume calculation does not have to be used in combination with the before and after fluid volume calculation. That is, after the determination of $V_{gas,\,full}$ in FIG. 28B, the system can perform the real time calculation shown in FIGS. 28E, 28F and 29, without thereafter doing the post stroke reference chamber pressurization and calculation. It is therefore expressly contemplated to not use the post stroke reference chamber pressurization and calculation, which would negate the need for the post stroke fluid measurement periods shown for example in connection with FIGS. 18A and 18B for both fill and empty strokes. The post stroke fluid measurement period can be eliminated for systems that have any number of pump chambers, e.g., one, two or three pump chambers.

FIGS. 28A to 28F and 29 show a pump-out stroke and associated fluid volume measurement. It should be appreciated that the above methodology also applies to a pump-in or fill stroke. Here, the same pump chamber (left or right) and reference chamber (VSL or VSR) are used. The main difference is that negative pressure is used to flex the cassette sheeting, pulling fluid from a supply or a patient into the pump chamber. Thus viewing FIG. 27, negative pressure tank NEG P-L or NEG P-R replaces the positive pressure tanks Pos P-L or Pos P-R in FIGS. 28E and 28F. Negative pressure would be used for example in the fresh fluid and drain fluid filling phases shown below in connection with FIGS. 30 and 31 discussed next. The POS T tank remains as shown in FIGS. 28E and 28F as it is used for fluid measurement after the fact (28A through 28D) and not in the real time fluid measurement.

Figure 30:
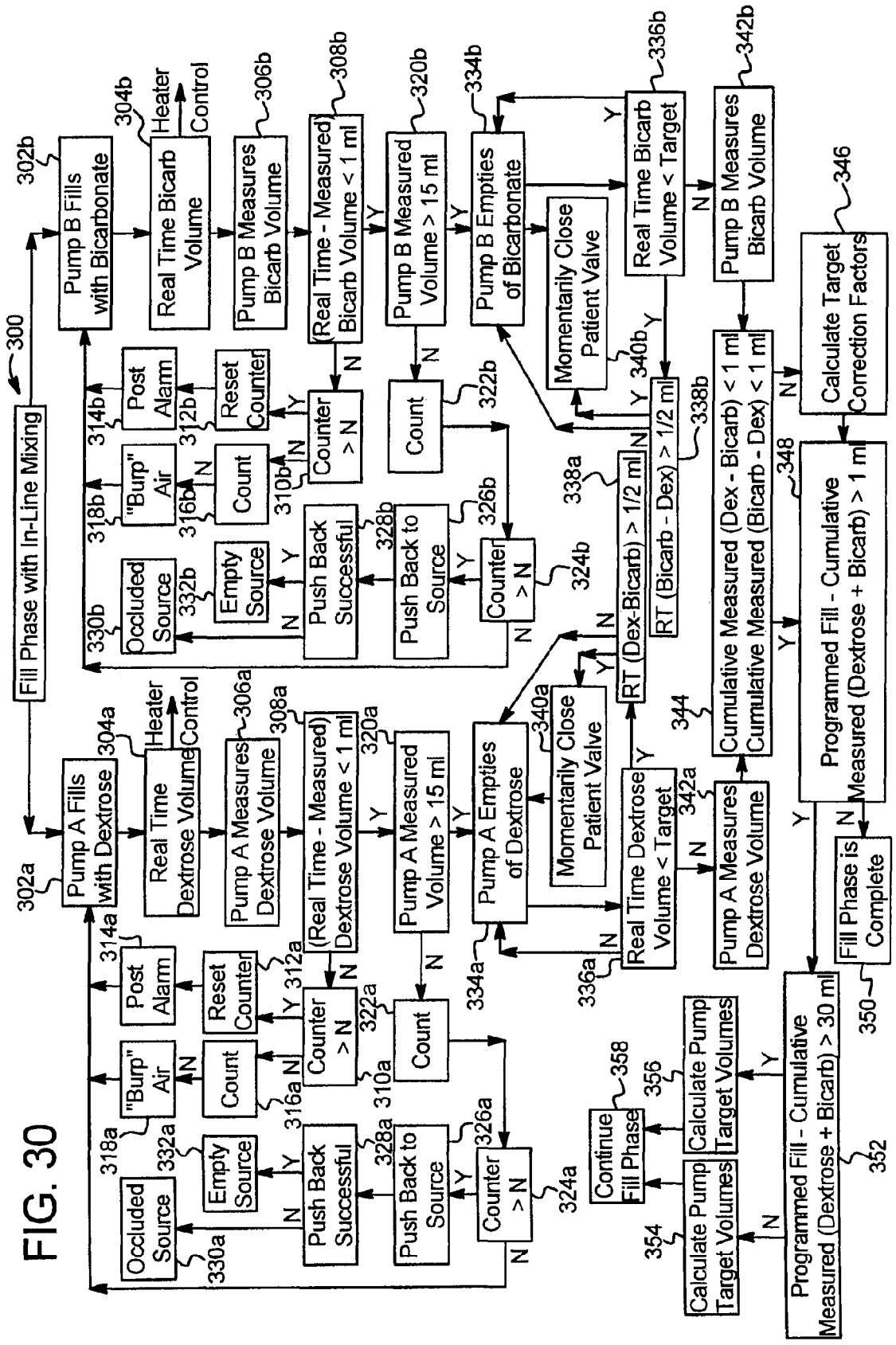
FIG. 30 is a schematic flow chart illustrating an example of pneumatically actuated pumps undergoing a fill with fresh fluid phase, using the real time method discussed in connection with FIGS. 28A to 28F, and wherein the dialysis system employs inline mixing of dextrose and bicarbonate concentrates.

Referring now to FIG. 30, the real time method above is used in connection with a filling method 300 for the filling of both pump chambers (left and right) in a dialysis system that employs an inline mixing of dextrose and bicarbonate concentrates to form a biocompatible dialysate for the patient, which is advantageous physiologically for the patient. For ease of illustration, it is assumed that left pump chamber, reference chamber VSL and negative pumping tank NEG P-L control the dextrose pumping. Right pump chamber, reference chamber VSR and negative pumping tank NEG P-R control the bicarbonate pumping. POS T is used for both pump chambers.

In step 302a and 302b, system 250 of FIG. 27 fills left pump chamber with dextrose and right pump chamber with bicarbonate. Here, it is assumed that the volume of air or gas in the pump chamber prior to the fill has been determined per the method of FIGS. 28A and 28B.

In step 304a and 304b, the real time calculation of dextrose and bicarbonate using the method described above in connection with FIGS. 28A to 28F is made. One purpose for doing the real time calculation is to determine flowrate. That is, the processor can be further configured to calculate the difference between the instant volume and a previously calculated volume to determine a real time flowrate so long as the time between measurements is known. For example in FIG. 29, the volume deltas are: 3.16 milliliters, 3.19 milliliters, 3.24 milliliters, 3.28 milliliters and 3.32 milliliters. Assuming the time between pressure readings or sample time to be the same between each sample, the above deltas show the flowrate of fluid during the pump out stroke to be gradually increasing (instantaneous rate=volume delta/sample time). This may be normal due to the configuration of the pneumatic pumping system or an anomaly of the particular pump stroke.

The real time flowrate information can be used for many purposes. One use is for control of the heater. Copending patent application entitled "Dialysis Fluid Heating Systems", filed Jul. 5, 2007, patent application Ser. No. 11/773,903, discloses a dialysis fluid heating control algorithm that uses flowrate feedback to control power to the fluid heating element. The flowrate information determined in connection with the real time volume calculations of step 304a and 304b is one way to provide the flowrate feedback to the referenced heating control algorithm.

In step 306a and 306b, the volume measurements of dextrose and bicarbonate using the before and after pump stroke method of FIGS. 28A to 28D is performed. In step 308a and 308b, the final real time volume is compared to the final before and after volume. If the difference between the two is outside of a particular amount (e.g., 1 milliliter), method 300 assumes that air is present in the associated pump chamber. The real time fluid flow measurement is essentially measuring the movement of the pumping chamber sheeting. The after the fact volumetric calculation only equals the real time measurement when no air is present within the pump chamber. If real time and after the fact measurements differ, air can be assumed to be present. If air is present, method 300 attempts to remove the air, which may require a couple of attempts. Method 300 tracks the number of attempts via a counter and eventually causes an alarm if air continues to be present.

A first step of the air purge subroutine is to determine if a counter is greater than a maximum amount of air removal tries N that method 300 is willing to make before determining that an alarm should be posted as seen in connection with step 310*a* and 310*b*. If counter is greater than N (test could alternatively be whether the counter is equal to N), and the allotted number of air removal procedures has been exceeded, method 300 resets the counter in step 312*a* and 312*b*, and posts an alarm in step 314*a* and 314*b*, e.g., an "air in the system alarm", which can be at least one of an audio alarm, visual alarm, audiovisual alarm, signal sent to a nurse, operator, pager or control center. The user can clear the alarm and resume the therapy. The procedure beginning at step 302*a* and 302*b* is then repeated. The alarm may or may not reappear.

If counter is less than or equal to N (test could alternatively be whether the counter is less than N), and the allotted number of air removal procedures has not been exceeded, method 300 increases the count by one in step 316*a* and 316*b* and causes instrument 20 to perform an "air purge" procedure in step 318*a* and 318*b*, which can for example involve opening the drain line valve and "burping" the air out of a port of the pump chamber and into the drain line. The procedure beginning at step 302*a* and 302*b* is then repeated.

Returning to the real time volume versus the before and after volume comparison of step 308*a* and 308*b*, if the difference between the two is inside of a particular range (e.g., 0 to 1 milliliter), method 300 next determines whether the fill was a complete fill in step 320*a* and 320*b*. For example, if the volume defined between the cassette pump chambers 112 and the pump wells of the interface plate when mated is 16.5 milliliters, method 300 can look to see whether the total volume delivered meets or exceed some amount close to the defined volume, e.g., fifteen milliliters. To perform this step, method 300 can look to the real time total volume, the before and after volume or both.

If not enough fluid has been drawn into the pump chamber, e.g., volume is less than fifteen milliliters and the number of attempts has been exceeded a maximum number of attempts (step 322*a* or 322*b*), method 300 checks if a line kink or other fluid flow obstruction is present and attempts to unkink the line or otherwise remove the occlusion. To do so again may take a couple of tries. Method 300 tracks the number of occlusion removal tries in steps 324*a* and 324*b*. If no kink or occlusion is present, the fluid source can be determined to be empty.

A first step of the occlusion removal subroutine is to increment a count in step 324*a* and 324*b*. A next step is to determine if the count is greater than a maximum amount of occlusion removal tries N that method 300 is willing to make before determining that an alarm should be posted. If counter is greater than N (test could alternatively be whether the counter is equal to N), and the allotted number of occlusion removal procedures has been exceeded, method 300 posts a continuous alarm that the operator needs to correct before therapy can continue.

If counter is less than or equal to N (test could alternatively be whether the counter is less than N), and the allotted number of occlusion removal procedures has not been exceeded, method 300 causes instrument 20 to perform an "occlusion removal" procedure in step 326*a* and 326*b*, which can for example involve pushing fluid back to its source or bag in step 326*a* and 326*b* in an attempt to unkink the line or bag port. A pushback is a push of a pump chamber of fluid back towards the source solution bag that is not allowing the pump chamber to fill with fluid. The pushback will fail if fluid cannot flow back to the source indicating that the source line is kinked or occluded. A real time pressure decay, or lack thereof, can be used to monitor the pushback flow, or lack thereof.

If the pushback is not successful as determined in connection with step 328*a* and 328*b*, system 300 determines that the source is occluded in step 330*a* and 330*b*. If the pushback is successful as determined in connection with step 328*a* and 328*b*, the source is determined to be empty in step 332*a* and 332*b*. Once an occluded source or empty source is detected, system 300 can cause an audible or visual alarms to be posted. System 300 can cause the fill to resume automatically one or two times before posting a non-recoverable alarm that requires user intervention. The counter in step 322*a* and 322*b* keeps track of the number of times the pushback attempt is made.

In step 334*a* and 334*b*, left and right pump chambers empty their respective concentrates into a line that connects to the patient, which is long enough for the concentrates to mix sufficiently before the dialysate is delivered to the patient. In steps 336*a* and 336*b*, method 300 determines using the real time fluid volume method of FIGS. 28A to 28F whether the total dextrose volume delivered has reached the targeted dextrose pump stroke volume delivered and whether the total bicarbonate volume delivered has reached the targeted bicarbonate pump stroke volume delivered, respectively.

If the targeted dextrose volume delivered has not been met in step 336*a*, fluid delivery continues and method 330 determines whether the "real time" (dextrose−bicarb) volume difference is greater than ½ milliliters in step 338*a*. If not, left pump chamber continues its emptying of dextrose at step 334*a*, causing the real time evaluation of step 336*a* to be made again. If real time (dextrose−bicarb) volume difference is greater than ½ milliliter in step 338*a*, the left patient valve (LP in FIG. 27) is closed momentarily to prevent the left pump chamber from proceeding too far ahead of the right pump stroke volume delivered in step 340*a*. Once the volume delivered by the left and right pump chambers is within ½ milliliter, the left pump chamber will resume its emptying of dextrose in step 334*a*, causing the real time evaluation of step 336*a* to be made again. Delivery of fluid from the left pump will stop when the left pump chamber has emptied, such that the target pump stroke volume has been delivered.

If the target bicarbonate volume delivered has not been met in step 336*b*, method 330 determines whether a real time (bicarbonate−dextrose) volume difference is greater than ½ milliliter in step 338*b*. If not, right pump chamber continues to empty bicarbonate again in step 334*b*, causing the real time evaluation of step 336*b* to be made again. If real time (bicarbonate−dextrose) volume difference is greater than ½ milliliter in step 338*b*, the right patient valve (RP in FIG. 27) is closed momentarily to prevent the right pump chamber from proceeding too far ahead of the left pump stroke volume in step 340*b*. Once the volume delivered by the left and right pump chambers is within ½ milliliter, right pump chamber resumes its emptying of bicarbonate in step 334*b*, causing the real time evaluation of step 336*b* to be made again. Delivery of fluid from the right pump will stop when the right pump chamber has emptied, such that the target pump stroke volume has been delivered.

Once the dextrose and bicarbonate target pump empty volumes are met in steps 336a and 336b, respectively, the processor measures the total volumes delivered using the before and after sequence of FIGS. 28A to 28D for dextrose and bicarbonate in steps 342a and 342b, respectively. In step 344, the processor determines whether a cumulative measured dextrose-bicarbonate volume is less than a threshold difference, e.g., one milliliter. The processor also determines whether a cumulative measured bicarbonate-dextrose volume is less than a threshold, e.g., one milliliter. In essence, the processor is determining whether the cumulative delivered volumes of dextrose and bicarbonate are within 1 milliliter.

If the cumulative delivered volumes when compared are outside of the threshold range, the processor adjusts the volume for the next pump stroke by calculating a correction factor in step 346. For example, if the normal target pump stroke volume is 15 milliliters, the system 300 will actually deliver a volume of 15 minus the correction factor for the dextrose. If the cumulative dextrose delivered volume exceeds the cumulative delivered bicarbonate volume by 1.2 milliliters, the correction factor is 1.2 milliliters and the next target stroke volume for dextrose is 15−1.2 milliliters=13.8 milliliters.

The correction factor is similar when bicarbonate delivered is greater than dextrose delivered by 1 milliliter or more. The correction factor is zero when the cumulative dextrose delivered is less than cumulative bicarbonate delivered.

After step 346, or if the cumulative pump empty volumes when compared are inside of the threshold range, the processor determines whether the sum of the cumulative dextrose and bicarbonate pump empty volumes is within a range (e.g., one milliliter) of a prescribed or programmed total dextrose and bicarbonate fill volume in step 348. If the measured total is within range of the prescribed total, fill phase is complete in step 350.

If the measured total is outside the range of the prescribed total, the processor determines whether the cumulative measured volume is less than the prescribed pump empty volume by more than the next scheduled set of pump strokes, e.g., 30 milliliters, in step 352. If it is, another set of pump strokes is delivered and step 352 is reached again. Steps 354 and 356 calculate the targeted fill volume for the next set of pump strokes. Step 356 calculates each targeted volume at 15 milliliters less the correction factors calculated in step 346. Step 354 calculates the fill volume to be ½ of the remaining volume (programmed fill−cumulative measured dextrose and bicarbonate). If the remaining volume is 20 milliliters, and the correction factor for dextrose is 1.2 milliliters, the next stroke target volumes for the last set of pump strokes are calculated to be, for example:

(20 milliliters+1.2 milliliters)/2−1.2=9.4 milliliters for dextrose (20 milliliters+1.2 milliliters)/2−0=10.6 milliliters for bicarbonate The target set of pump stroke volumes adds up to 20 milliliters while correcting the cumulative volume of dextrose so that the cumulative dextrose volume equals the cumulative volume of bicarbonate.

Figure 31:
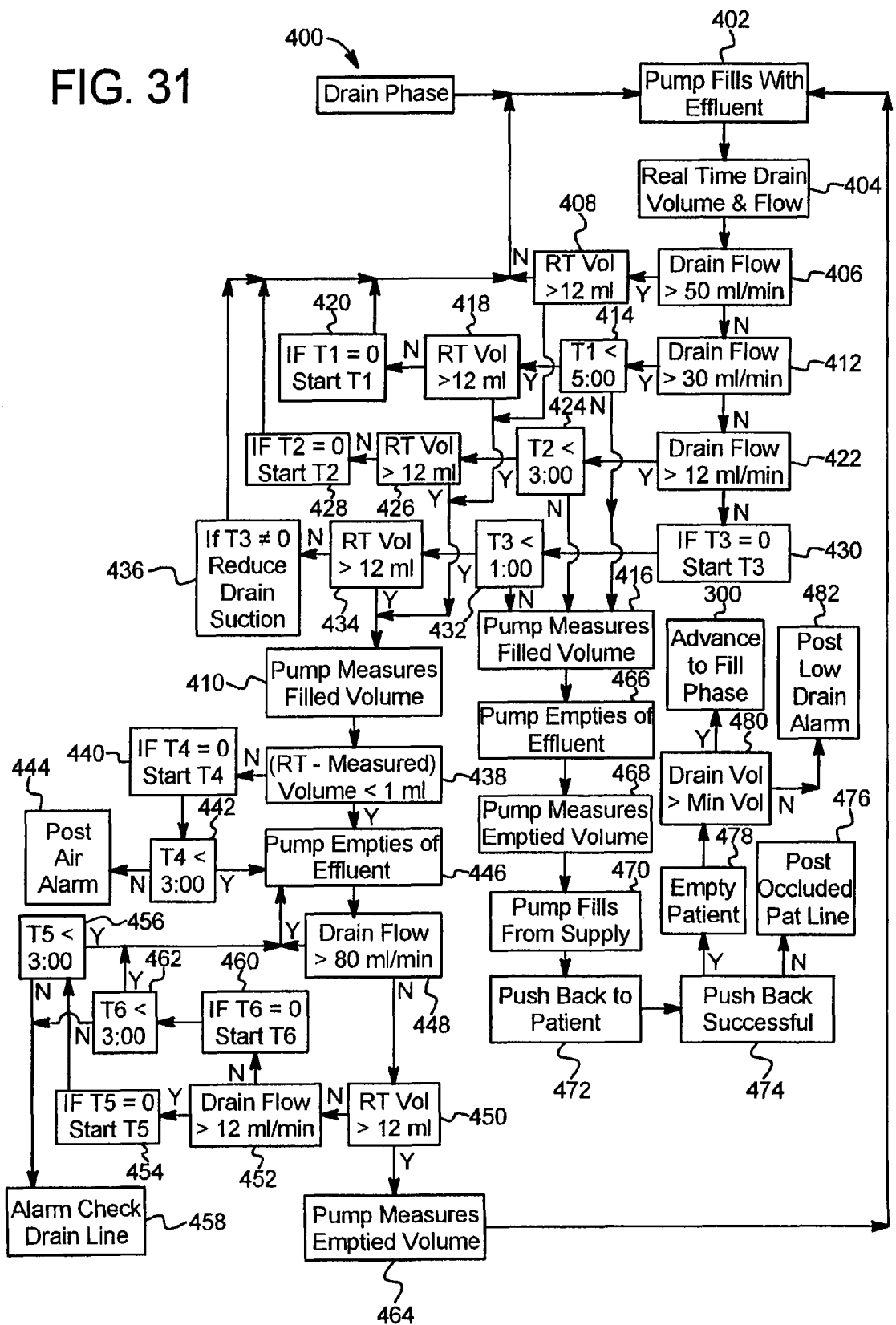
FIG. 31 is a schematic flow chart illustrating an example of the pneumatically actuated pumps undergoing a fill with effluent (draining fluid from the patient) phase, using the real time method discussed in connection with FIGS. 28A to 28F.

Referring now to FIG. 31, the real time method above is illustrated in connection with a draining method 400 for the filling of one of the pump chambers (left or right) with effluent fluid from the patient. For ease of illustration, left pump chamber, reference chamber VSL and negative pumping tank NEG P-L are used in this example. Right pump chamber, reference chamber VSR and negative pumping tank NEG P-R would be performing the same method simultaneously, but asynchronously so that the right pump chamber is filling with effluent when left pump system is emptying and vice versa.

Draining method 400 determines if the drain is flowing properly and if air is present. In step 402, left pump chamber is filled with effluent. In step 404, the processor determines the real time effluent volume and flow for the fill in the manner described above. In step 406, if flowrate is greater than a normal flow minimum rate threshold, e.g., 50 milliliters/minute, method 400 determines whether the real time volume calculation of effluent fill exceeds a minimum pump stroke volume threshold, e.g., 12 milliliters, in step 408. If not, left pump chamber continues to fill with effluent in step 402, forming a loop that cycles until the real time volume calculation of effluent fill exceeds the threshold in step 408.

When the real time volume calculation of effluent fill exceeds the threshold in step 408, the measurement of the effluent fill volume using the before and after pump stroke method of FIGS. 28A to 28D is performed in step 410. If the real time fluid volume moved is greater than the before and after stroke method of FIGS. 28A to 28D, air may have been drawn into the pump chamber when the chamber filled with fluid. The before and after pump stroke method of 28A to 28D will not be able to distinguish a pump chamber that contains 13 milliliters of fluid and 2 milliliters of air from a pump chamber that contains only 13 milliliters of fluid because the air will compress regardless of which side of the flexible sheeting it resides on, resulting in the same volume calculation. However, the flexible sheeting will move more when it accepts 13 milliliters of fluid and 2 milliliters of air than it would if it had only accepted 13 milliliters. The HomeChoice®System marketed by eventual assignee of the present disclosure attempts to complete the fill of the pump chamber using an alternate source if the pump chamber fill volume is more than 3 milliliters short of the full volume. If the HomeChoice® System cannot fill the pump chamber completely, air is assumed to be present. The contents of the pump chamber are then pumped to drain to eliminate the air. The HomeChoice® System remedy accordingly wastes time and fluid. The pump air detection and discharge regime occurring after step 410 is discussed below as step 438 eliminates.

Returning to step 406, if flowrate calculated via the real time calculation is less than the normal flow minimum rate threshold, e.g., 50 milliliters/minute, method 400 determines if the real time flowrate is greater than an intermediate or low flowrate threshold, e.g., 30 milliliters/minute, in step 412. If the real time flowrate is greater than the intermediate threshold, method 400 determines if a time T1 at which the flowrate is between the intermediate and high-end thresholds (e.g., between 30 and 50 milliliters/minute) is less than a preset time, e.g., 5:00 minutes in step 414. If the flowrate has remained between the intermediate and high-end thresholds for longer than the preset time, method 400 assumes that the patient line may be partially occluded and will attempt to clear the line pushing fresh dialysate toward the patient. If the pushback is unsuccessful an alarm will be posted (step 476). If the pushback is successful (determined via the volume using the before and after pump stroke method of FIGS. 28A to 28D in step 416) the method either advances to fill (step 300) or posts a low drain volume alarm (step 482). This routine is discussed in detail below.

If the flowrate has remained between the intermediate and high-end thresholds for less than the preset time, method 400 determines whether the real time volume calculation of effluent fill exceeds a threshold, e.g., 12 milliliters, in step 418. If not, timer T1 beginning at zero seconds is initiated in step 420 and left pump chamber continues to fill with effluent in step 402, forming a loop that cycles until (i) T1 reaches the preset time (e.g., five minutes) in step 414 or (ii) the real time volume calculation of effluent fill exceeds the threshold (e.g., 12 milliliters) in step 418.

When the real time volume calculation of effluent fill exceeds the threshold in step 418, the measurement of the effluent fill volume using the before and after pump stroke method of FIGS. 28A to 28D is performed in step 410. The pump air detection and discharge regime occurring after step 410 is discussed below at step 438.

Returning to step 412, if flowrate calculated via the real time calculation is less than the intermediate threshold, e.g., 30 milliliters/minute, method 400 determines if the real time flowrate is greater than a low end no-flow flowrate threshold, e.g., 12 milliliters/minute, in step 422. If the real time flowrate is greater than the low end threshold, method 400 determines if a time T2, at which the flowrate is between the low end and intermediate thresholds (e.g., between 12 and 30 milliliters/minute), is less than a second preset time, e.g., 3:00 minutes in step 424. In the illustrated embodiment T2 is less than T1, meaning method 400 does not wait as long at the lower flowrate before running the occlusion routine at step 416 because an occlusion is more likely at the lower flowrate.

If the flowrate has remained between the low end and intermediate thresholds for longer than the second preset time, method 400 assumes that the patient line may be partially occluded and attempts to clear the line by pushing fresh dialysate towards the patient. If the pushback is unsuccessful an alarm is posted at step 476. If the pushback is successful (determined by measuring the pump fill volume using the before and after pump stroke method of FIGS. 28A to 28D in step 416), the pump advances to fill (step 300) or posts a low drain volume alarm (step 482). This routine is discussed in detail below.

If the flowrate has remained between the low end and intermediate thresholds for less than the second preset time T2, method 400 determines whether the real time volume calculation of effluent fill exceeds a threshold, e.g., 12 milliliters, in step 426. If not, timer T2 beginning at zero seconds is initiated in step 428 and left pump chamber continues to fill with effluent in step 402, forming a loop that cycles until (i) T2 reaches the preset time (e.g., three minutes) in step 424 or (ii) the real time volume calculation of effluent fill exceeds the threshold (e.g., 12 milliliters) in step 426.

When the real time volume calculation of effluent fill exceeds the threshold in step 426, the measurement of the effluent fill volume using the before and after pump stroke method of FIGS. 28A to 28D is performed in step 410. The pump air detection and discharge regime occurring after step 410 is discussed below at step 438.

Returning to step 422, if flowrate calculated via the real time calculation is less than the low end no-flow threshold, e.g., 12 milliliters/minute, method 400 initiates a third timer T3 if the timer has not yet been initiated in step 430. If the real time flowrate is less than the low end threshold, method 400 determines if a time T3 at which the flowrate is less than the low end threshold is less than a third preset time, e.g., 1:00 minute in step 432. In the illustrated embodiment T3 is less than T2, meaning method 400 does not wait as long at the low end flowrate before running the occlusion routine at step 416 because an occlusion or an empty patient is more likely at the lower flowrate.

If the flowrate has remained under the low end threshold for less than the second preset time T3, method 400 determines whether the real time volume calculation of effluent fill exceeds a threshold, e.g., 12 milliliters, in step 434. If not, and timer T3 is not equal to zero seconds, method 400 causes left pump chamber to reduce suction pressure in step 436 (e.g., by changing NEG P-L from −1.5 psig to −1.2 psig as indicated in the pneumatic system 250 of FIG. 27).

At step 436 the patient is likely close to being empty or fully drained. To reduce discomfort in pulling the remaining effluent out of the patient, method 400 lowers the suction pressure in step 436. Left pump chamber continues to fill with effluent in step 402, forming a loop that cycles until (i) T3 reaches the preset time (e.g., one minute) in step 432 or (ii) the real time volume calculation of effluent fill exceeds the threshold (e.g., 12 milliliters) in step 434.

When the real time volume calculation of effluent fill exceeds the threshold in any of steps 408, 418, 426 or 434, the measurement of the effluent fill volume using the before and after pump stroke method of FIGS. 28A to 28D is performed in step 410 and a pump air detection check is performed. Here, method 400 calculates the difference between the real time calculation of effluent removed from the patient via the method of FIGS. 28A to 28F and the volume calculated using the before and after pump stroke method of FIGS. 28A to 28D. If the volume difference is less than a threshold difference (e.g., 1 milliliter) in step 438, the system assumes that little or no air is present and that normal pumping can continue because any air that may be present will not pass through the pump.

If the difference determined in step 438 is greater than the threshold, method 400 initiates a fourth timer T4 in step 440 if the timer has not yet been initiated. If the difference has remained out of range for greater than a fourth preset time (e.g., three minutes) as determined in step 442, method 400 posts an air alarm in the system alarm in step 444. If (i) the difference has not remained out of range for greater than the fourth preset time as determined in step 442 or (ii) the difference between the real time and before/after volumes is less than the threshold, method 400 causes left pump chamber to empty the effluent to drain in step 446. However, if T4 is greater than three minutes, the system assumes that the pump chamber has been ingesting air from the patient for three minutes and posts an alarm at step 444.

Step 448 creates a loop in which left pump chamber continues to empty to drain as long as the drain flow is greater than a threshold value, e.g., 80 milliliters/minute. When drain flow falls below the threshold, method 400 determines if the real time volume calculation of effluent sent to drain exceeds a threshold volume, e.g., 12 milliliters, in step 450. If not, method 400 determines if drain flow has fallen below a low end threshold, e.g., 12 milliliters/minute, in step 452.

If drain flow has not fallen below the low end threshold in step 452, a longer timer T5 is initiated if not initiated already in step 454. A loop is created as long as real time volume is less than the threshold, e.g., 12 milliliters, and drain flow remains above the low end threshold, e.g., 12 milliliters/minute and below the upper threshold, e.g., 80 milliliters/minute until timer T5 reaches a fifth (longer) preset time (e.g., three minutes) in step 456, at which time method 400 sends an alarm (audio, visual or audiovisual) to check the drain line for an occlusion in step 458.

If drain flow has fallen below the low end threshold in step 452, a shorter timer T6 is initiated if not initiated already in step 460. Another loop is created as long as real time volume is less than the threshold, e.g., 12 milliliters, and drain flow remains below the low end threshold, e.g., 12 milliliters/minute, until timer T6 reaches a sixth (shorter) preset time (e.g., thirty seconds) in step 462, at which time method 400 sends the alarm to check the drain line for an occlusion in step 458.

When drain flow falls below the threshold in step 448 and the real time volume calculation of effluent sent to drain exceeds a threshold volume, e.g., 12 milliliters, in step 450, method 400 calculates the total effluent volume sent to drain via the before and after method of FIGS. 28A to 28D as seen in step 464, after which left pump chamber begins another fill of effluent at step 402.

When any of the timers T1, T2 or T3 times out in steps 414, 424 or 432, respectively, it is possible that the patient line has an occlusion, which could for example be due to fibrin blockage or a partially kinked line. At step 416, method 400 calculates the total effluent pulled from the patient during the current pump stroke using the before and after method of FIGS. 28A to 28D. In step 466, left pump chamber empties the effluent to drain. In step 468, the total effluent volume sent to drain via the before and after method of FIGS. 28A to 28D is calculated, after which left pump chamber pulls a bolus of fresh fluid from a supply bag in step 470.

Left pump chamber pushes the fresh bolus to the patient via the patient line to verify that fill can be performed and to remove any fibrin blockage or to un-kink the patient line if it is partially occluded due to a kink in step 472. If the pushback procedure is not successful, e.g., fluid cannot reach the patient or real time flowrate is below a threshold, as determined in step 474, method 400 in step 476 posts a patient line occluded alarm via any of the ways discussed above. If the procedure is successful, e.g., fluid reaches the patient and/or real time flowrate is above a threshold, as determined in step 474, method 400 assumes that the patient is empty at step 478.

After the patient is determined to be empty in step 478, a total volume of effluent pulled from the patient is calculated and compared to a minimum drain volume in step 480. If total effluent volume is less than a minimum volume, a low drain alarm is posted in step 482 via any of the techniques described above. If total effluent volume reaches or exceeds the minimum volume, system 10 employing method 400 advances to the fill phase 300 described above in connection with FIG. 30. The minimum volume can be a percentage of the programmed fill volume when draining to empty. When draining to a target volume, for example with a tidal therapy, the minimum volume is the target volume. Method 400 also monitors the cumulative volume of effluent drained after step 410. This cumulative volume is reported as the volume drained when a tidal drain ends while under a normal flow condition. Otherwise, the cumulative drain volume from step 480 is reported as the volume drained.

Temperature Sensor

Figure 32:
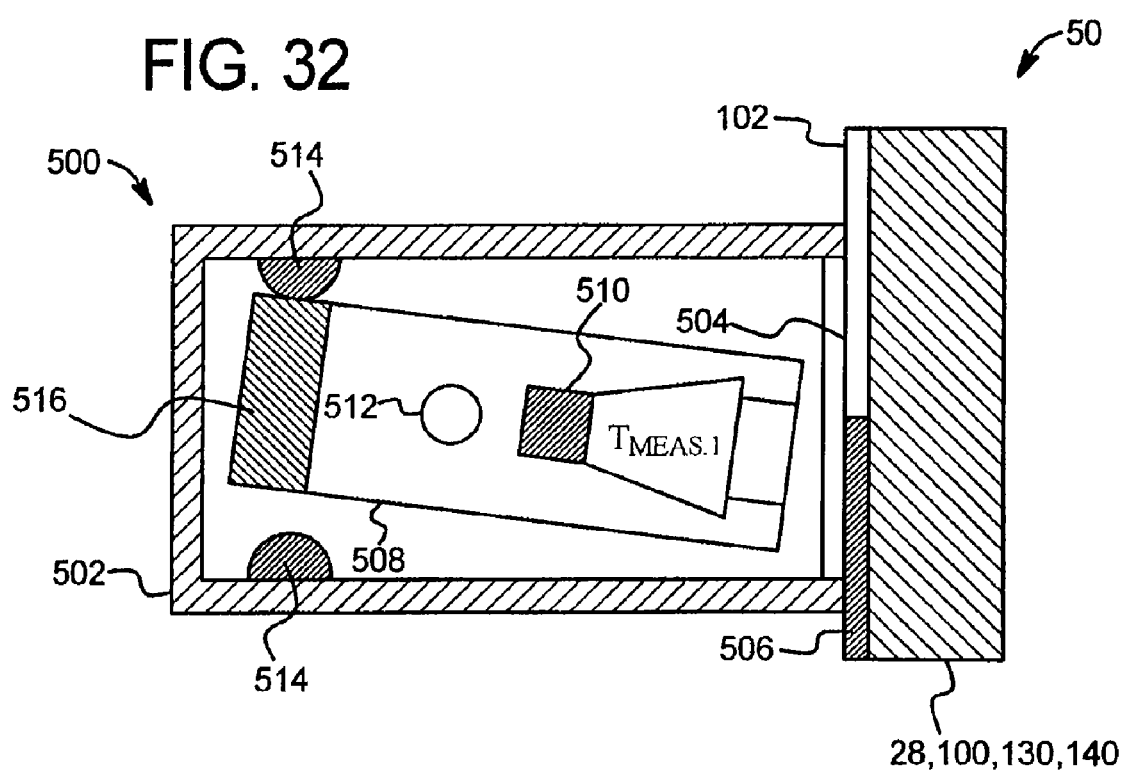
FIG. 32 is a schematic view of one embodiment for a non-invasive temperature sensing system and method having a temperature sensor in a first position.
Figure 33:
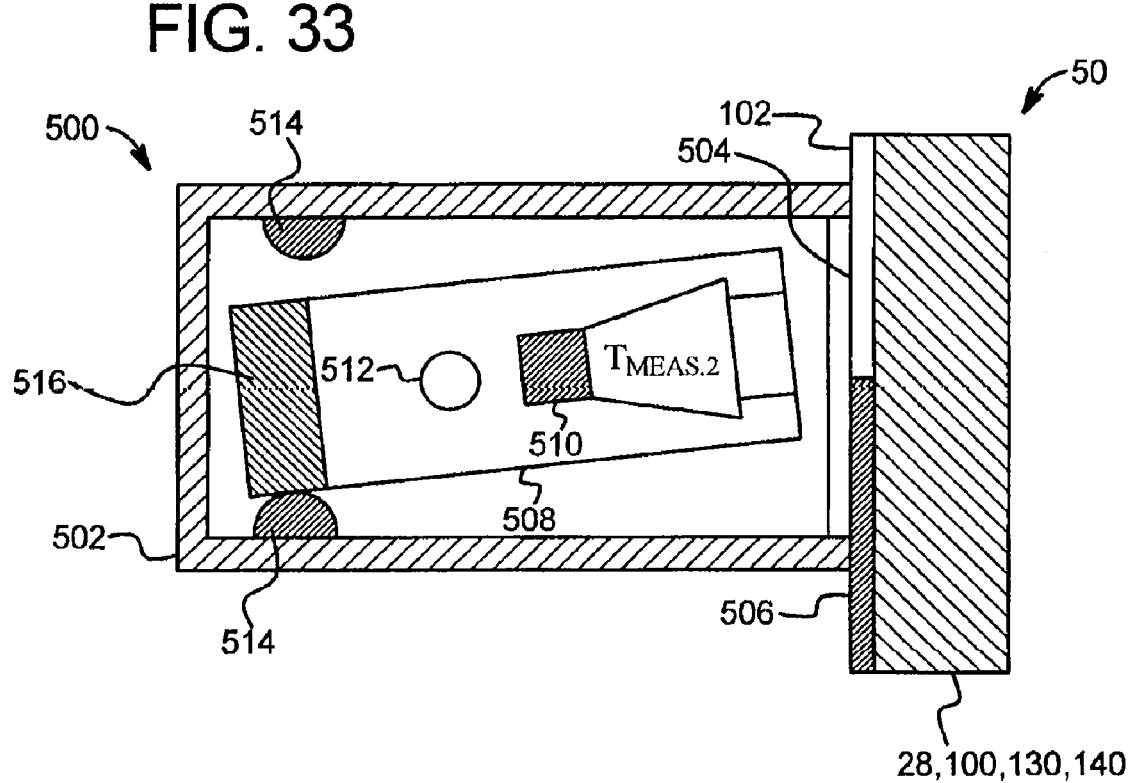
FIG. 33 is a schematic view of one embodiment for a non-invasive temperature sensing system and method having a temperature sensor in a second position.

Referring now to FIGS. 32 and 33, system 500 illustrates one possible fluid temperature measuring apparatus and method for system 10. Temperature measuring system 500 is advantageous because it is non-invasive. System 500 measures the temperature of fluid flowing through a portion of disposable set 50. For example, system 500 could measure the temperature of fluid flowing through disposable cassette 28, 100, 130, 140, e.g., upstream, downstream or directly at a fluid heating pathway of a cassette used with inline heating. Or, the fluid could be sensed while flowing through one of the fluid lines, such as directly upstream and/or downstream of the fluid heater. Further alternatively, the fluid could be sensed while residing within a bag or container, such as a warmer bag used with batch heating.

In the illustrated embodiment, system 500 includes a housing 502, which is part of instrument 20 of system 10. For example, housing 502 can be integrated into interface plate 185 described above in connection with FIGS. 19 to 21. When cassette 28, 100, 130, 140 is loaded into instrument 20, a portion of the cassette is pressed against housing 502. Housing 502 can be plastic or metal and should be at least substantially opaque, e.g., to infrared wavelengths. With the cassette 28, 100, 130, 140 compressed against housing 502 and the door of instrument or machine 20 closed on the other side of cassette 28, 100, 130, 140, little ambient light reaches the portion of cassette 28, 100, 130, 140 interfacing with system 500.

Sheeting 102 of cassette 28, 100, 130, 140 includes a portion 504 transparent, e.g., to infrared wavelengths, and a non-transparent or opaque portion 506. Portions 504 and 506 are placed adjacent to housing 502. Opaque portion 506 is formed for example via an inking (e.g., ink-jetting), printing or painting (e.g., spray painting) process. Alternatively, opaque portion 506 is formed via an opaque patch adhered to the disposable item. The size of opaque portion 506 can range from about ¼ inch by ¼ inch (6.4 mm by 6.4 mm) to about one inch by one inch (2.54 cm by 2.54 cm) or the same size in diameter if circular. Transparent portion 504 can be the clear sheeting 102 and can have an infrared target area at least as large as that of opaque portion 506. The size of the target area depends upon the infrared sensor selected and the distance that the sensor is mounted away from the target area. For example, a MIKRON M50 infrared sensor suitable for this application has a ½ inch (1.27 mm) target diameter when pressed against the target. The target diameter increases to 1¼ inch (3.18 cm) when the sensor is moved to six inches (15.25 cm) from the target.

Temperature measuring system 500 includes an arm 508, which holds a temperature sensor 510. Arm 508 is able to pivot back and forth at a pivot point 512, so that temperature sensor 510 is pointed selectively at either transparent portion 504 or opaque portion 506. Temperature sensor 510 in one embodiment is an infrared temperature sensor. Suitable infrared temperature sensors 510 are provided by PerkinElmer (Walthen, Mass.), Dexter Research (Dexter, Mich.), Electro Optical Components (Santa Rosa, Calif.).

In the illustrated embodiment, housing 502 includes electromagnets 514. When energized, the electromagnets will push and/or pull on a metal portion of magnetized pivot arm 516. Reversing the polarity will cause the polarity orientation to change. Arm 508 includes a magnetic, e.g., steel, portion 516, which is pulled towards one of the electromagnets 514 when that electromagnet is energized. Electromagnets control the orientation of the infrared temperature sensor so that infrared temperature sensor 510 can be pointed selectively (i) at opaque portion 506 to take a first temperature reading, $temp_{wall}$, of the sheeting 102 only as seen in FIG. 32 or (ii) at clear portion 504 to take a second temperature reading, $temp_{wall\ and\ fluid}$, which is a combination ($A*temp_{wall} + B*temp_{fluid}$) of the sheeting 102 and the fluid within the sheeting 102 as seen in FIG. 33. A and B are constants dependent upon the film or tube thickness and composition and are determined experimentally.

Because $temp_{wall}$ is measured and known, the fluid temperature $temp_{fluid}$ can be calculated using measured $temp_{wall}$ and measured $temp_{wall\ and\ fluid}$ according to the equation:

$$temp_{fluid} = \frac{[\text{measured } temp_{wall\,and\,fluid} - (A) * (\text{measured } temp_{wall})]}{B}$$

A processor and memory on a temperature controller or at a central processing unit store constants A and B and perform the above calculation. Temperature sensing system 500 should provide near real time, non-invasive monitoring of the fluid temperature.

Sensor 510 is flipped back and forth and the different temperature measurements are taken for example, every second. Alternatively, two independent infrared temperature sensors are used, one for infrared energy transmissive portion 504 and the other for infrared energy non-transmissive portion 506. Further, alternatively, a dual or quadruple infrared sensor package is used, such as a Perkinselmer® TPS 2534 dual element thermopile or TPS-4339 Quad Element thermopile. The quad element system provides redundant temperature measurement. Multiple sensors remove calibration complexity.

A motor or solenoid could be used instead of electromagnets. Further alternatively, arm 508 could be pushed by a spring to one pivot position and pneumatically retracted to the second pivot position.

Figure 34:
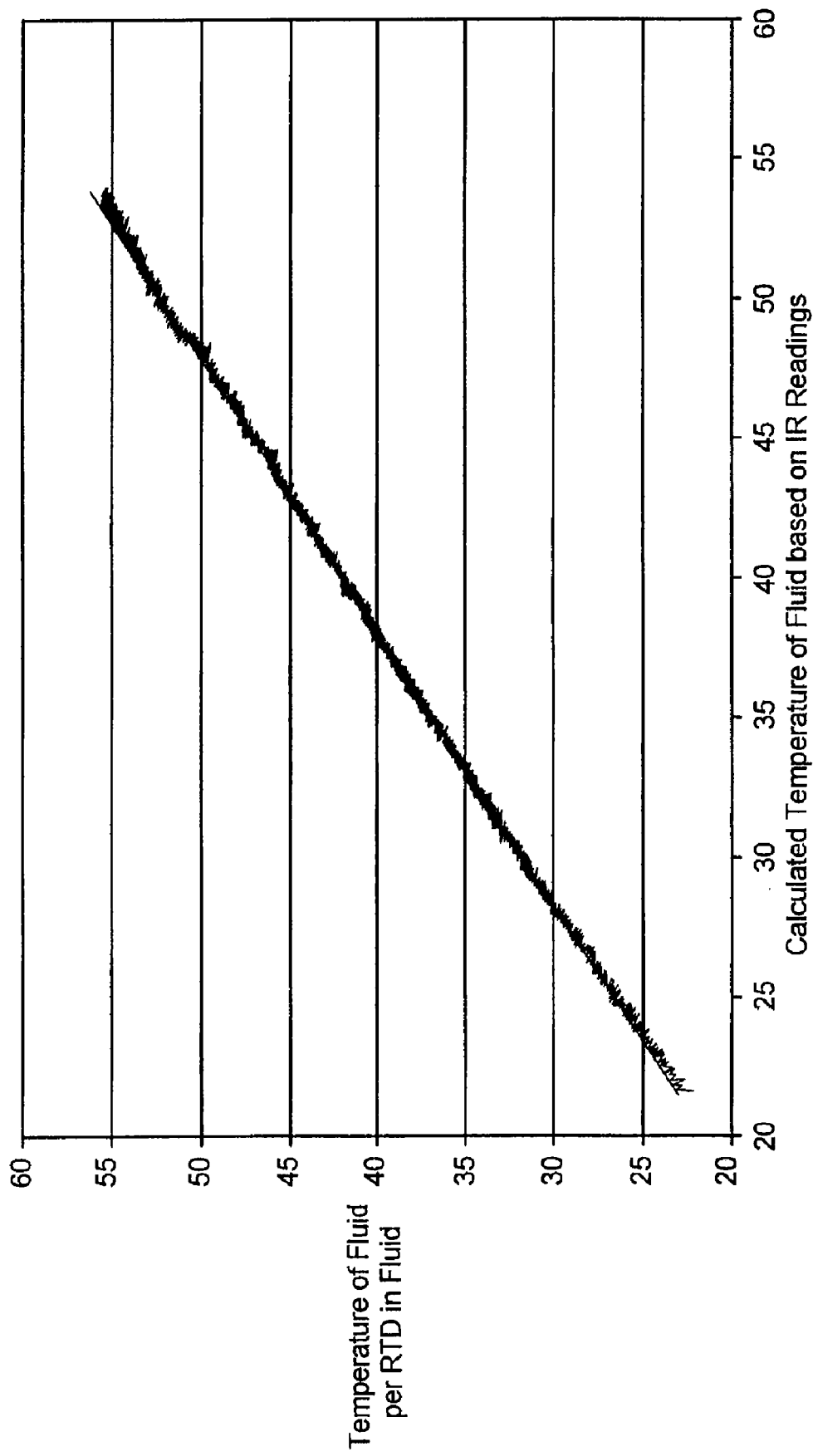
FIG. 34 is a graph comparing the results of the temperature sensing system of FIGS. 32 and 33 versus those of an invasive temperature sensor.

Referring now to FIG. 34, data illustrating the accuracy of fluid sensing system 500 is shown. System 500 in FIG. 34 appears to provide temperature readings non-invasively that approach the accuracy and response time of an invasive temperature sensor. The correlation between the readings from a resistance temperature detector ("RTD") sensor immersed in the fluid to the calculated readings from infrared sensing system 500 is good especially considering that the fluid temperature rose from just over 20° C. to over 50° C. during a ten minute time span in which the temperature readings were taken. In the example, constant A was set to 0.877985 and constant B was set to 0.109635. The curve fit line was found to be $T_{CALC}=1.047*T_{RTD}-0.0303$.

Multi-Chamber Bag Open Sensor

Referring now to FIGS. 35 and 36, inductive sensing system 530 illustrates one embodiment for detecting: (i) whether a single chamber supply bag 40 (referring generally to supply bags 40a to 40d discussed above) or a multi-chamber supply bag 540 is residing on a particular one of shelves 32, 34, 36 and 38; and (ii) if the supply bag is a multi-chamber supply bag 540, whether an associated frangible seal 542 has been broken allowing two or more concentrates 544a and 544b from separate chambers 546a and 546b, respectively, to mix.

Multi-chamber supply bag inductive sensing system 530 measures current, which for a fully opened container is indicative of either electrical conductivity or electrical impedance. The measured current indicates whether frangible seal 542 between chambers 546a and 546b of multi-chamber bag 540 has been broken so that previously separated solutions can mix prior to delivery to a patient.

The different concentrates 544a and 544b within separate chambers 546a and 546b of multi-chamber bag 540 have different concentrations of ions. The different ionic nature of different concentrates 544a and 544b provides an opportunity to correlate a measured current in a mixed solution to a conductivity or impedance of the solution. System 530 can thereby compare the determined conductivity or impedance with an expected conductivity or impedance to confirm whether the concentrates have been mixed properly. System 530 is non-invasive, which is advantageous when dealing with sterile medical fluids, such as dialysis fluids. It should be appreciated that system 530 can also operate with non-sterile or non-injectable fluids.

System 530 includes a first coil 532 and a second coil 534, which are located in different positions within the limits of the tray or shelf (e.g., one of shelves 32 to 38) onto which multi-chamber bag or container 540 is placed for treatment. For example, coils 532 and 534 are installed on top of or underneath the tray or shelf (e.g., one of shelves 32 to 38) or are laminated within the tray or shelf. If installed on top of the tray, coils 532 and 534 can be covered with a protective coating or layer. Coils 532 and 534 can for example be formed from single stranded wire or multi-stranded wire, such as litzwire. In the illustrated embodiment, coils 532 and 534 are pancake or flat coils.

One of coils 532 and 534 performs a transmitter function while the other of the coils performs a receiver function. The coils can be dedicated to one of the functions, e.g., coil 532 transmits and coil 534 receives as shown in FIGS. 36 and 37. Alternatively, coils 532 and 534 alternate between the transmitter and receiver functions.

A signal (voltage or current) generator 536 excites transmitter coil 532 with a signal that varies with time, such as sine wave, square wave, sawtooth wave or other time variable wave. Generator 536 can be for example (i) a logic level oscillator, (ii) a combination of oscillator and filter or (iii) a waveform generator circuit. One suitable voltage range includes four to twenty volts. Transmitter coil 532 induces small currents in the dialysate, while receiver coil 534 senses those currents. The intensity of the currents that receiver coil 534 senses depends on the type of solution and the degree of electrical coupling between bags and coils 532 and 534. For example, if the shape of the supply bag or container is such that its footprint does not project on top of a receiver coil, the receiver coil will not sense any current. If the shape of the supply bag or container is such that its footprint does not project on top of a transmitter coil, the transmitter coil will induce no current or relatively little current into the solution.

FIG. 35 shows that unopened seal 542 causes container 540 to couple less effectively with the flat areas of chambers 546a and 546b that lie flat on the tray or shelf. Accordingly, a sensor or measuring device 538 will measure less current from receiver coil 534. This level of current in FIG. 35 is shown to reside in a "not mixed" range. Current measuring device 538 in one embodiment is a multimeter or an ammeter.

FIG. 36 shows that opened seal 542 couples equally effectively with the flat areas of chambers 546a and 546b, since the entire bag or container now lies flat on the tray or shelf. Accordingly, sensor or measuring device 538 measures more current from receiver coil 534. This level of current in FIG. 36 is shown to reside in a "mixed" range.

FIGS. 37A to 37D illustrate an inductive system 560 that can determine whether bag 540 is positioned and oriented correctly on tray or shelf 32, 34, 36 or 38. Bag 540 shown from the top in FIGS. 37A to 37D shows frangible seal 542 separating chambers 546a and 546b. System 560 includes four coils 532a, 532b, 534a and 534b. Each coil can be used for either transmission or reception. The arrows represent some of the possible couplings between the coils.

Figure 37A:
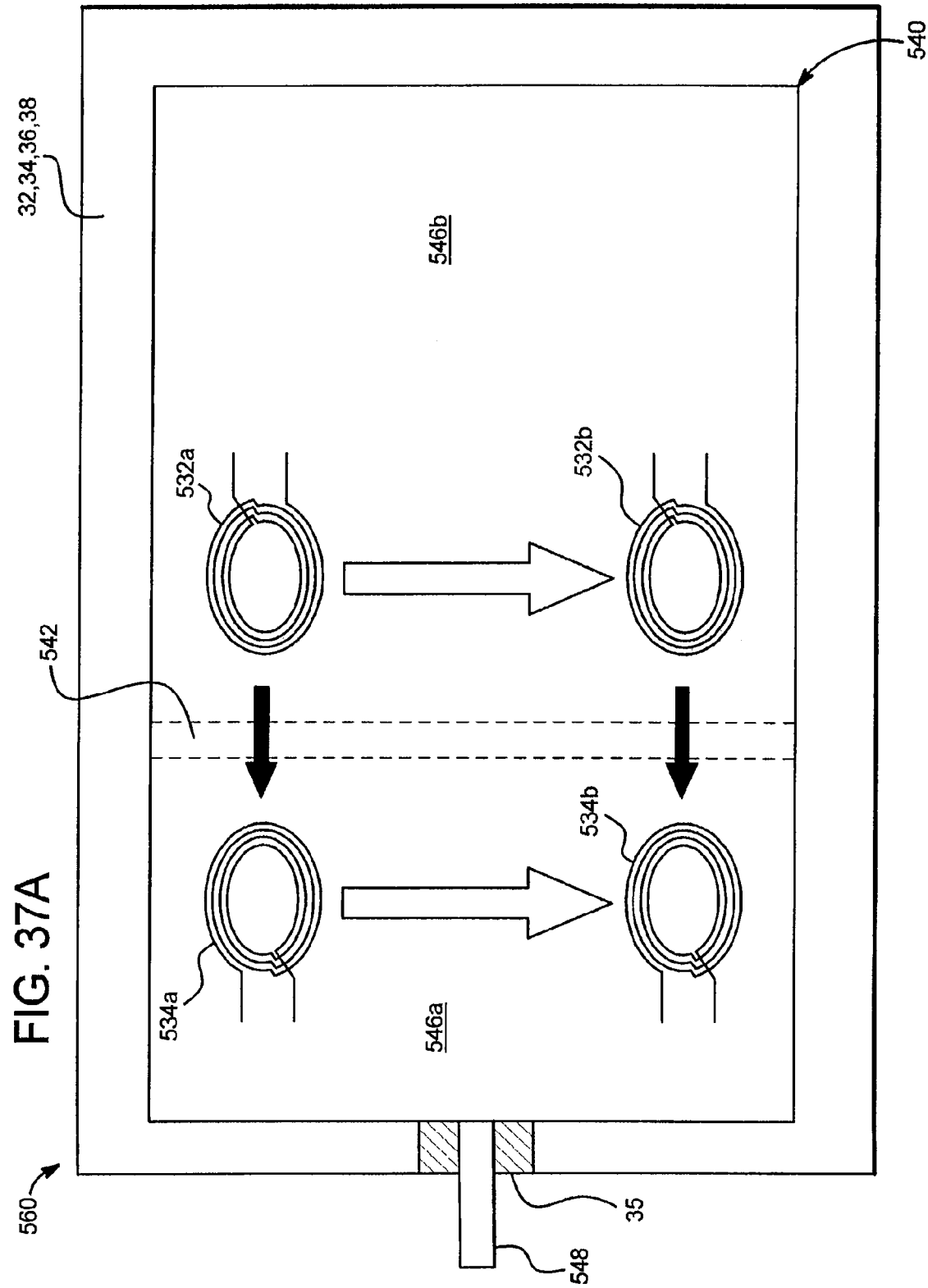

FIG. 37A illustrates a proper loading of bag 540, in which a port or pigtail 548 of bag 540 is aligned with and rests in aperture 35 of tray or shelf 32, 34, 36 or 38. Here, seal 542 separates coils 532a and 532b from coils 534a and 534b, respectively. Seal 542 does not separate coil 532a from coil 534a or coil 534a from coil 534b. The proper loading position or orientation of FIG. 37A therefore results in a signature inductive coupling pattern of (i) coil 532a to coil 532b—high coupling, (ii) coil 534a to coil 534b—high coupling, (iii) coil 532a to coil 534a—low coupling, and (iv) coil 532b to coil 534b—low coupling.

The improperly loaded bag 540 of FIG. 37B on the other hand results in a different inductive coupling pattern of (i) high coupling, (ii) high coupling, (iii) high coupling, and (iv) high coupling because all four coupling coils are located on one side of frangible seal 542. The improperly loaded bag 540 of FIG. 37C results in still a different inductive coupling pattern of (i) low coupling, (ii) low coupling, (iii) high coupling, and (iv) high coupling due the position of seal 542 relative to the coils illustrated in FIG. 37C. The improperly loaded bag 540 of FIG. 37D results in the same inductive coupling pattern of FIG. 37C, namely, (i) low coupling, (ii) low coupling, (iii) high coupling, and (iv) high coupling due the position of seal 542 relative to the coils illustrated in FIG. 37D.

A system controller takes the four measurements before seal 542 is broken and categorizes the coupling signature into either a bag properly loaded state or an improperly loaded state. The electronics of system 10 in one embodiment include a multiplexer that sequences through each of transmitter/receiver pairs (i) to (iv) upon receiving a signal from a load cell detecting that a bag has been loaded or upon receiving an input from the user that a bag or bags have been loaded. A single signal source 536 can be multiplexed to a desired coil functioning as the transmitter for the particular pair being sensed, e.g., coil 532a for pair (i), coil 534a for pair (ii), coil 532a for pair (iii), and coil 534a for pair (iv) shown above. The multiplexer also sequences through a plurality of electrical switch states to electrically connect the appropriate coils of each pair (i) to (iv) to source 536 and sensor 538 at the appropriate time.

It is also possible, after determining that bag 540 has been loaded properly, that the controller can verify from the inductive coupling signature that the composition of concentrate solutions 544a and 544b in compartments 546a and 546b is correct according to an expected conductivity for each solution. Tested pairs (iii) and (iv) for the correct bag position of FIG. 37A reveal the conductivity for concentrates 544a and 544b of compartments 546a and 546b, respectively. If a conductivity is out of an expected range an error can be generated. The controller can also verify the integrity of seal 542. Before allowing treatment to begin, system 560 also verifies that seal 542 has been opened allowing concentrates 544a and 544b to mix. Once the solution is mixed, the conductivity of the mixed dialysate can also be checked.

Correct bag positioning is useful for systems that use gravity for any of the treatment operations. Verification of each of the individual solutions allows determining if concentrations are adequate for the intended treatment. Verification of the integrity of the seal allows instrument 12 to ascertain that the solutions have not been mixed before treatment has begun. Premature mixture of the solutions considerably shortens the shelf life of the product. Such measurement ensures that no degradation of the solution has occurred.

The above-mentioned controller can operate directly or indirectly with a central processing unit, which in turn operates with a video controller and graphical user interface ("GUI"). If all of the above checks are verified, system 10 causes GUI to display a "bag loading ok" or similar message and allows therapy to continue. If one of the bags 540 is loaded incorrectly, system 10 causes GUI to display a "check bag loading" or similar message and perhaps even identifies the bag, e.g., "check loading of second bag from top". If the bags 540 are loaded correctly but system 560 detects an abnormal conductivity, system 10 causes GUI to display a "check solution of bags loaded" or similar message and perhaps even identifies the bag, e.g., "check solution in second bag from top". If bag loading and concentration are verified but the user tries to begin therapy without opening one or all of bags 54, system 10 causes the GUI to display a "open bag seal prior to treatment" or similar message and perhaps even identifies the bag, e.g., "open seal of top bag prior to treatment".

FIGS. 4 to 9 illustrate a bag management system 30, which holds multiple supply bags at an angle for fluid flow and air handling purposes. It should be appreciated that inductive sensing systems 530 and 560 can operate at the bag angle of system 30, alternatively with bags 540 loaded at least substantially horizontally or further alternatively with bags 540 loaded at least substantially vertically. In slanted system 30, the coils can be laminated to an upper or lower surface of each tray or be embedded in the tray. With a vertical manager, the coils can be connected to one or more vertical bar that runs vertically up one of the bags and presses respective coils against each bag. Signals to the coils are supplied through vertical support bars. The bag management systems can supply additional information such as weight information via a load cell.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a dialysis instrument including at least one pump actuator;
   a disposable cassette operable with the at least one pump actuator, a plurality of supply lines connected to the disposable cassette, each supply line including a supply line connector and a supply line tip protector;
   a plurality of dialysis fluid containers, the dialysis fluid containers each including a solution line having a solution line connector and a solution line tip protector; and
   an auto-connection mechanism including a solution line connector holder, a supply line connector holder, one of the holders fixed, the other of the holders moveable, and a separate moveable tip protector remover configured and arranged to translate between the solution line connector holder and the supply line connector holder to remove each of the solution line tip protectors and each of the supply line tip protectors.

2. The dialysis system of claim 1, wherein the tip protector remover is configured to hold one of the solution line and supply line tip protectors, the other of the tip protectors configured to be held for removal by the tip protectors that are held by the tip protector remover.

3. The dialysis system of claim 2, the tip protector remover configured to grasp and hold the solution line tip protectors, the solution line tip protectors configured to grasp and hold the supply line tip protectors.

4. The dialysis system of claim 1, wherein the tip protector remover is translatable away from a path between the solution line connector holder and the supply line connector holder, allowing the connector holders to be mated.

5. The dialysis system of claim 1, wherein the solution line connector holder is fixed, and the supply line connector holder is translatable relative to the solution line connector holder.

6. The dialysis system of claim 1, which includes a door that closes prior to removal of tip protectors from the solution line connectors or supply line connectors, and a source of ultra-pure air positioned to saturate exposed connectors from behind the door.

7. The dialysis system of claim 1, which includes pinch clamps positioned to close at least one of the solution lines and the supply lines.

8. The dialysis system of claim 1, wherein at least one of the solution line connectors and the supply line connectors are held in an organizer, the organizer enabling the connectors to be loaded into the solution line connector holder or the supply line connector holder at once.

9. The dialysis system of claim 1, wherein the auto-connection mechanism is located on a front side of the dialysis instrument along with instrument controls.

10. The dialysis system of claim 1, which includes a camera positioned to read information placed on at least one of the solution line connectors when the solution line connectors are loaded into the solution line connector holder.

11. The dialysis system of claim 10, wherein the information is indicative of at least one of: a type and a volume of a solution in one of the dialysis fluid containers.

12. A dialysis system comprising:
a dialysis instrument including at least one pump actuator;
a first set of lines and a first line set holder positioned on the dialysis instrument, each line of the first set of lines including a connector and a tip protector;
a second set of lines and a second line set holder positioned on the dialysis instrument, each line of the second set of lines including a connector and a tip protector;
a separate tip protector remover positioned on the dialysis instrument; and at least one processor configured to cause
(i) the tip protector remover to translate between the first line set holder and the second line set holder to remove each of the tip protectors from both the first and second sets of lines,
(ii) the tip protector remover to move away from a path between the first and second line set holders, and
(iii) at least one of the first and second line set holders to move along the path to connect the first and second sets of lines.

13. The dialysis system of claim 12, the at least one processor operable with a plurality of stepper motors to remove the tip protector remover and at least one of the line set holders.

14. The dialysis system of claim 12, wherein the first and second line set holders are configured to hold the connectors at ends of the first and second sets of lines.

15. The dialysis system of claim 12, the processor further configured to cause the tip protector remover to extend away from the instrument to facilitate manual removal of the tip protectors from the tip protector remover.

16. The dialysis system of claim 12, the processor further configured to cause the tip protector remover to reconnect the tip protectors onto the sets of lines before the sets of lines are removed from the first and second line set holders.

17. A dialysis system comprising:
a disposable cassette;
a plurality of supply lines connected to the disposable cassette;
a supply connector located at an end of each supply line, each supply connector including a tip protector;
a plurality of dialysis fluid containers;
a solution line connected to each dialysis fluid container;
a solution connector located at an end of each solution line, each solution connector including a tip protector;
a supply connector holder;
a solution connector holder;
a separate tip protector remover; and
a plurality of motors;
wherein the holders, tip protector remover and motors are configured and arranged to move (i) the tip protector remover towards each of the holders to remove each of the supply line tip protectors and each of the solution line tip protectors; and (ii) at least one the holders toward and away from each other.

18. The dialysis system of claim 17, further including a dialysis instrument having at least one pump actuator, the holders and tip protector remover connected to the dialysis instrument.

* * * * *